(12) United States Patent
Belmont et al.

(10) Patent No.: US 7,195,902 B2
(45) Date of Patent: Mar. 27, 2007

(54) PHOSPHATASES WHICH ACTIVATE MAP KINASE PATHWAYS

(75) Inventors: John W. Belmont, Houston, TX (US); Frederick A. Fletcher, Ventura, CA (US); Alice J. Chen, Houston, TX (US); Roland Jurecic, Key Biscayne, FL (US); Tse-Hua Tan, Houston, TX (US); Guisheng Zhou, Houston, TX (US)

(73) Assignees: Amgen Corporation, Seattle, WA (US); Baylor College of Medicine, Houston, TX (US)

( * ) Notice: Subject to any disclaimer, the term of this patent is extended or adjusted under 35 U.S.C. 154(b) by 408 days.

(21) Appl. No.: 10/803,738

(22) Filed: Mar. 18, 2004

(65) Prior Publication Data
US 2005/0014222 A1 Jan. 20, 2005

Related U.S. Application Data

(62) Division of application No. 09/665,819, filed on Sep. 20, 2000, now Pat. No. 6,900,043.

(60) Provisional application No. 60/155,068, filed on Sep. 21, 1999.

(51) Int. Cl.
*C12N 9/14* (2006.01)
(52) U.S. Cl. ............... 435/195; 435/196; 536/23.2
(58) Field of Classification Search ............... None
See application file for complete search history.

(56) References Cited

U.S. PATENT DOCUMENTS

| | | | |
|---|---|---|---|
| 4,179,337 A | 12/1979 | Davis et al. | |
| 4,376,110 A | 3/1983 | David et al. | |
| 4,816,567 A | 3/1989 | Cabilly et al. | |
| 4,945,050 A | 7/1990 | Sanford et al. | |
| 4,970,154 A | 11/1990 | Chang | |
| 5,234,784 A | 8/1993 | Aslam et al. | |
| 5,364,791 A | 11/1994 | Vegeto et al. | |
| 5,399,346 A | 3/1995 | Anderson et al. | |
| 5,459,036 A | 10/1995 | Lechner et al. | |
| 5,489,743 A | 2/1996 | Robinson et al. | |
| 5,557,032 A | 9/1996 | Mak | |

(Continued)

FOREIGN PATENT DOCUMENTS

CA   2 337 670   1/2001

(Continued)

OTHER PUBLICATIONS

Ford et al. Fusion Tails for the recovery and purification of recombinant protein. Protein Expre. Purif. 1991, 2, 95-107.*

(Continued)

*Primary Examiner*—Nashaat T. Nashed
(74) *Attorney, Agent, or Firm*—McDonnell Boehnen Hulbert & Berghoff LLP

(57) ABSTRACT

The present invention provides novel JNK activating phosphatase polypeptides and nucleic acid molecules encoding the same. The invention also provides vectors, host cells, antibodies and methods for producing JNK activating phosphatase polypeptides. Also provided for are methods for the diagnosis and treatment of diseases associated with JNK activating phosphatase polypeptides.

5 Claims, 15 Drawing Sheets

U.S. PATENT DOCUMENTS

| | | | |
|---|---|---|---|
| 5,589,362 | A | 12/1996 | Bujard et al. |
| 5,593,875 | A | 1/1997 | Wurm et al. |
| 5,631,236 | A | 5/1997 | Woo et al. |
| 5,635,399 | A | 6/1997 | Kriegler et al. |
| 5,650,298 | A | 7/1997 | Bujard et al. |
| 5,654,168 | A | 8/1997 | Bujard et al. |
| 5,663,314 | A | 9/1997 | Seger et al. |
| 5,672,344 | A | 9/1997 | Kelley et al. |
| 5,672,510 | A | 9/1997 | Eglitis et al. |
| 5,676,954 | A | 10/1997 | Brigham |
| 5,679,559 | A | 10/1997 | Kim et al. |
| 2005/0176124 | A1* | 8/2005 | Luche et al. ............... 435/196 |

FOREIGN PATENT DOCUMENTS

| | | |
|---|---|---|
| EP | 401384 A1 | 12/1990 |
| WO | WO 91/09955 | 7/1991 |
| WO | WO 94/28122 | 12/1994 |
| WO | WO 95/24670 | 12/1995 |
| WO | WO 96/37609 | 11/1996 |
| WO | WO 96/40958 | 12/1996 |
| WO | WO 96/41865 | 12/1996 |
| WO | WO 97/00315 | 1/1997 |
| WO | WO 97/16442 | 5/1997 |
| WO | WO 97/31899 | 9/1997 |
| WO | WO 00/06728 | 2/2000 |
| WO | WO 01/02581 | 1/2001 |

OTHER PUBLICATIONS

Blackshear, et al., "Brca1 and Brca2 expression patterns in mitotic and meiotic cells of mice," *Oncogene*, vol. 16, pp. 61-68 (1998), U.S.

Albrecht, A., et al., "In-situ Hybridization Protocol," *Molecular and Cellular Methods in Developmental Toxology*, Internet Abstract, pp. 1-7 (1996).

Cooper, et al., "Acceleration of onset of collagen-induced arthritis by intra-articular injection of tumour necrosis factor or transforming growth factor-beta," *Clin. Exp. Immunol.*, vol. 89, pp. 244-250 (1992).

Dinarello, "The biological properties of interleukin-1," *Eur Cytokine Netw*, vol. 5, No. 6, pp. 517-531, PubMed Abstract (1994).

MacDonald, "Expression of the Pancreatic Elastase I Gene in Transgenic," *Hepatology*, vol. 7, No. 1, pp. 42S-51S (1987).

Moore, et al., "Analysis of Protein Phosphorylation," *Current Protocols in Molecular Biology*, Chapter 18, pp. 18.03; 18.1.1-18.1.5; 18.2.1-18.2.7; 18.3.1-18.3.8; 18.4.1-18.4.7; 18.5.1-18.5.9; 18.6.1-16.6.19 (1995).

Petty, "Metal-Chelate Affinity Chromatography," *Current Protocols in Molecular Biology*, Chapter 10, pp. 10.11.10-10.11.24 (1996).

Sola, "Using Monoclonal Antibodies: Soluble Antigens," *Monoclonal Antibodies: A Manual of Techniques*, pp. 147-158 (1987).

Wilkinson, "Whole mount in situ hybridization of vertebrate embryos," *A Practical Approach*, pp. 75-83 (1992).

"Gene Expression Technology," *Methods in Enzymology*, D. Goeddel (Ed.) vol. 185, pp. v-ix.

A. Bradley, "Production and analysis of chimeaeric mice," pers. comm., and in *Teratocarinomas and Embryonic Stem Cells: A Practical Approach*, E.J. Robertson, Ed. (IRL Press. Oxford, 1987, pp. 113-152).

A.J. Flint, et al., "Development of substrate-trapping mutants to identify physiological substrates of protein tyrosine phosphatases," *Proc. Natl. Acad. Sci.*, vol. 94, pp. 1680-1685 (1997).

A.J. Garton, et al., "Identification of p130$^{cas}$ as a Substrate for the Cytosolic Protein Tyrosine Phosphatase PTP-PEST," *Mol Cell Biol.*, vol. 16, pp. 6408-6418 (1996).

Adams et al., "The *c-myc* oncogene driven by immunoglobulin enhancers induces lymphoid malignancy in transgenic mice," *Nature*, vol. 318, pp. 533-538 (1985).

Adams et al., "Tyrosine Kinase and c-Jun NH$_2$-Terminal Kinase Mediate Hypertrophic Responses to Prostaglandin F$_{2\alpha}$ in Cultured Neonatal Rat Ventricular Myocytes," *Circ. Res.*, vol. No. 83, No. 2, pp. 167-178 (1998).

Alexander et al., "Expression of the *c-myc* Oncogene under Control of an Immunoglobulin Enhancer in Eµ-myc Transgenic Mice," *Mol. Cell. Biol.*, vol. 7, pp. 1436-1444 (1987).

Needleman and Wunsch, "A General Method Applicable to the Search for Similarities in the Amino Acid Sequence of Two Proteins," *J. Mol. Biol.*, vol. 48, pp. 443-453 (1970).

Altschul et al., "Basic Local Alignment Search Tool," *J. Mol. Biol.*, vol. 215, pp. 403-410 (1990).

Baracos et al., Stimulation of Muscle Protein Degradation and Prostaglandin E$_2$ Release by Leukocytic Pyrogen (Interleukin-1), The New England Journal of Medicine, vol. 308, No. 10, pp. 553-558 (1983).

Bernoist and Chambon, "*In vivo* sequence requirements of the SV40 early promoter region," *Nature*, vol. 290, pp. 304-310 (1981).

Beutler et al., "Recombinant Interleukin 1 Suppresses Lipoprotein Lipase Activity in 3T3-L1 Cells," *J. Immunol.*, vol. 135, pp. 3969 (1985).

Bolton et al., "A General Method for the Isolation of RNA Complementary to DNA," *Proc. Natl. Acad. Sci. U.S.A.*, vol. 48, pp. 1390 (1962).

Brahn et al., "Effects of Tumor Necrosis Factor Alpha (TNF-α) on Collagen Arthritis," *Lymphokine and Cytokine Research*, vol. 11, pp. 253-256 (1992).

Brinster et al., "Regulation of metallothionein-tymidine kinase fusion plasmids injected into mouse eggs," *Nature*, vol. 296, pp. 39-42 (1982).

Brodeur et al., "Mouse-Human Myeloma partners for the Production of Heterohybridomas," *Monoclonal Antibody Production Techniques and Applications*, pp. 51-63 (Marcel Dekker 1987).

Bruggermann et al., "Designer Mice: The Prodcution of Human Antibody Repertoires in Transgenic Animals," *Year in Immunol.*, vol. 7, pp. 33-40 (1993).

Carrtillo et al., "The Multiple Sequence Alignment Problem in Biology," *SIAM J. Applied Math.*, vol. 48, pp. 1073-1082 (1988).

Chandrasekhar et al., "Arthritic Induced by Interleukin-1 Is Dependent on the Site and Frequency of Intraaticular Injection," *Clinical Immunol Immunopathol.*, vol. 55, pp. 382-400 (1990).

Chien et al., "The two-hybrid system: A method to identify and clone genes for proteins that interact with a protein of interest," *Proc. Natl. Acad. Sci. U.S.A.*, vol. 88, pp. 9578-9832 (1991).

Clouse et al., "Monokine Regulation of Human Immunodeficiency Virus-1 Expression In A Chronically Infected Human T Cell Clone," *J. Immunol.*, vol. 142, pp. 431-438 (1989).

"Computational Molecular Biology—Sources and Methods for Sequence Analysis," A. Lesk, Ed. (Oxford University Press 1988).

"Methods in Molecular Biology 24—Computer Analysis of Sequence Data," Part 1, *Methods in Molecular Biology*, vol. 24 (1994), A.M. Griffin, et al, Ed., pp. v-xi.

D.C.I. Goberdhan and C. Wilson, "JNK, cytoskeletal regulator and stress response kinase? A *Drosophila* perspective," *BioEssays*, vol. 20, pp. 1009-1019 (1998).

DeBoer et al., "The *tac* promoter: A functional hybrid derived from the *trp* and *lac* promoters," *Proc. Natl. Acad. Sci. U.S.A.*, vol. 80, pp. 21-25 (1983).

Devereux et al., "A comprehensive set of sequence analysis programs for the VAX," *Nuc. Acids Res.*, vol. 12, pp. 387-395 (1984).

Doetschman et al., "Targetted correction of a mutant HPRT gene in mouse embryonic stem cells," *Nature*, vol. 330, pp. 576-578 (1987).

Doetschman et al., "Targeted mutation of the *Hprt* gene in mouse embryonic stem cells," *Proc. Natl. Acad. Sci. U.S.A.*, vol. 85, pp. 8583-8587 (1988).

C. Lang et al., "Tumor Necrosis Factor Impairs Insulin Action on Peripheral Glucose Disposal and Jepatic Glucose Output," *Endocrinol.*, vol. 130, pp. 43-52 (1994).

D. Szalkowski et al., "Antidiabetic Thiazolidinediones Block the Inhibitory Effecdt of Tumor Necrusus Factor-α on Differentiation, Insulin-Stimulated Glucose Uptake, and Gene Expression in 3T3-L1 Cells," *Endocrinol.*, vol. 136, pp. 1474-1481 (1995).

Engels et al., "Gene Synthesis," *Angew. Chem. Intl. Ed.*, vol. 28, pp. 716-734 (1989).

Firestein et al., "Stromelysin and Tissue Inhibitor of Metalloproteinases Gene Expression in Rheumatoid Arthritis Synovium," *Am. J. Pathol.*, vol. 140, pp. 1309-1314 (1992).

Folks et al., "Susceptibility of Normal Human Lymphocytes to Infection with HTLV-III/LAV," *J. Immunol.*, vol. 136, pp. 4049-4053 (1986).

Grosschedl et al., "Introduction of a µ Immunoglobulin Gene into the Mouse Germ Line: Specific Expression in Lymphoid Cells and Synthesis of Functional Antibody," *Cell*, vol. 38, pp. 647-658 (1984).

Hammer et al., "Diversity of Alpha-Fetoprotein Gene Expression in Mice is Generated by a Combination of Separate Enhancer Elements," *Science*, vol. 235, pp. 53-58 (1987).

Hefti, "Neurotrophic Factor Therapy for Nervous System Degenerative Diseases," *J. Neurobiology*, vol. 25, pp. 1418-1435 (1994).

Doetschman et al., "Targeted mutation of the *Hprt* gene in mouse embryonic stem cells," *Proc. Natl. Acad. Sci. U.S.A.*, vol. 85, pp. 8583-8587 (1988).

Hoogenboom et al., "By-passing Immunisation—Human Antibodies from Synthetic Repertoires of Germline $V_H$ Gene Segments Rearranged *in Vitro*" *J. Mol. Biol.*, vol. 227, pp. 381-388 (1992).

Houghten et al., "General method for the rapid solid-phase synthesis of large numbers of peptides: Specificity of antigen-antibody interatction at the level of individual amino acids," *Proc Natl Acad. Sci. USA*, vol. 82, pp. 5131-5135 (1985).

J. Barth and R. Ivarie, "Polyvinyl Alcohol Enhances Detection of Low Abundance Transcripts in Early Stage Quail Embryos in a Nonradioactive Whole Mount *In Situ* Hybridization Technique," *Biotechniques*, vol. 17, pp. 324-326 (1994).

J.M. Denu, J. A. Stuckey, M.A. Saper, J.E. Dixon, "Form and Function in Protein Dephosphorylation," *Cell*, vol. 87, pp. 361-364 (1996).

Jakobovits, et al., "Analysis of homozygous mutant chimeric mice: Deletion of the immunoglobulin heavy-chain joining region block B-cell development and antibody production," *Proc. Natl. Acad. Sci. U.S.A.*, vol. 90, pp. 2551-2555 (1993).

Jones, et al., "Replacing the complementarity-determining regions in a human antibody with those from a mouse," *Nature*, vol. 321, pp. 522-525 (1986).

Kelsey et al., "Species- and tissue-specific expression of human $\alpha_1$-antitrypsin in transgenic mice," *Genes and Devel.*, vol. 1, pp. 161-171 (1987).

Kitts et al., "A method for Producing Recombinant Baculovirus Expresssion Vectors at High Frequency," *Biotechniques*, vol. 14, pp. 810-817 (1993).

Kohler, et al., "Continuous cultures of fused cells secreting antibody of predefined specificity," *Nature*, vol. 256, pp. 495-497 (1975).

Kollias et al., "Regulated Expressin of Human $^A\gamma$-, β-, and Hybrid γβ-Globin Genes in Transgenic Mice: Manipulation of the Developmental Espression Patterns," *Cell*, vol. 46, pp. 89-94 (1986).

Kozbor et al., "A Human Hybrid Myeloma for Production of Human Monoclonal Antibodies," *J. Immunol.*, vol. 133, pp. 3001 (1984).

Krumlauf et al., "Development Regulation of α-Fetoprotein Genes in Transgenic Mice" *Mol. Cell. Biol.*, vol. 5, pp. 1639-1648 (1985).

Kucherlapati, "Homologous Recombination in Mammalian Somatic Cells" *Prog. in Nucl. Acid Res. and Mol. Biol.*, vol. 36, pp. 301-311 (1989).

Lähdevirta et al., "Elevated Levels of Circulating Cachectin/Tumor Necrosis Factor in Patients with Acquired Immunodeficiency Syndrome" *Am. J. Med.*, vol. 85, pp. 289-291 (1988).

Leder et al., "Consequences of Widespread Deregulation of the *c-myc* Gene in Transgenic Mice: Multiple Neoplasms and Normal Development" *Cell*, vol. 45, pp. 485-495 (1986).

Luckow et al., "Efficient Generation of Infectious Recombinant Baculoviruses by Site-Specific Transposon-Mediated Insertion of Foreign Genes into a Baculovirus Genome Propagated in *Escherichia coli*" *J. Virology.*, vol. 67, pp. 4566-4579 (1993).

Labastie et al., "Molecular Identity of Hermatopoietic Precursor Cells Emerging in the Human Embryo" *Blood*, vol. 92, pp. 3624-3635 (1998).

M.H. Cobb et al., "How MAP Kinases Are Regulated" *J. Biol. Chem.*, vol. 270, pp. 14843-14846 (1995).

Liu, et al., "Cytokine-induced neutrophil chemoattractant mRNA expressed in cerebral ischemia," *Neuroscience Letters*, vol. 164, pp. 125-128 (1993).

Liu, et al., "Tumor Necrosis Factor-α Expression in Ischemic Neurons," *Stroke*, vol. 25, No. 7, pp. 1481-1488 (1994).

Marks, et al., "By-passing Immunization: Human Antibodies from V-gene Libraries Displayed on Phage" *J. Mol. Biol.*, vol. 222, pp. 581-597 (1991).

Fiona, et al., "[20] Solubilization of Protein Aggregates" *Methods in Enzymology*, vol. 182, pp. 264-276 (1990).

Mason et al., "The Hypogonadal Mouse: Reproductive Functions Restored by Gene Therapy" *Science*, vol. 234, pp. 1372-1378 (1986).

Merrifield, R.B., "Solid Phase Peptide Synthesis. I. The Synthesis of a Tetrapeptide" *J. Am. Chem. Soc.*, vol. 85, pp. 2149-2154(1963).

Magram et al., "Development regulation of a cloned adult β-globin gene in transgenic mice" *Nature*, vol. 315, pp. 338-340 (1985).

Morrison, et al., "Chimeric human antibody molecules: Mouse antigen-binding domains with human constant region domains" *Proc. Natl. Acad. Sci., U.S.A.*, vol. 81, pp. 6851-6855 (1984).

Nemoto et al., "Opposing Effects of Jun Kinase and p38 Mitogen-Activated Protein Kinases on Cardiomyocyte Hypertrophy" *Mol. Cell. Biol.*, vol. 18(6), pp. 3518-3526 (1998).

Ornitz et al., "Elastase I Promoter Directs Expression of Human Growth Hormone and SV40 T Antigen Genes to Pancreatic Acinar Cells in Transgenic Mice" *Cold Spring Harbor Symp. Quant. Biol.*, vol. 50, pp. 399-409 (1986).

Pinkert et al., "An albumin enhancer located 10 kb upstream functions along with its promoter to direct efficient, liver-specific expression in transgenic mice" *Genes and Devel.*, vol. 1, pp. 268-276 (1987).

Jurecic et al., "Identification and Cloning of Differentially Expressed Genes by Long-Distance Differential Display" *Anal. Biochem.*, vol. 259, pp. 235-244 (1998).

Ramirez et al., "The MEKK-JNK Pathway Is Stimulated by α-Adrenergic Receptor and Ras Activation and Is Associated with *in Vitro* and *in Vivo* Cardiac Hypertrophy" *J. Biol. Chem.*, vol. 272 No. 22, pp. 14057-14061 (1997).

Readhead et al., "Expression of a Myelin Basic Protein Gene in Transgenic Shiverer Mice: Correction of the Dysmyelinating Phenotype" *Cell*, vol. 48, pp. 703-712 (1987).

Riechmann, et al., "Reshaping human antibodies for therapy" *Nature*, vol. 332, pp. 323-327 (1988).

Shani, "Tissue-specific expression of rat myosin light-chain 2 gene in transgenic mice" *Nature*, vol. 314, pp. 283-286 (1985).

Shohami et al., "Closed Head Injury Triggers Early Production of TNFα and IL-6 by Brain Tissue" *J. Cereb. Blood Flow Metab.*, vol. 14, pp. 615-619 (1994).

Silberbach et al., "Extracellular Signal-regular Protein Kinase Activation Is Required for the Anti-hypertrophic Effect of Atrial Natriuretic Factor in Neonatal Rat Ventricular Myocytes" *J. Biol. Chem.*, vol. 274, No. 35, pp. 24858-24864 (1999).

Swift et al., "Tissue-Specific Expression of the Rat Pancreatic Elastase I Gene in Transgenic Mice" *Cell*, vol. 38, pp. 639-646 (1984).

Jaffredo et al., "Intraaortic hemopoietic cells are derived from endothelial cells during ontogeny" *Development*, vol. 125, pp. 4575-4583 (1998).

Thomas et al., "Site-Directed Mutagenesis by Gene Targeting in Mouse Embryo-Derived Stem Cells" *Cell*, vol. 51, pp. 503-512 (1987).

Thomas et al., "High Frequency Targeting of Genes to Specific Sites in the Mammalian Genome" *Cell*, vol. 44, pp. 419-428 (1986).

Verhoeyen et al., "Reshaping Human Antibodies: Grafting an Antilysozyme Activity" *Science*, vol. 239, pp. 1534-1536 (1988).

Villa-Kamaroff et al., "A bacterial clone synthesizing proinsulin" *Proc. Natl. Acad. Sci. U.S.A.*, vol. 75, pp. 3727-3731 (1978).

W. Nürnberg, et al., "DIG-Labeled RNA In Situ Hybridization Without Coverslipping," *Biotechniques*, vol. 18, pp. 406-410 (1995).

Wagner et al., "Nucleotide sequence of the thymidine kinase gene of herpes simplex virus type 1" *Proc. Natl. Acad. Sci. U.S.A.*, vol. 78, pp. 1441-1445 (1981).

Wang et al., "Cardiac Hypertrophy Induced by Mitogen-activated Protein Kinase Kinase 7, a Specific Activator for c-Jun $NH_2$-terminal Kinase in Ventricular Muscle Cells" *J. Biol. Chem.*, vol. 273, No. 10, pp. 5423-5426 (1998).

Ip et al., "Signal transduction by the c-Jun N-terminal kinase (JNK)—from inflammation to development" *Curr. Opin. Cell Biol.*, vol. 10, pp. 205-219 (1998).

Yamamoto, et al., "Identification of a Functional Promoter in the Long Terminal Repeat of Rous Sarcoma Virus," *Cell*, vol. 22, pp. 787-797 (1980).

Yano et al., "Differential Activation of Cardiac c-Jun Amino-Terminal Kinase and Extracellular Signal-Regulated Kinase in Angiotensin II-Mediated Hypertension" *Circ. Res.*, vol. 83, No. 7, pp. 752-760 (1998).

Jurecic, et al., "Differential mRNA display using anchored oligo-dT and long sequence-specific primers as arbitrary primers," *TIG*, vol. 12, No. 12, pp. 502-504 (1996).

Henikoff et al., *Proc. Natl. Acad. Sci. USA*, vol. 89, pp. 10915-10919 (Nov. 1992).

Keyse, S.M., *Biochimica et Biophysica Acta*, vol. 1265, pp. 152-160 (1995).

Marra et al., "*The WashU-HHMI Mouse EST Project*," unpublished (1996), ncbi.nlm.nih.gov/entrez/viewer.fcgi?db=nucleotide &val=1684006.

Xia et al., *Science*, vol. 270, pp. 1326-1331 (Nov. 1995).

Anafi M, et al., "SH2/SH3 adaptor proteins can link tyrosine kinases to a Ste20-related protein kinase, HPK1," *J Biol. Chem.*, vol. 272, pp. 27804, 1997, U.S.

Andresson MB, et al., "Differential regulation of parallel mitogen-activated protein kinases in cardiac myocytes revealed by phosphatase inhibition," *Biochem. Biophys. Res. Commun.*, vol. 251:328, 1998, U.S.

Aspenstrom P, et al., "Two GTPases, Cdc42 and Rac, bind directly to a protein implicated in the immunodeficiency disorder Wiskott-Aldrich syndrome," *Curr. Biol.*, vol. 6, pp. 70-75, 1996, U.S.

Avraham A, et al., "Co-stimulation-dependent activation of a JNK-kinase in T lymphocytes," *Eur. J. Immunol*,. vol. 28, pp. 2320-2330, 1998.

Beltman J, et al., "The selective protein kinase C inhibitor, Ro-31-8220, inhibits mitogen- activated protein kinase phosphatase- 1 (MKP-1) expression, includes c- Jun expression, and activates Jun N-terminal kinase," *J. Biol. Chem.*, vol. 271, pp. 27018-27024, 1996, U.S.

Ben-Levy R, et al., "Nuclear export of the stress-activated protein kinase p38 mediated by its substrate MAPKAP kinase-2," *Curr. Biol.*, vol. 8, No. 19, pp. 1049-1057, 1998.

Burgess GS, et al., "Regulation of the c-jun gene in p210 BCR-ABL transformed cells corresponds with activity of JNK, the c-jun N-terminal kinase," *Blood*, vol. 92, pp. 2450-2460, 1998, U.S.

Camps M, et al., "Catalytic activation of the phosphatase MKP-3 by ERK2 mitogen-activated protein kinase," *Science*, vol. 280, pp. 1262-1265, 1998, U.S.

Cavigelli M, et al., "The tumor promoter arsenite stimulates AP-1 activity by inhibiting a JNK phosphatase," *EMBO J.*, vol. 15, No. 22, pp. 6269-6279, 1996.

Ceresa BP, et al., "Signal transducer and activator of transcription-3 serine phosphorylation by insulin is mediated by a Ras/Raf/MEK-dependent pathway," *Endocrinology*, vol. 138, pp. 4131-4137, 1997, U.S.

Chen YR, "The role of c-Jun N-terminal kinase (JNK) in apoptosis induced by ultraviolet C and gamma radiation. Duration of JNK activation may determine cell death and proliferation," *J. Biol. Chem.*, vol. 271, pp. 31929-31936, 1996, U.S.

Chow CW, et al., "Nuclear accumulation of NFAT4 opposed by the JNK signal transduction pathway," *Science*, vol. 278, pp. 1638-1641, 1997, U.S.

Chu Y, et al., "The mitogen-activated protein kinase phosphatases PAC1, MKP-1, and MKP-2 have unique substrate specificities and reduced activity in vivo toward the ERK2 sevenmaker mutation," *J. Biol. Chem.*, vol. 271, pp. 6497-6501, 1996, U.S.

Cortez D., et al., "The Bcr-Abl tyrosine kinase activates mitogenic signaling pathways and stimulates G1-to-S phase transition in hematopoietic cells," *Oncogene*, vol. 15, pp. 2333-2342, 1997.

Cuenda A, et al., "Purification and cDNA cloning of SAPKK3, the major activator of RK/p38 in stress- and cytokine-stimulated monocytes and epithelial cells," *EMBO J.*, vol. 15, pp. 4156-4164, 1996, U.S.

Cuenda A, et al., "Activation of stress-activated protein kinase-3 (SAPK3) by cytokines and cellular stresses is mediated via SAPKK3 (MKK6); comparison of the specificities of SAPK3 and SAPK2 (RK/p38)," *EMBO J.*, vol. 16, pp. 295-305, 1997, U.S.

Cuenda A, et al., "Activation of the novel MAP kinase homologue SAPK4 by cytokines and cellular stresses is mediated by SKK3 (MKK6)," *Biochem. Soc. Trans.*, vol. 25, pp. S569, 1997.

Cuenda A., et al., "Differential activation of stress-activated protein kinase kinases SKK4/MKK7 and SKK1/MKK4 by the mixed-lineage kinase-2 and mitogen- activated protein kinase kinase (MKK) kinase- 1," *Biochem. J.*, vol. 333, pp. 11-15, 1998, Great Britain.

Diener K, et al., "Activation of the c-jun N-terminal kinase pathway by a novel protein kinase related to human germinal center kinase," *Proc. Natl. Acad. Sci.*, vol. 94, pp. 9687-9692, 1997, U.S.

Dolfi F, et al., "The adaptor protein crk connects multiple cellular stimuli to the JNK signaling pathway," *Proc. Natl. Acad. Sci.*, vol. 95, pp. 15394-15399, 1998, U.S.

Dowd S, et al., "Isolation of the human genes encoding the Pyst1 and Pyst2 phosphatases: characterization of Psyst2 as a cytosolic dual-specificity MAP kinase phosphatase and its catalytic activation by both MAP and SAP kinaes," *J. Cell. Sci.*, vol. 111, pp. 3389-3399, 1998, Great Britain.

Durham PL, et al., "Serotonergic repression of mitogen-activated protein kinase control of the calcitonin gene-related peptide enhancer," *Mol. Endocrinol.*, vol. 12, pp. 1002-1009, 1998, U.S.

Enslen H, et al., "Selective activation of p38 mitogen-activated protein (MAP) kinase isoforms by the MAP kinase kinases MKK3 and MKK6," *J. Biol. Chem.*, vol. 273, pp. 1741-1748, 1998, U.S.

Enslen H, et al., "Regulation of mitogen-activated protein kinases by a calcium/calmodulin- dependent protein kinase cascade," *Proc. Natl. Acad. Sci.*, vol. 93, pp. 10803-10808, 1996, U.S.

Fanger GR, et al., "MEK kinases are regulated by EGF and selectively interact with Rac/Cdc42," *EMBO J.*, vol. 16, pp. 4961-4972, 1997.

Finch A, et al., "Selective activation of JNK/SAPK by interleukin-1 in rabbit liver is mediated by MKK7," *FEBS Lett.*, vol. 418, pp. 144, 1997.

Fischer KD, et al., "Vav is a regulator of cytoskeletal reorganization mediated by the T- cell receptor," *Curr. Biol.*, vol. 8, pp. 554-562, 1998.

Foltz IN, et al., "Human mitogen-activated protein kinase kinase 7 (MKK7) is a highly conserved c-Jun N-terminal kinase/stress activated protein kinase (JNK/SAPK) activated by environmental stresses and physiological stimuli," *J. Biol. Chem.*, vol. 273, pp. 9344-9351, 1998, U.S.

Foltz IN, et al., "Activation of the stress-activated protein kinases by multiple hematopoietic growth factors with the exception of interleukin-4," *Blood*, vol. 89, pp. 3092-3096, 1997, U.S.

Franklin CC, et al., "Conditional expression of the mitogen-activated protein kinase (MAPK) phosphatase MKP-1 preferentially inhibits p38 MAPK and stress-activated protein kinase in U937 cells," *J. Biol. Chem.*, vol. 272, pp. 16917-16923, 1997, U.S.

Franklin CC, et al., "Conditional expression of mitogen-activated protein kinase phosphatase-1, MKP-1, is cytoprotective against UV-induced apoptosis," *Proc. Natl. Acad. Sci.*, vol. 95, pp. 3014-3019, 1998, U.S.

Fuchs SY, et al., "JNK targets p53 ubiquitination and degradation in nonstressed cells," *Genes. Dev.*, vol. 12, pp. 2658-2663, 1998, U.S.

Goedert M, et al., "Activation of the novel stress-activated protein kinase SAPK4 by cytokines and cellular stresses is mediated by SKK3 (MKKK6); comparison of its substrate specificity with that of other SAP kinases," *EMBO J.*, vol. 16, pp. 3563-3571, 1997, U.S.

Graves JD, et al., "Caspase-mediated activation and induction of apoptosis by the mammalian Ste20-like kinase Mst1," *EMBO J.*, vol. 17, pp. 2224-2234, 1998, U.S.

Groom LA, et al., "Differential regulation of the MAP, SAP and RK/p38 kinases by Pyst1, a novel cytosolic dual-specificity phosphatase," EMBO J., vol. 15, pp. 3621-3632, 1996, U.S.

Gu J, et al., "Tumor suppressor PTEN inhibits integrin- and growth factor-mediated mitogen-activated protein (MAP) kinase signaling pathways," J. Cell. Biol., vol. 143, pp. 1375-1383, 1998, U.S.

Guan Z, et al., "Induction of cyclooxygenase-2 by the activated MEKK1 Π SEK1/MKK4 Π p38 mitogen- activated protein kinase pathway," J. Biol. Chem., vol. 273, pp. 12901-12908, 1998, U.S.

Guan Z, et al., "Interleukin- 1beta-induced cyclooxygenase-2 expression requires activation of both c-Jun NH2-terminal kinase and p38 MAPK signal pathways in rat renal mesangial cells," J. Biol. Chem., vol. 273, pp. 28670-28676, 1998, U.S.

Guerrero C, et al., "Transformation suppressor activity of C3G is independent of its CDC25- homology domain," Oncogene, vol. 16, pp. 61, 1998.

Guo YL, et al., "Correlation between sustained c-Jun N-terminal protein kinase activation and apoptosis induced by tumor necrosis factor-alpha in rat mesangial cells," J. Biol. Chem., vol. 273, pp. 4027-4034, 1998, U.S.

Gupta S, et al., "Seletive interaction of JNK protein kinase isoforms with transcription factors," EMBO J., vol. 15, pp. 2760-2770, 1996, U.S.

Han J, et al., "Characterization of the structure and function of a novel MAP kinase kinase (MKK6)," J. Biol. Chem., vol. 271, pp. 2886-2891, 1996.

Hanada M., et al., "Selective suppression of stress-activated protein kinase pathway by protein phosphatase 2C in mammalian cells," FEBS Lett. vol. 437, pp. 172-176, 1998, Great Britain.

Hazzalin CA, et al., "p38/RK is essential for stress-induced nuclear response: JNK/SAPKs and c-Jun/ATF-2 phosphorylation are insufficient," Curr. Biol., vol. 6, pp. 1028-1031, 1996.

Hazzalin CA, et al., "Effects of the inhibition of p38/RK MAP kinase on induction of five fos and jun genes by diverse stimuli," Oncogene, vol. 15, pp. 2321-2331, 1997, U.S.

Healy JI, et al., "Different nuclear signals are activated by the B cell receptor during positive versus negative signaling," Immunity, vol. 6, pp. 419-428, 1997, U.S.

Heidenreich KA, et al., "Inhibition of p38 mitogen-activated by insulin in cultured fetal neurons," J. Biol. Chem., vol. 271, pp. 9891-9894, 1996, U.S.

Hirai S, et al., "Differential activation of two JNK activators, MKK7 and SEK1, by MKN28- derived nonreceptor serine/threonine kinase/mixed lineage kinase 2," J. Biol. Chem., vol. 273, pp. 7406-7412, 1998, U.S.

Hirsch DD, Stork PJ: mitogen-activated protein kinase phosphatases inactivate stress-activated protein kinase pathways in vivo. J Biol Chem 272:4568, 1997.

Holland PM, et al., "MKK7 is A stress-activated mitogen-activated protein kinase kinase functionally related to hemipterous," J. Biol. Chem. vol. 272, pp. 24994-24998, 1997, U.S.

Howe AK, et al., "Cell cycle progression in monkey cells expressing simian virus 40 small t antigen from adenovirus vectors," J. Virol. vol. 72, pp. 9637, 1998.

Hu MC, et al., "Human HPK1, a novel human hematopoietic progenitor kinase that activates the JNK/SAPK kinase cascade," Genes. Dev., vol. 10, pp. 2251, 1996.

Ichijo H, et al., "Induction of apoptosis by ASK1, a mammalian MAPKKK that activates SAPK/JNK and p38 signaling pathways," Science, vol. 275, pp. 90, 1997.

Janknecht R, et al., "Convergence of MAP kinase pathways on the ternary complex factor Sap- 1a," EMBO J., vol. 16, pp. 1620, 1997.

Jiang Y, et al., "Characterization of the structure and function of a new mitogen-activated protein kinase (p38beta)," J. Biol. Chem., vol. 271, pp. 17920, 1996.

Jiang Y, et al., "Characterization of the structure and function of the fourth member of p38 group mitogen-activated protein kinases, p38δ," J. Biol. Chem., vol. 272, pp. 30122, 1997.

Kallunki T, et al., "c-Jun can recruit JNK to phosphorylate dimerization partners via specific docking interactions," Cell, vol. 87, pp. 929, 1996.

Kao AW, et al., "Insulin stimulates the phosphorylation of the 66- and 52-kilodalton isoforms by distinct pathways," Endocrinology, vol. 138, pp. 2474, 1997.

Kawakami Y, et al., "Multiple signaling pathways for the activation of JNK in mast cells: involvement of Bruton's tyrosine kinase, protein kinase C, and JNK kinases, SEK1 and MKK7$^1$," J. Immunol., vol. 161, pp. 1795, 1998.

Keesler GA, et al., "Purification and activation of recombinant p38 isoforms α, β, γ, and δ," Protein Expr. Purif., vol. 14, pp. 221, 1998.

Kiefer F., et al., "HPK1, a hematopoietic protein kinase activating the SAPK/JNK pathway," EMBO J., vol. 15, pp. 7013, 1996.

Kurz AK, , et al., "Osmotic regulation of the heat shock response in primary rat hepatocytes," Hepatology, vol. 28, pp. 774, 1998.

Lee HY, et al., "All-trans-retinoic acid inhibits jun N-terminal kinase by increasing dual-specificity phosphatese activity," Mol. Cell. Biol., vol. 19, pp. 1973, 1999.

Lee-Kwon W, et al., "Antiapoptotic signaling by the insulin receptor in Chinese hamster ovary cells," Biochemistry, vol. 37, pp. 15747, 1998.

Liu R. Itoh T, et al., "Activation of c-Jun N-terminal kinase by human granulocyte macrophage- colony stimulating factor in BA/F3 cells," Biochem. Biophys. Res. Commun., vol. 234, pp. 611, 1997.

Liu Y, et al., "Role of mitogen-activated protein kinase phosphatase during the cellular response to genotoxic stress. Inhibition of c-Jun N-terminal kinase activity and AP-1-dependent gene activation," J. Biol. Chem., vol. 270, pp. 8377, 1995.

Liu Y, et al., "Age-related decline in mitogen-activated protein kinase activity in epidermal growth factor- stimulated rate hepatocytes," J. Biol. Chem., vol. 271, pp. 3604, 1996.

Ludwig S, et al., "The stress inducer arsenite activates mitogen-activated protein kinases extracellular signal-regulated kinases 1 and 2 via a MAPK kinase 6/p38- dependent pathway," J. Biol. Chem., vol. 273, pp. 1917, 1998.

Magi-Galluzzi C, et al., "Mitogen-activated protein kinase phosphatase 1 is overexpressed in prostate cancers and is inversely related to apoptosis," Lab. Invest., vol. 76, pp. 37, 1997.

Martin-Blanco E, et al., "puckered encodes a phosphatase that mediates a feedback loop regulating JNK activity during dorsal closure in Drosophila," Genes Dev., vol. 12, pp. 557, 1998.

Martin-Blanco E, "Regulatory control of signal transduction during morphogenesis in Drosophila," Int. J. Dev. Biol., vol. 42, pp. 363, 1998.

Matsuda N., et al., "Proliferation and differentiation of human osteoblastic cells associated with differential activation of MAP kinases in response to epidermal growth factor, hypoxia, and mechanical stress in vitro," Biochem. Biophys. Res. Commun., vol. 249, pp. 350, 1998.

Matsuda S, et al., "T lymphocyte activation signals for interleukin-2 production involve activation of MKK6- p38 and MKK7-SAPK/JNK signaling pathways sensative to cyclosporin A," J. Biol. Chem., vol. 273, pp. 12378, 1998.

Maulon L, et al., "T-Cell receptor signaling pathway exerts a negative control on thrombin-mediated increase in [Ca2+]l and p38 MAPK activation in Jurkat T cells: implication of the tyrosine kinase p56Lck," Blood, vol. 91, pp. 4232, 1998.

Maundrell K, et al., "Bcl-2 undergoes phosphorylation by c-Jun N-terminal kinase/stress- activated protein kinases in the presence of the constitutively active GTP-binding protein Rac1," J. Biol. Chem., vol. 272, pp. 25238, 1997.

May GH, et al., "Analysis of the interaction between c-Jun and c-Jun N-terminal kinase in vivo," J. Biol. Chem., vol. 273, pp. 33429, 1998.

Miralles F, et al., "UV irradiation induces the murine urokinase-type plasminogen activator gene via the c-Jun N-terminal kinase signaling pathway: requirement of a AP1 enhancer element," Mol. Cell. Biol., vol. 18, pp. 4537, 1998.

Miranti CK, et al., "Identification of a novel integrin signaling pathway involving the kinase Syk and the guanine nucleotide exchange factor Vav1," Curr. Biol., vol. 8, pp. 1289, 1998.

Moriguchi T, et al., "A Novel SAPK/JNK kinase, MKK7, stimulated by TNFα and cellular stresses," EMBO J., vol. 16, pp. 7045, 1997.

Muda M, et al., "The mitogen-activated protein kinase phosphatase-3 N-terminal noncatalytic region is responsible for tight substrate binding and enzymatic specificity," *J. Biol. Chem.*, vol. 273, pp. 9323, 1998.

Muda M, et al., "The dual specificity phosphatases M3/6 and MKP-3 are highly selective for inactivation of distinct mitogen-activated protein kinases," *J. Biol. Chem.*, vol. 271, pp. 2705, 1996.

Muda M., et al., "Molecular cloning and functional characterization of a novel mitogen- activated protein kinase phosphatase, MKP-4," *J. Biol. Chem.*, vol. 272, pp. 5141, 1997.

Nagata Y, et al., "Activation of p38 MAP kinase pathway by erythopoietin and interleukin-3," *Blood*, vol. 90, pp. 929, 1997.

Nagata Y, et al., "Activation of JNK signaling pathway by erythropoietin, thrombopoietin, and interleukin-3," *Blood*, vol. 89, pp. 2664, 1997.

Nagata Y, et al., "Activation of p38 MAP kinase and JNK but not ERK is required for erythropoietin-induced erythroid differentiation," *Blood*, vol. 92, pp. 1859, 1998.

Newberry EP, et al., "Fibroblast growth factor receptor signaling activates the human interstitial collagenase promoter via the bipartite Ets-AP1 element," *Mol. Endocrinol.*, vol. 11, pp. 1129, 1997.

Raingeaud J, et al., "MKK3- and MKK6-regulated gene expression is mediated by the p38 mitogen-activated protein kinase signal transduction pathway," *Mol. Cell. Biol.*, vol. 16, pp. 1247, 1996.

Raitano AB, et al., "The Bcr-Abl leukemia oncogene activates Jun kinase and requires Jun for transformation," *Proc. Natl. Acad. Sci.*, vol. 92, pp. 11746, 1995.

Rausch O, et al., "Tyrosine 763 of the murine granulocyte colony-stimulating factor receptor mediates Ras-dependent activation of the JNK/SAPK mitogen- activated protein kinase pathway," *Mol. Cell. Biol.*, vol. 17, pp. 1170, 1997.

Reunanen N, et al., "Enhancement of fibroblast cololagenase (matrix metalloproteinase- 1) gene expression by ceramide is mediated by extracellular signal-related and stress-activated protein kinase pathways," *J. Biol. Chem.*, vol. 273, pp. 5137, 1998.

Rincon M, et al., "The JNK pathway regulates the In vivo deletion of immature $CD4^+CD8^{30}$ thymocytes," *J. Exp. Med.*, vol. 188, pp. 1817, 1998.

Roulston A, et al., "Early activation of c-Jun N-terminal kinase and p38 kinase regulate cell survival in response to tumor necrosis factor α," *J. Biol. Chem.*, vol. 273, pp. 10232, 1998.

Ruckdeschel K, et al., "Yersinia enterocolitica promotes deactivation of macrophage mitogen- activated protein kinases extracellular signal-regulated kinase- ½, p38, and c-Jun $NH_2$-terminal kinase," *J. Biol. Chem.*, vol. 272, pp. 15920, 1997.

Saxena M, et al., "Negative regulation of T cell antigen receptor signal transduction by hematopoietic tyrosine phosphatase (HePTP)," *J. Biol. Chem.*, vol. 273, pp. 15340, 1998.

Schinkmann K. Blenis J: Cloning and characterization of a human STE20-like protein kinase with unusual cofactor requirements. *J Biol Chem* 272:28695, 1997.

Schliess F, et al., "Hypersmotic induction of the mitogen-activated protein kinase phosphatase MKP-1 in H411E rat hepatoma cells," *Arch Biochem Biophys*, 351:35, 1998.

Scimeca JC, et al., "Essential role of calcium in the regulation of MAP kinase phosphatase- 1 expression," *Oncogene*, vol. 15, pp. 717, 1997.

Shi ZQ, et al., "The Shp-2 tyrosine phosphatase has opposite effects in mediating the activation of extracellular signal-regulated and c-Jun $NH_2$-terminal mitogen-activated protein kinases," *J. Biol. Chem.*, vol. 273, pp. 4904, 1998.

Shieh JC, et al., "Evidence for a novel MAPKKK-independent pathway controlling the stress activated Sty1/Spc1 MAP kinase in fission yeast," *J. Cell. Sci.*, vol. 111, pp. 2799, 1998.

Shieh JC, et al., "The Win 1 mitotic regulator is a component of the fission yeast stress- activated Sty1 MAPK pathway," *Mol. Biol. Cell.*, vol. 9, pp. 311, 1998.

Skorski T, et al., "The SH3 domain contributes to BCR/ABL-dependent leukemogenesis in vivo: role in adhesion, invasion, and homing," *Blood*, vol. 91, pp. 406, 1998.

Sluss HK, et al., "Embryonic morphogenesis signaling pathway mediated by JNK targets the transcription factor JUN and the TGF-β homologue decapentaplegic," *J. Cell. Biochem.*, vol. 67, pp. 1, 1997.

Smith A, et al., "A role for JNK/SAPK in proliferation, but not apoptosis, of IL-3-dependent cells," *Curr. Biol.*, vol. 7, pp. 893, 1997.

Su YC, et al., "NIK is a new Ste20-related kinase that binds NCK and MEKK1 and activates the SAPK/JNK cascade via a conserved regulatory domain," *EMBO J.*, vol. 16, pp. 1279, 1997.

Sugawara T, et al., "Differential roles of ERK and p38 MAP kinase pathways in positive and negative selection of T lymphocytes," *Immunity*, vol. 9, pp. 565, 1998.

Suzuki K, et al., "Cytokine-Specific Activation of Distinct Mitogen-Activated Protein Kinase Subtype Cascades in Human Neutrophils Stimulated by Granulocyte Colony-Stimulating Factor, Granulocyte-Macrophage Colony-Stimulating Factor, and Tumor Necrosis Factor-α," *Blood*, vol. 93, pp. 341, 1999.

Takahashi K, et al., "Direct binding between two PDZ domain proteins canoe and Zo-1 and their roles in regulation of the jun N-terminal kinase pathway in drosophila morphogenesis," *Mech. Dev.*, vol. 78, pp. 97, 1998.

Takekawa M, et al., "Protein phosphatase 2Cα inhibits the human stress-responsive p38 and JNK MAPK pathways," *EMBO J.*, vol. 17, pp. 4744, 1998.

Takekawa M, et al., "A human homolog of the yeast Ssk2/Ssk22 MAP kinase kinase kinases, TMK1, mediates stress-induced activation of the p38 and JNK pathways," *EMBO J*, vol. 16, pp. 4973, 1997.

Takenaka K, et al., "Activation of the protein kinase p38 in the spindle assembly checkpoint and mitotic arrest," *Science*, vol. 280, pp. 599, 1998.

Terada K, et al., "Ras-dependent activation of c-Jun N-terminal kinase/stress-activated protein kinase in response to interleukin-3 stimulation in hematopoietic BaF3 cells," *J. Biol. Chem.*, vol. 272, pp. 4544, 1997.

Teramoto H, et al., "Tyrosine phosphorylation of the vav proto-oncogene product links FcepsilonRI to the Rac1-JNK pathway," *J. Biol. Chem.*, vol. 272, pp. 10751, 1997.

Thuerauf DJ, et al., "p38 Mitogen-activated protein kinase mediates the transcriptional induction of the atrial natriuretic factor gene through a serum response element A potential role for the transcripton factor ATF6," *J. Biol. Chem.*, vol. 273, pp. 20636, 1998.

Tibbles LA, et al., "MLK-3 activates the SAPK/JNK and p38/RK pathways via SEK1 and MKK3/6," *EMBO J.*, vol. 15, pp. 7026, 1996.

Tobiume K, "Characterization of mouse apoptosis signal-regulating kinase 1," vol. 65, pp. 42, 1998.

Tournier C, et al., "Mitogen-activated protein kinase kinase 7 is an activator of the c-Jun $NH_2$-terminal kinase," *Proc. Natl. Acad. Sci.*, vol. 94, pp. 7337, 1997.

Tournier C, et al., "Mediation by arachidonic acid metabolites of the $H_2O_2$-induced stimulation of mitogen-activated protein kinases (extracellular-signal- regulated kinase and c-Jun $NH_2$-terminal kinase)," *Eur. J. Biochem.*, vol. 244, pp. 587, 1997.

Toyoshima F, et al., "Fas induces cytoplsamic apoptotic responses and activation of the MKK7- JNK/SAPK and MKK6-p38 pathways independent of CPP32-like proteases," *J. Cell. Biol.*, vol. 139, pp. 1005, 1997.

Wang JF, et al., "Signal transduction in human hematopoietic cells by vascular endothelial grown factor related protein, a novel ligand for the FLT4 receptor," *Blood*, vol. 90, pp. 3507, 1997.

Wang W, et al., Activation of the hematopoietic progenitor kinase-1 (HPK1)-dependent, stress-activated c-Jun N-terminal kinase (JNK) pathway by transforming growth factor β (TGF-β)-activated kinase (TAK1), a kinase mediator of TGF β Signal Transduction,: *J. Biol. Chem.*, vol. 272, pp. 22771, 1997.

Wang XS, et al., "Molecular cloning and characterization of a novel p38 mitogen-activated protein kinase," *J. Biol. Chem.*, vol. 272, pp. 23668, 1997.

Wang Y, et al., "Cardiac hypertrophy induced by mitogen-activated protein kinase 7, a specific activator for c-Jun $NH_2$-terminal kinase in ventricular muscle cells," *J. Biol. Chem.*, vol. 273, pp. 5423, 1998.

Werlen G, et al., "Calcineurin preferentially synergizes with PKC-θ to activated JNK and IL-2 promoter in T lymphocytes," *EMBO J.*, vol. 17, pp. 3101, 1998.

Westermarck J, et al., "Enhancement of fibroblast collagenase- 1 (MMP-1) gene expression by tumor promoter okadaic acid is mediated by stress-activated protein kinases Jun N-terminal kinase and p38," *Matrix Biol.*, vol. 17, pp. 547, 1998.

Whitmarsh AJ, et al., "A mammalian scaffold complex that selectively mediates MAP kinase activation," *Science*, vol. 281, pp. 1671, 1998.

Whitmarsh AJ, et al., "Integration of MAP kinase transduction pathways at the serum response element," *Science*, vol. 269, pp. 403, 1995.

Whitmarsh AJ, et al, "Role of p38 and JNK mitogen-activated protein kinases in the activation of ternary complex factors," *Mol. Cell. Biol.*, vol. 17, pp. 2360, 1997.

Wilkinson MG, et al., "The atf1 transcription factor is a target for the Sty1 stress-activated MAP kinase pathway in fission yeast," *Genes & Dev.*, vol. 10, pp. 2289, 1996.

Winter C, et al., "MAP kinase phosphatase 1 is expressed and enhanced by FK506 in surviving mamillary, but not degenerating nigral neurons following axotomy," *Brain Res.*, vol. 801, pp. 198, 1998.

Wisdom R., et al., "c-Jun regulates cell cycle progression and apoptosis by distinct mechanisms," *EMBO J.*, vol. 18, pp. 188, 1999.

Yang DD, et al., "Differentiation of $CD4^+$ T cells to Th1 cells requires MAP kinase JNK2," *Immunity*, vol. 9, pp. 575, 1998.

Yang DD, et al., "Absence of excitotoxicity- induced apoptosis in the hippocampus of mice lacking the Jnk3 gene," *Nature*, vol. 389, pp. 865, 1997.

Yang J, et al., "Molecular cloning and characterization of a human protein kinase that specifically activates c-Jun N-terminal kinase," *Gene*, vol. 212, pp. 95, 1998.

Yao Z, et al., "Activation of stress-activated protein kinases/c-jun N-terminal protein kinases (SAPKs/JNKs) by a novel mitogen-activated protein kinase kinase," *J. Biol. Chem.*, vol. 272, pp. 32378, 1997.

Yeh WC, et al., "Early lethality, functional NF-kappaB activation, and increased sensitivity to TNF-induced cell death in TRAF2-deficient mice," *Immunity*, vol. 7, pp. 715, 1997.

Yuasa T, et al., "Tumor necrosis factor signaling to stress-activated protein kinase (SAPK)/Jun NH2-terminal kinase (JNK) and p38. Germinal center kinase couples TRAF2 to mitogen-activated protein kinase/ERK kinase kinase 1 and SAPK while receptor interacting protein associates with a mitogen-activated protein kinase kinase upstream of MKK6 and p38," *J. Biol. Chem.*, vol. 273, pp. 22681, 1998.

Zanke BW, et al., "Mammalian mitogen-activated protein kinase pathways are regulated through formation of specific kinase-activator complexes," *J. Biol. Chem.*, vol. 271, pp. 29876, 1996.

Zechner D, et al., "MKK6 activates myocardial cell NF-kappaB and inhibits apoptosis in a p38 mitogen-activated protein kinase-dependent manner," *J. Biol. Chem.*, vol. 273, pp. 8232, 1998.

Zechner D, et al., "A role for the p38 mitogen-activated protein kinase pathway in myocardial cell growth, sarcomeric organization, and cardiac-specific gene expression," *J. Cell. Biol.*, vol. 139, pp. 115, 1997.

\* cited by examiner

FIG. 1

```
GGTCTCTGGAGCGCCCTGGGTTGCCCGGCCGGTCCCTGCCGCTGACTTGTTGACACTGCG

AGCACTCAGTCCCTCCCGCGCGCCTCCTCCCCGCCCGCCCCGCCGCTCCTCCTCCCTGTA

ACATGCCATAGTGCGCCTGCGACCACACGGCCGGGGCGCTAGCGTTCGCCTTCAGCCACC

ATGGGGAATGGGATGAACAAGATCCTGCCCGGCCTGTACATCGGCAACTTCAAAGATGCC
 M  G  N  G  M  N  K  I  L  P  G  L  Y  I  G  N  F  K  D  A

AGAGACGCGGAACAATTGAGCAAGAACAAGGTGACACATATTCTGTCTGTCCATGATAGT
 R  D  A  E  Q  L  S  K  N  K  V  T  H  I  L  S  V  H  D  S

GCCAGGCCTATGTTGGAGGGAGTTAAATACCTGTGCATCCCAGCAGCGGATTCACCATCT
 A  R  P  M  L  E  G  V  K  Y  L  C  I  P  A  A  D  S  P  S

CAAAACCTGACAAGACATTTCAAAGAAAGTATTAAATTCATTCACGAGTGCCGGCTCCGC
 Q  N  L  T  R  H  F  K  E  S  I  K  F  I  H  E  C  R  L  R

GGTGAGAGCTGCCTTGTACACTGCCTGGCCGGGGTCTCCAGGAGCGTGACACTGGTGATC
 G  E  S  C  L  V  H  C  L  A  G  V  S  R  S  V  T  L  V  I

GCATACATCATGACCGTCACTGACTTTGGCTGGGAGGATGCCCTGCACACCGTGCGTGCT
 A  Y  I  M  T  V  T  D  F  G  W  E  D  A  L  H  T  V  R  A

GGGAGATCCTGTGCCAACCCCAACGTGGGCTTCCAGAGACAGCTCCAGGAGTTTGAGAAG
 G  R  S  C  A  N  P  N  V  G  F  Q  R  Q  L  Q  E  F  E  K

CATGAGGTCCATCAGTATCGGCAGTGGCTGAAGGAAGAATATGGAGAGAGCCCTTTGCAG
 H  E  V  H  Q  Y  R  Q  W  L  K  E  E  Y  G  E  S  P  L  Q

GATGCAGAAGAAGCCAAAAACATTCTGGGTAAATATAAGGAGCAAGGGCGCACAGAGCCC
 D  A  E  E  A  K  N  I  L  G  K  Y  K  E  Q  G  R  T  E  P

CAGCCCGGCGCCAGGCGGTGGAGCAGTTTTCCGGCACTGGCTCCGCTGACCTACGATAAT
 Q  P  G  A  R  R  W  S  S  F  P  A  L  A  P  L  T  Y  D  N

TATACGACGGAGACCTAACGCAAGCGACCTGCTGCCTTCCTTCCCACTGCTTGTCTTCAG
 Y  T  T  E  T  *  205

TGTGCCCGGCTGGGCAGGGTGCGGTGGTGGTGGCCGATGAGACAGGAAAGGGAGATAGCC

AGGGCGAGGTGGGGCGAGGGCTCTTTCCCCCAAGCAACACCGCCCAGCCTTGTTCCAGGC

CCTTGCACTCCGCCCACCCTACCTGGCTGCACCTGAGCTTGCTGCCCCCGGGGATGTTGC

CCAGTGGCTGTGCACTGCTCTGTGCACGTGCGTGTGTGAGTGCACTTGTGTGTGGGTG

ACTAAGTGGATGCATGTGTGTGCCTGTGTGAGTGAGGGTATGTGCACCTAAGTGTGTACA

TGTGTGTATGTTGTGAAAGTGTCTGTGCACATGAATGTTTGTGTGAGTGTGAACTCTTTC

TTACTGCTGGAAGTCACA   1218
```

FIG.2

```
AGCCCGGCGCGGCCATGGGGAGTGGGATGAGCCAGATCCTGCCGGGCCTGTACATTGGCA
              M  G  S  G  M  S  Q  I  L  P  G  L  Y  I  G  N
ACTTCAAAGACGCAAGAGATGCAGAACAGTTGAGCAGGAACAAGGTGACACACATTCTTT
 F  K  D  A  R  D  A  E  Q  L  S  R  N  K  V  T  H  I  L ·S
CTGTGCACGATACTGCCAGGCCCATGTTGGAGGGAGTTAAATACCTGTGTATTCCAGCGG
 V  H  D  T  A  R  P  M  L  E  G  V  K  Y  L  C  I  P  A  A
CAGACACACCATCTCAAAACCTGACAAGACATTTCAAAGAAAGCATTAAATTCATTCATG
 D  T  P  S  Q  N  L  T  R  H  F  K  E  S  I  K  F  I  H  E
AGTGCCGACTCCAGGGTGAGAGCTGTCTTGTACATTGCCTGGCTGGGGTCTCCAGGAGTG
    C  R  L  Q  G  E  S  C  L  V  H  C  L  A  G  V  S  R  S  V
TGACATTGGTGATCGCATACATCACGACTGTCACCGACTTTGGCTGGGAAGATGCCTTGC
 T  L  V  I  A  Y  I  T  T  V  T  D  F  G  W  E  D  A  L  H
ACACTGTTCGTGCGGGGAGGTCCTGTGCCAACCCCAACCTGGGCTTTCAAAGGCAGCCGC
    T  V  R  A  G  R  S  C  A  N  P  N  L  G  F  Q  R  Q  P  Q
AGGAGTTTGAGAAACATGAAGTGCACCAGTATCGGCAATGGCTGAGAGAAGAGTATGGAG
    E  F  E  K  H  E  V  H  Q  Y  R  Q  W  L  R  E  E  Y  G  E
AGAACCCTTTGCGGGATGCAGAAGAAGCCAAAAATATTCTGGGTAAATATAAAGAGCAAG
    N  P  L  R  D  A  E  E  A  K  N  I  L  G  K  Y  K  E  Q  G
GGCGCATGGAGCCCCGGCCTAGCAGCAGGCGGTGGAGCAGCTTCTCAACCCTGCCTCCTC
    R  M  E  P  R  P  S  S  R  R  W  S  S  F  S  T  L  P  P  L
TCACCTACAATAACTACACAACAGAGACCTAACAGAGAGAGCTGGTGTCTGCCTTCCTGC
    T  Y  N  N  Y  T  T  E  T  *    205
TGCGGGTCTTCTGGGTTGCCTACCATGTGCTGGTGTGCCTGGTGTGCTGGCTCCTGCCTC
TGAGGACTACGAGAGGAGGTCGCAGCAAGGTGGAGCACTCAGGGCTCCTTCTCAGAATAC
CGCCCTACTCAGGCTTTTTCACTCTCCCATCTTCGCCCCATCTTTTCCTCACCTGAACTT
GCCCAACCTGGGATGCTGCCCGGCCACCGTGTACTTCTCGTATGTGTGCAGGCGTGTGGA
TGTGCATGTATGTGTCTAAGAGTGTGCATATATACCTACAAATGTATGCATTGTGAACAA
GTACACATGTAAATGTGTCTCTGCATGTGGGCACTGAGTGTTTATGGTGCTGAAAGTTAT
AAACACCCGCTGCCAGAACTGCAATGGTCACATTGTTCAATCCCACATGGAAGTCATTTG
AACTTGGCCTCCTGGAAAGCTACTCCACCAAGTACAGCTTATGCCTGTGCTGAGTGAGAG
CTCAGGGTGTGGGCAGCTGGAAACAGTGGTGTTCCAGATTCTGAGATGGCACAGAGGAAG
GGACAGGACCCTCCTGAGGAAGAGTGGCATAATCCTAGTGAGTTTTATGTCTGTGGGAAC
AAGGGAGGGGCTTTCTGAGCACTGTCTTGGACTTGATAAGTATACTTGCCAGCCCGTCAT
GGCCCTGAGTTCCACTGGTGCCTGCTCTGCGTGGGACCAGCGTCATTTGACTTTCATGGT
GATATGGTATGGTGACAGGGTGGACCTGAGACTCAGTAGGCCTATACCAGAGGTCTGGCC
CACTCCTGTCTGCTTTTAAACACTTTAGCTCTGGCTTAGCTCTTGTTGCAGGGGTCTCAT
CTCAGGTTTGCATGTACCTGCAGGAACTGGAAAGAAAGGCAGTTATTAAACTCCATAGCC
ATTTGTGATTTAAAATGCCTACGCATTCACTGAGCTCACTGTTGTATGCTGTGGATTTGA
CCGCTACCTCATGAAGTTCTTCCTTCCTTCCTTCCTTCCTTCCTTCCTTCCTTCCTTCCT
TCCTTCCTTTCTTTCTTCTTTAAGGTTGAGGTTTCTTTGGTACCCCAGTCAACTCTGCTT
CATAGTTGAGAATGTTTGTCATGTGACTATTGTTTTTGAAACCAAAGAGAAGAGCATACT
TATGTCATTGAGTGATTTAAAATTTGCAGCTTGGCTTCTGTAGGGTTTTCTAGTGAGTCA
AACCTACATTCTGACCATGAGAGTCCTTAGTTCAAAGTATGTGGCAGCAGGCACCCCTAG
AAGTTTTGCACAGTCCAGTGTCCAGTCCTTTATGCCAATTCACGTTGCTTAAGCATGCAG
GACCATGCAAATGAAAAATACACTCAACCTCTCCCTAAACGTACTGTGACCAGGCATCTC
TGAAGCTTAAGAAACCCCCAAGAAGCCCCGAGGAGCTGGACAGTGGTGGCACACACCTT
TAATCCCAGCTTTTGGGAGGCAGAGGCAGGCGGATTTCTGAGTTCAAGGCCAGCCTGGTC
TACAGAGTGAGTTCCAGGACAGCCAGGGCTACACAGAGAAACCCTGTCCCGAAAAACCAA
AAAAAAAAAAAAAAAAAGGAGAAGCCCCTGAGGAAGAAGCAGCAGGCCTCTCTCTGTGT
GTGTGGAGCTCTCAGGGACCCAGGGAAGGTGTGGTTGCCAGCTCTCTGTGTGCAGGCCGT
GCCAAGCAATAGCATGAGTGACGCCTGAGTACCTGAGTATGTGTGCACGTGTATGAACAG
CTGCATACCTTTCCATAGGTTCTCAACTGTCTCAATTTTTGTTGCCAGTAATGTTCTTTC
TCCACAGCTGCTCCGGGAATTCTGAAGTACTGGGCCTTTCTCAGAAGACTGTAATGTACC
TGAAGTTTCTGAAATATTGCAAAGTTCAGGCTGGTGCTGCCAAAAAGAAAAGTGATGTAA
AGTTTATTTTTAAGAATCCAATAGTGATTTGTATACTTGTTTTTTTTTCATTTTAAACCA
AATGCATGTATAATCATGTGGGAATATGTTAAGATCTATGGATATTCTGTAGCAAGAGAA
ATATCTTTGCCTTAACTCCACTGCTGTGGTTGTTCCTTGGACCTGACCGATGCTCATACA
ATAATCTCAAGAGCCCTGTCTGTTTCGTAATAGTAACTACTTCTCATGAACACTACCCAA
GGAGGAAGCCTGCACCTGGGAAGTGTGCAGTGTGAGCTCTGCCCTCCTGTTAAGTTCTCC
AGCTCTAGACATGTCTCTGGGTGTGTGTTTTATCTACTGGTGTTATTCTATATGGTAGAA
TTACCAAAAGCTATTCAGATTTCTTAATAAAGGGCAAATCCCGGAATCTTTTGNTTTTTA
CCCTGGAAGA    3010
```

FIG. 3(a)

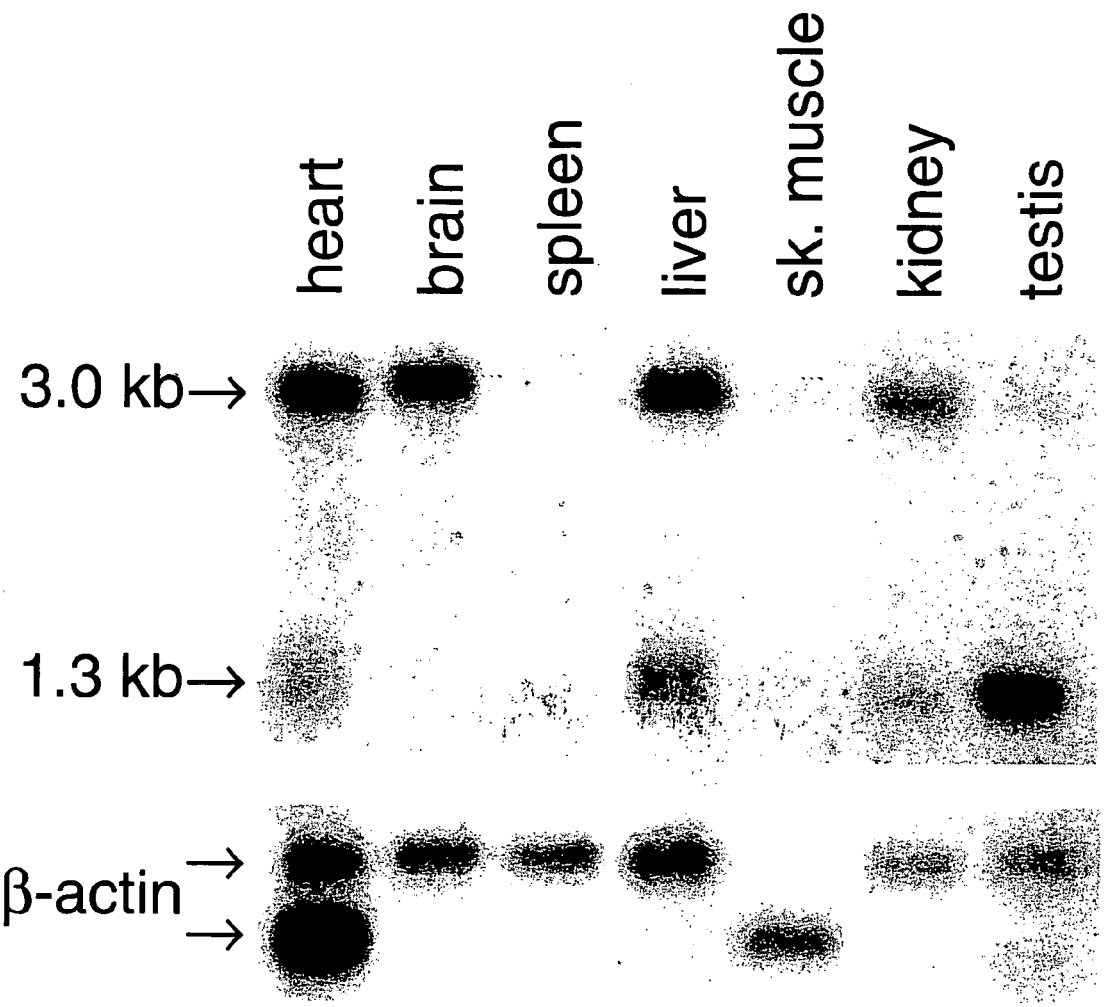

FIG.4
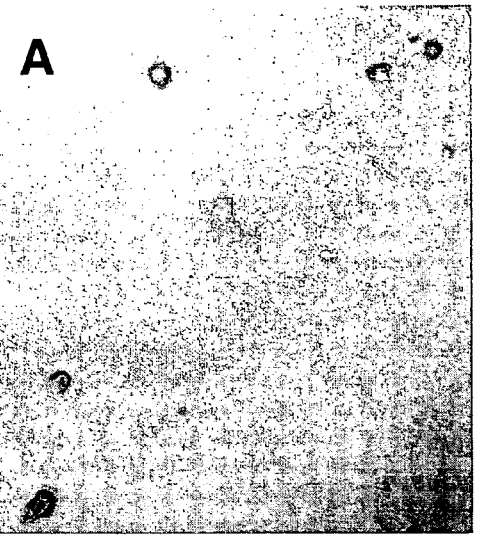
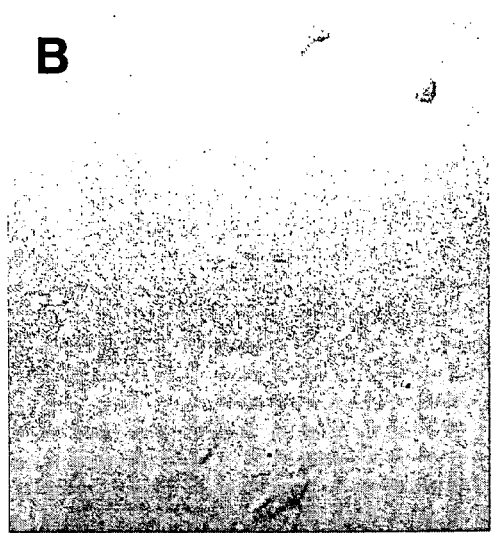
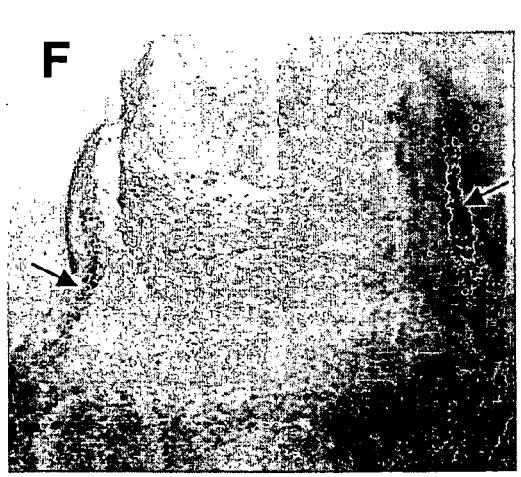

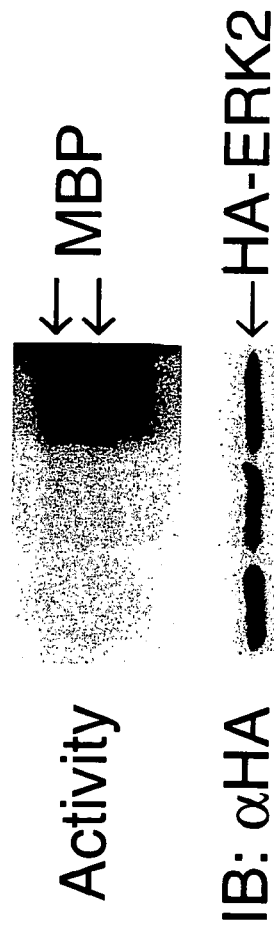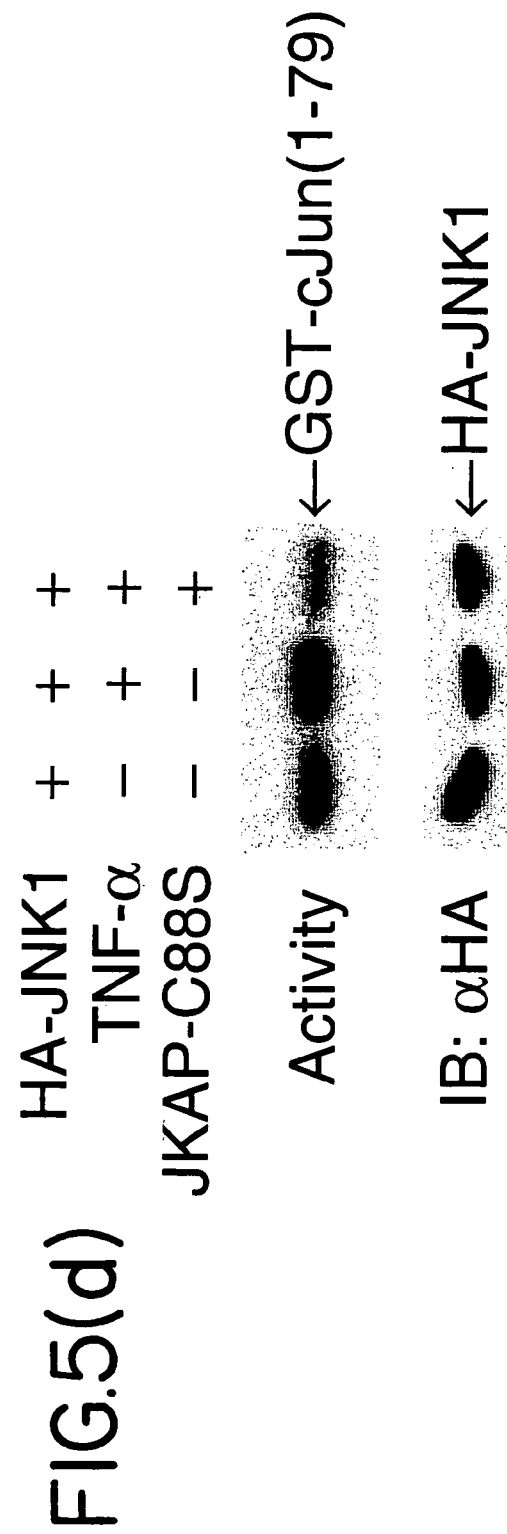
FIG.5(c)
FIG.5(d)

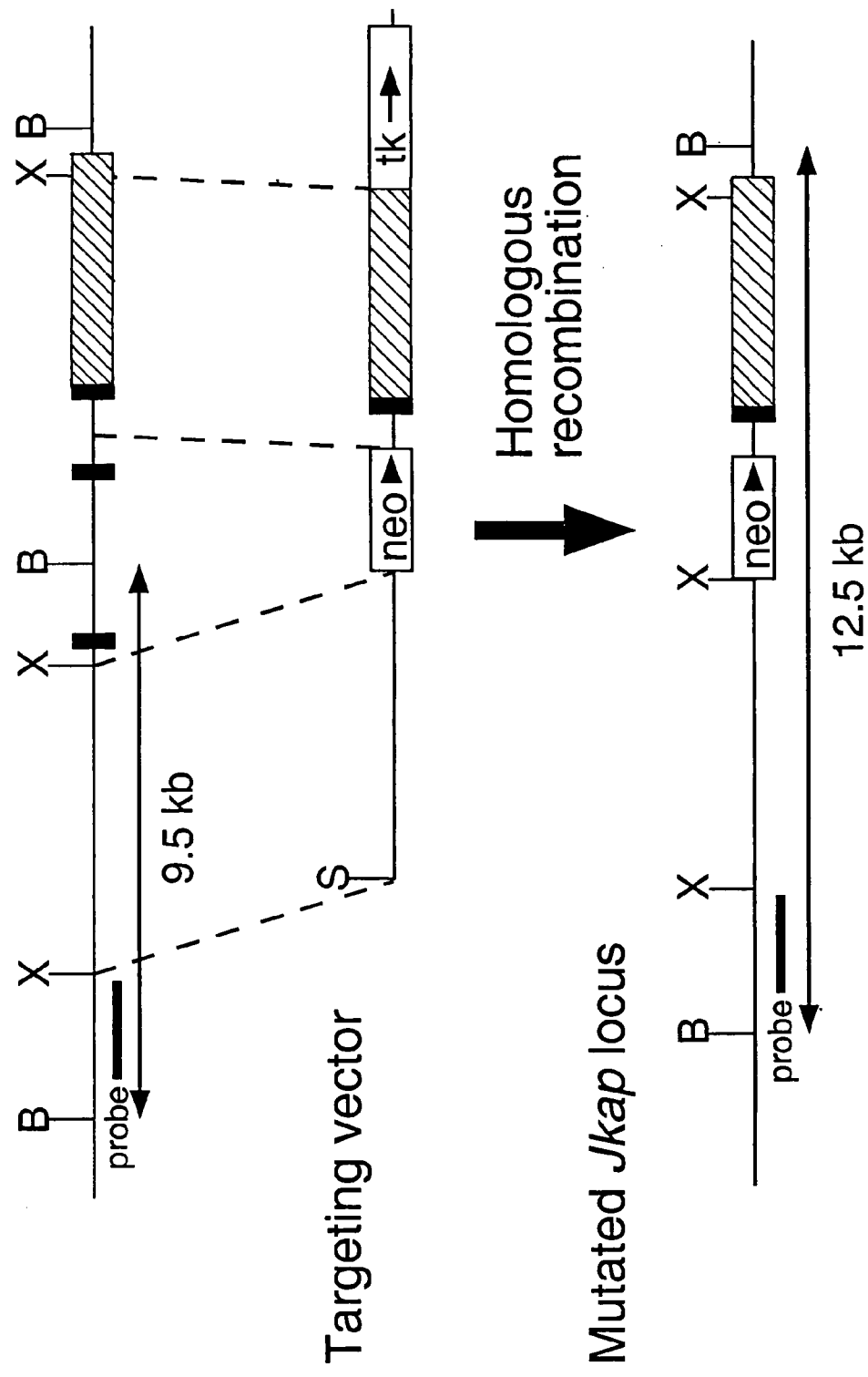

FIG.6(b)
FIG.6(c)
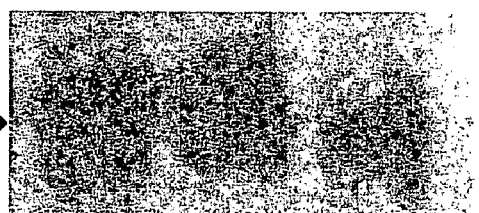

SEQUENCE LISTING

```
<160> NUMBER OF SEQ ID NOS: 27

<210> SEQ ID NO 1
<211> LENGTH: 1218
<212> TYPE: DNA
<213> ORGANISM: Homo sapiens
<220> FEATURE:
<221> NAME/KEY: CDS
<222> LOCATION: (181)..(795)

<400> SEQUENCE: 1
ggtctctgga gcgccctggg ttgcccggcc ggtccctgcc gctgacttgt tgacactgcg        60
agcactcagt ccctcccgcg cgcctcctcc ccgcccgccc cgccgctcct cctccctgta      120
acatgccata gtgcgcctgc gaccacacgg ccggggcgct agcgttcgcc ttcagccacc      180 atg ggg aat ggg atg aac aag atc ctg ccc ggc ctg tac atc ggc aac      228
Met Gly Asn Gly Met Asn Lys Ile Leu Pro Gly Leu Tyr Ile Gly Asn
1               5                   10                  15 ttc aaa gat gcc aga gac gcg gaa caa ttg agc aag aac aag gtg aca      276
Phe Lys Asp Ala Arg Asp Ala Glu Gln Leu Ser Lys Asn Lys Val Thr
```

```
                      20                  25                  30
cat att ctg tct gtc cat gat agt gcc agg cct atg ttg gag gga gtt         324
His Ile Leu Ser Val His Asp Ser Ala Arg Pro Met Leu Glu Gly Val
                35                  40                  45 aaa tac ctg tgc atc cca gca gcg gat tca cca tct caa aac ctg aca         372
Lys Tyr Leu Cys Ile Pro Ala Ala Asp Ser Pro Ser Gln Asn Leu Thr
     50                  55                  60 aga cat ttc aaa gaa agt att aaa ttc att cac gag tgc cgg ctc cgc         420
Arg His Phe Lys Glu Ser Ile Lys Phe Ile His Glu Cys Arg Leu Arg
 65                  70                  75                  80 ggt gag agc tgc ctt gta cac tgc ctg gcc ggg gtc tcc agg agc gtg         468
Gly Glu Ser Cys Leu Val His Cys Leu Ala Gly Val Ser Arg Ser Val
                 85                  90                  95 aca ctg gtg atc gca tac atc atg acc gtc act gac ttt ggc tgg gag         516
Thr Leu Val Ile Ala Tyr Ile Met Thr Val Thr Asp Phe Gly Trp Glu
                100                 105                 110 gat gcc ctg cac acc gtg cgt gct ggg aga tcc tgt gcc aac ccc aac         564
Asp Ala Leu His Thr Val Arg Ala Gly Arg Ser Cys Ala Asn Pro Asn
            115                 120                 125 gtg ggc ttc cag aga cag ctc cag gag ttt gag aag cat gag gtc cat         612
Val Gly Phe Gln Arg Gln Leu Gln Glu Phe Glu Lys His Glu Val His
        130                 135                 140 cag tat cgg cag tgg ctg aag gaa gaa tat gga gag agc cct ttg cag         660
Gln Tyr Arg Gln Trp Leu Lys Glu Glu Tyr Gly Glu Ser Pro Leu Gln
145                 150                 155                 160 gat gca gaa gaa gcc aaa aac att ctg ggt aaa tat aag gag caa ggg         708
Asp Ala Glu Glu Ala Lys Asn Ile Leu Gly Lys Tyr Lys Glu Gln Gly
                165                 170                 175 cgc aca gag ccc cag ccc ggc gcc agg cgg tgg agc agt ttt ccg gca         756
Arg Thr Glu Pro Gln Pro Gly Ala Arg Arg Trp Ser Ser Phe Pro Ala
            180                 185                 190 ctg gct ccg ctg acc tac gat aat tat acg acg gag acc taacgcaagc         805
Leu Ala Pro Leu Thr Tyr Asp Asn Tyr Thr Thr Glu Thr
        195                 200                 205 gacctgctgc cttccttccc actgcttgtc ttcagtgtgc ccggctgggc agggtgcggt       865
ggtggtggcc gatgagacag gaaagggaga tagccagggc gaggtggggc gagggctctt       925
tcccccaagc aacaccgccc agccttgttc caggccttg cactccgccc acccctacctg       985 gctgcacctg agcttgctgc ccccggggat gttgcccagt ggctgtgcac tgctctgtgc      1045
acgtgcgtgt gtgtgagtgc acttgtgtgt gggtgactaa gtggatgcat gtgtgtgcct      1105
gtgtgagtga gggtatgtgc acctaagtgt gtacatgtgt gtatgttgtg aaagtgtctg      1165
tgcacatgaa tgtttgtgtg agtgtgaact ctttcttact gctggaagtc aca             1218

<210> SEQ ID NO 2
<211> LENGTH: 205
<212> TYPE: PRT
<213> ORGANISM: Homo sapiens

<400> SEQUENCE: 2

Met Gly Asn Gly Met Asn Lys Ile Leu Pro Gly Leu Tyr Ile Gly Asn
 1               5                  10                  15

Phe Lys Asp Ala Arg Asp Ala Glu Gln Leu Ser Lys Asn Lys Val Thr
                20                  25                  30

His Ile Leu Ser Val His Asp Ser Ala Arg Pro Met Leu Glu Gly Val
            35                  40                  45

Lys Tyr Leu Cys Ile Pro Ala Ala Asp Ser Pro Ser Gln Asn Leu Thr
        50                  55                  60
```

-continued

```
Arg His Phe Lys Glu Ser Ile Lys Phe Ile His Glu Cys Arg Leu Arg
 65                  70                  75                  80

Gly Glu Ser Cys Leu Val His Cys Leu Ala Gly Val Ser Arg Ser Val
                 85                  90                  95

Thr Leu Val Ile Ala Tyr Ile Met Thr Val Thr Asp Phe Gly Trp Glu
            100                 105                 110

Asp Ala Leu His Thr Val Arg Ala Gly Arg Ser Cys Ala Asn Pro Asn
        115                 120                 125

Val Gly Phe Gln Arg Gln Leu Gln Glu Phe Glu Lys His Glu Val His
    130                 135                 140

Gln Tyr Arg Gln Trp Leu Lys Glu Tyr Gly Glu Ser Pro Leu Gln
145                 150                 155                 160

Asp Ala Glu Glu Ala Lys Asn Ile Leu Gly Lys Tyr Lys Glu Gln Gly
                165                 170                 175

Arg Thr Glu Pro Gln Pro Gly Ala Arg Arg Trp Ser Ser Phe Pro Ala
            180                 185                 190

Leu Ala Pro Leu Thr Tyr Asp Asn Tyr Thr Thr Glu Thr
        195                 200                 205

<210> SEQ ID NO 3
<211> LENGTH: 3010
<212> TYPE: DNA
<213> ORGANISM: Mus musculus
<220> FEATURE:
<221> NAME/KEY: CDS
<222> LOCATION: (15)..(629)
<223> OTHER INFORMATION: n is a, t, c, or g

<400> SEQUENCE: 3
agcccggcgc ggcc atg ggg agt ggg atg agc cag atc ctg ccg ggc ctg        50
               Met Gly Ser Gly Met Ser Gln Ile Leu Pro Gly Leu
                 1               5                  10 tac att ggc aac ttc aaa gac gca aga gat gca gaa cag ttg agc agg        98
Tyr Ile Gly Asn Phe Lys Asp Ala Arg Asp Ala Glu Gln Leu Ser Arg
         15                  20                  25 aac aag gtg aca cac att ctt tct gtg cac gat act gcc agg ccc atg       146
Asn Lys Val Thr His Ile Leu Ser Val His Asp Thr Ala Arg Pro Met
     30                  35                  40 ttg gag gga gtt aaa tac ctg tgt att cca gcg gca gac aca cca tct       194
Leu Glu Gly Val Lys Tyr Leu Cys Ile Pro Ala Ala Asp Thr Pro Ser
 45                  50                  55                  60 caa aac ctg aca aga cat ttc aaa gaa agc att aaa ttc att cat gag       242
Gln Asn Leu Thr Arg His Phe Lys Glu Ser Ile Lys Phe Ile His Glu
                 65                  70                  75 tgc cga ctc cag ggt gag agc tgt ctt gta cat tgc ctg gct ggg gtc       290
Cys Arg Leu Gln Gly Glu Ser Cys Leu Val His Cys Leu Ala Gly Val
             80                  85                  90 tcc agg agt gtg aca ttg gtg atc gca tac atc acg act gtc acc gac       338
Ser Arg Ser Val Thr Leu Val Ile Ala Tyr Ile Thr Thr Val Thr Asp
         95                 100                 105 ttt ggc tgg gaa gat gcc ttg cac act gtt cgt gcg ggg agg tcc tgt       386
Phe Gly Trp Glu Asp Ala Leu His Thr Val Arg Ala Gly Arg Ser Cys
    110                 115                 120 gcc aac ccc aac ctg ggc ttt caa agg cag ccg cag gag ttt gag aaa       434
Ala Asn Pro Asn Leu Gly Phe Gln Arg Gln Pro Gln Glu Phe Glu Lys
125                 130                 135                 140 cat gaa gtg cac cag tat cgg caa tgg ctg aga gaa gag tat gga gag       482
His Glu Val His Gln Tyr Arg Gln Trp Leu Arg Glu Glu Tyr Gly Glu
                145                 150                 155
```

```
aac cct ttg cgg gat gca gaa gaa gcc aaa aat att ctg ggt aaa tat    530
Asn Pro Leu Arg Asp Ala Glu Glu Ala Lys Asn Ile Leu Gly Lys Tyr
        160                 165                 170 aaa gag caa ggg cgc atg gag ccc cgg cct agc agc agg cgg tgg agc    578
Lys Glu Gln Gly Arg Met Glu Pro Arg Pro Ser Ser Arg Arg Trp Ser
        175                 180                 185 agc ttc tca acc ctg cct cct ctc acc tac aat aac tac aca aca gag    626
Ser Phe Ser Thr Leu Pro Pro Leu Thr Tyr Asn Asn Tyr Thr Thr Glu
        190                 195                 200 acc taacagagag agctggtgtc tgccttcctg ctgcgggtct tctgggttgc         679
Thr
205 ctaccatgtg ctggtgtgcc tggtgtgctg gctcctgcct ctgaggacta cgagaggagg  739 tcgcagcaag gtggagcact cagggctcct tctcagaata ccgccctact caggctttt   799 cactctccca tcttcgcccc atctttcct cacctgaact tgcccaacct gggatgctgc   859 ccggccaccg tgtacttctc gtatgtgtgc aggcgtgtgg atgtgcatgt atgtgtctaa  919 gagtgtgcat atatacctac aaatgtatgc attgtgaaca agtacacatg taaatgtgtc  979 tctgcatgtg ggcactgagt gtttatggtg ctgaaagtta taaacacccg ctgccagaac  1039 tgcaatggtc acattgttca atcccacatg aagtcattt gaacttggcc tcctggaaag   1099 ctactccacc aagtacagct tatgcctgtg ctgagtgaga gctcagggtg tgggcagctg  1159 gaaacagtgg tgttccagat tctgagatgg cacagaggaa gggacaggac cctcctgagg  1219 aagagtggca taatcctagt gagttttatg tctgtgggaa caagggaggg gctttctgag  1279 cactgtcttg gacttgataa gtatacttgc cagcccgtca tggccctgag ttccactggt  1339 gcctgctctg cgtgggacca gcgtcatttg actttcatgg tgatatggta tggtgacagg  1399 gtggacctga gactcagtag gcctatacca gaggtctggc ccactcctgt ctgcttttaa  1459 acactttagc tctggcttag ctcttgttgc aggggtctca tctcaggttt gcatgtacct  1519 gcaggaactg gaaagaaagg cagttattaa actccatagc catttgtgat ttaaaatgcc  1579 tacgcattca ctgagctcac tgttgtatgc tgtggatttg accgctacct catgaagttc  1639 ttccttcctt ccttccttcc ttccttcctt ccttccttcc ttccttcctt tctttcttct  1699 ttaaggttga ggtttctttg gtaccccagt caactctgct tcatagttga aatgttttgt  1759 catgtgacta ttgttttttga aaccaaagag aagagcatac ttatgtcatt gagtgattta  1819 aaatttgcag cttggcttct gtaggttttt ctagtgagtc aaacctacat tctgaccatg  1879 agagtcctta gttcaaagta tgtggcagca ggcacccta gaagttttgc acagtccagt   1939 gtccagtcct ttatgccaat tcacgttgct taagcatgca ggaccatgca aatgaaaaat  1999 acactcaacc tctccctaaa cgtactgtga ccaggcatct ctgaagctta agaaaccccc  2059 aagaagcccc cgaggagctg gacagtggtg cacacacctt taatcccag cttttgggag   2119 gcagaggcag gcggatttct gagttcaagg ccagcctggt ctacagagtg agttccagga  2179 cagccagggc tacacagaga aaccctgtcc cgaaaaacca aaaaaaaaa aaaaaaaaag   2239 gagaagcccc tgaggaagaa gcagcaggcc tctctctgtg tgtgtggagc tctcagggac  2299 ccagggaagg tgtggttgcc agctctctgt gtgcaggccg tgccaagcaa tagcatgagt  2359 gacgcctgag tacctgagta tgtgtgcacg tgtatgaaca gctgcatacc tttccatagg  2419 ttctcaactg tctcaatttt tgttgccagt aatgttcttt ctccacagct gctccgggaa  2479 ttctgaagta ctgggccttt ctcagaagac tgtaatgtac ctgaagtttc tgaaatattg  2539
```

```
caaagttcag gctggtgctg ccaaaaagaa aagtgatgta aagtttattt ttaagaatcc      2599
aatagtgatt tgtatacttg ttttttttttc attttaaacc aaatgcatgt ataatcatgt    2659
gggaatatgt taagatctat ggatattctg tagcaagaga aatatctttg ccttaactcc     2719
actgctgtgg ttgttccttg gacctgaccg atgctcatac aataatctca agagccctgt    2779
ctgtttcgta atagtaacta cttctcatga acactaccca aggaggaagc ctgcacctgg    2839
gaagtgtgca gtgtgagctc tgccctcctg ttaagttctc cagctctaga catgtctctg    2899
ggtgtgtgtt ttatctactg gtgttattct atatggtaga attaccaaaa gctattcaga    2959
tttcttaata aagggcaaat cccggaatct tttgnttttt accctggaag a            3010
```

<210> SEQ ID NO 4
<211> LENGTH: 205
<212> TYPE: PRT
<213> ORGANISM: Mus musculus

<400> SEQUENCE: 4

```
Met Gly Ser Gly Met Ser Gln Ile Leu Pro Gly Leu Tyr Ile Gly Asn
1               5                   10                  15

Phe Lys Asp Ala Arg Asp Ala Glu Gln Leu Ser Arg Asn Lys Val Thr
            20                  25                  30

His Ile Leu Ser Val His Asp Thr Ala Arg Pro Met Leu Glu Gly Val
        35                  40                  45

Lys Tyr Leu Cys Ile Pro Ala Ala Asp Thr Pro Ser Gln Asn Leu Thr
    50                  55                  60

Arg His Phe Lys Glu Ser Ile Lys Phe Ile His Glu Cys Arg Leu Gln
65                  70                  75                  80

Gly Glu Ser Cys Leu Val His Cys Leu Ala Gly Val Ser Arg Ser Val
                85                  90                  95

Thr Leu Val Ile Ala Tyr Ile Thr Thr Val Thr Asp Phe Gly Trp Glu
            100                 105                 110

Asp Ala Leu His Thr Val Arg Ala Gly Arg Ser Cys Ala Asn Pro Asn
        115                 120                 125

Leu Gly Phe Gln Arg Gln Pro Gln Glu Phe Glu Lys His Glu Val His
    130                 135                 140

Gln Tyr Arg Gln Trp Leu Arg Glu Glu Tyr Gly Glu Asn Pro Leu Arg
145                 150                 155                 160

Asp Ala Glu Glu Ala Lys Asn Ile Leu Gly Lys Tyr Lys Glu Gln Gly
                165                 170                 175

Arg Met Glu Pro Arg Pro Ser Ser Arg Arg Trp Ser Phe Ser Thr
            180                 185                 190

Leu Pro Pro Leu Thr Tyr Asn Asn Tyr Thr Thr Glu Thr
        195                 200                 205
```

<210> SEQ ID NO 5
<211> LENGTH: 138
<212> TYPE: PRT
<213> ORGANISM: Artificial
<220> FEATURE:
<223> OTHER INFORMATION: Description of Artificial Sequence: mJKAP

<400> SEQUENCE: 5

```
Met Ser Gln Ile Leu Pro Gly Leu Tyr Ile Gly Asn Phe Lys Asp Ala
1               5                   10                  15

Arg Asp Ala Glu Gln Leu Ser Arg Asn Lys Val Thr His Ile Leu Ser
            20                  25                  30
```

Val His Asp Thr Ala Arg Pro Met Leu Glu Gly Val Lys Tyr Leu Cys
             35                  40                  45

Ile Pro Ala Ala Asp Thr Pro Ser Gln Asn Leu Thr Arg His Phe Lys
 50                  55                  60

Glu Ser Ile Lys Phe Ile His Glu Cys Arg Leu Gln Gly Glu Ser Cys
 65                  70                  75                  80

Leu Val His Cys Leu Ala Gly Val Ser Arg Ser Val Thr Leu Val Ile
                 85                  90                  95

Ala Tyr Ile Thr Thr Val Thr Asp Phe Gly Trp Glu Asp Ala Leu His
             100                 105                 110

Thr Val Arg Ala Gly Arg Ser Cys Ala Asn Pro Asn Leu Gly Phe Gln
             115                 120                 125

Arg Gln Pro Gln Glu Phe Glu Lys His Glu
         130                 135

<210> SEQ ID NO 6
<211> LENGTH: 137
<212> TYPE: PRT
<213> ORGANISM: Artificial
<220> FEATURE:
<223> OTHER INFORMATION: Description of Artificial sequence: puckered

<400> SEQUENCE: 6

Ala Ser Pro Val Phe Pro His Leu Leu Leu Gly Asn Gly Arg Asp Ala
 1               5                  10                  15

Asp Asn Pro Ser Ser Val Gly Ala Asn Cys Val Leu Asn Val Thr Cys
             20                  25                  30

Gln Ser Pro Asn Glu Ser His Leu Gln Gly Leu Lys Tyr Met Gln Ile
         35                  40                  45

Pro Ala Ser Asp Thr Pro His Gln Asn Ile Lys Gln Tyr Phe Gln Glu
 50                  55                  60

Ala Tyr Asp Phe Ile Glu Asp Ala Arg Lys Thr Gly Ser Arg Val Leu
 65                  70                  75                  80

Leu His Cys His Ala Gly Ile Ser Arg Ser Ala Thr Ile Ala Ile Ala
                 85                  90                  95

Tyr Val Met Arg Tyr Lys Ser Leu Ser Leu Leu Glu Ala Tyr Lys Leu
             100                 105                 110

Val Lys Val Ala Arg Pro Ile Ile Ser Pro Asn Leu Asn Phe Met Gly
             115                 120                 125

Gln Leu Leu Glu Leu Glu Gln Asn Leu
         130                 135

<210> SEQ ID NO 7
<211> LENGTH: 141
<212> TYPE: PRT
<213> ORGANISM: Artificial
<220> FEATURE:
<223> OTHER INFORMATION: Description of Artificial Sequence: rMKP-3

<400> SEQUENCE: 7

Pro Val Glu Ile Leu Pro Phe Leu Tyr Leu Gly Cys Ala Lys Asp Ser
 1               5                  10                  15

Thr Asn Leu Asp Val Leu Glu Glu Phe Gly Ile Lys Tyr Ile Leu Asn
             20                  25                  30

Val Thr Pro Asn Leu Pro Asn Leu Phe Glu Asn Ala Gly Glu Phe Lys
         35                  40                  45

Tyr Lys Gln Ile Pro Ile Ser Asp His Trp Ser Gln Asn Leu Ser Gln
 50                  55                  60

```
Phe Phe Pro Glu Ala Ile Ser Phe Ile Asp Glu Ala Arg Gly Lys Asn
 65                  70                  75                  80

Cys Gly Val Leu Val His Cys Leu Ala Gly Ile Ser Arg Ser Val Thr
                 85                  90                  95

Val Thr Val Ala Tyr Leu Met Gln Lys Leu Asn Leu Ser Met Asn Asp
            100                 105                 110

Ala Tyr Asp Ile Val Lys Met Lys Ser Asn Ile Ser Pro Asn Phe
        115                 120                 125

Asn Phe Met Gly Gln Leu Leu Asp Phe Glu Arg Thr Leu
    130                 135                 140

<210> SEQ ID NO 8
<211> LENGTH: 141
<212> TYPE: PRT
<213> ORGANISM: Artificial
<220> FEATURE:
<223> OTHER INFORMATION: Description of Artificial Sequence: rMKP-X

<400> SEQUENCE: 8

Pro Val Gln Ile Leu Pro Tyr Leu Tyr Leu Gly Cys Ala Lys Asp Ser
  1               5                  10                  15

Thr Asn Leu Asp Val Leu Gly Lys Tyr Gly Ile Lys Tyr Ile Leu Asn
             20                  25                  30

Val Thr Pro Asn Leu Pro Asn Ala Phe Glu His Gly Gly Glu Phe Thr
         35                  40                  45

Tyr Lys Gln Ile Pro Ile Ser Asp His Trp Ser Gln Asn Leu Ser Gln
     50                  55                  60

Phe Phe Pro Glu Ala Ile Ser Phe Ile Asp Glu Ala Arg Ser Lys Lys
 65                  70                  75                  80

Cys Gly Val Leu Val His Cys Leu Ala Gly Ile Ser Arg Ser Val Thr
                 85                  90                  95

Val Thr Val Ala Tyr Leu Met Gln Lys Met Asn Leu Ser Leu Asn Asp
            100                 105                 110

Ala Tyr Asp Phe Val Lys Arg Lys Lys Ser Asn Ile Ser Pro Asn Phe
        115                 120                 125

Asn Phe Met Gly Gln Leu Leu Asp Phe Glu Arg Thr Leu
    130                 135                 140

<210> SEQ ID NO 9
<211> LENGTH: 141
<212> TYPE: PRT
<213> ORGANISM: Artificial
<220> FEATURE:
<223> OTHER INFORMATION: Description of Artificial Sequence: hMKP-4

<400> SEQUENCE: 9

Pro Val Gln Ile Leu Pro Asn Leu Tyr Leu Gly Ser Ala Arg Asp Ser
  1               5                  10                  15

Ala Asn Leu Glu Ser Leu Ala Lys Leu Gly Ile Arg Tyr Ile Leu Asn
             20                  25                  30

Val Thr Pro Asn Leu Pro Asn Phe Phe Glu Lys Asn Gly Asp Phe His
         35                  40                  45

Tyr Lys Gln Ile Pro Ile Ser Asp His Trp Ser Gln Asn Leu Ser Arg
     50                  55                  60

Phe Phe Pro Glu Ala Ile Glu Phe Ile Asp Glu Ala Leu Ser Gln Asn
 65                  70                  75                  80

Cys Gly Val Leu Val His Cys Leu Ala Gly Val Ser Arg Ser Val Thr
```

-continued

```
                    85                  90                  95
Val Thr Val Ala Tyr Leu Met Gln Lys Leu His Leu Ser Leu Asn Asp
                100                 105                 110

Ala Tyr Asp Leu Val Lys Arg Lys Lys Ser Asn Ile Ser Pro Asn Phe
            115                 120                 125

Asn Phe Met Gly Gln Leu Leu Asp Phe Glu Arg Ser Leu
        130                 135                 140

<210> SEQ ID NO 10
<211> LENGTH: 139
<212> TYPE: PRT
<213> ORGANISM: Artificial
<220> FEATURE:
<223> OTHER INFORMATION: Description of Artificial Sequence: rMKP-2

<400> SEQUENCE: 10

Pro Val Glu Ile Leu Pro Phe Leu Tyr Leu Gly Ser Ala Tyr His Ala
1               5                   10                  15

Ala Arg Arg Asp Met Leu Asp Ala Leu Gly Ile Thr Ala Leu Leu Asn
                20                  25                  30

Val Ser Ser Asp Cys Pro Asn His Phe Glu Gly His Tyr Gln Tyr Lys
            35                  40                  45

Cys Ile Pro Val Glu Asp Asn His Lys Ala Asp Ile Ser Ser Trp Phe
    50                  55                  60

Met Glu Ala Ile Glu Tyr Ile Asp Ala Val Lys Asp Cys Arg Gly Arg
65                  70                  75                  80

Val Leu Val His Cys Gln Ala Gly Ile Ser Arg Ser Ala Thr Ile Cys
                85                  90                  95

Leu Ala Tyr Leu Met Met Lys Leu Arg Val Arg Leu Glu Glu Ala Phe
                100                 105                 110

Glu Phe Val Lys Gln Arg Arg Ser Ile Ile Ser Pro Asn Phe Ser Phe
            115                 120                 125

Met Gly Gln Leu Leu Gln Phe Glu Ser Gln Val
        130                 135

<210> SEQ ID NO 11
<211> LENGTH: 139
<212> TYPE: PRT
<213> ORGANISM: Artificial
<220> FEATURE:
<223> OTHER INFORMATION: Description of Artificial Sequence:  mMKP-1

<400> SEQUENCE: 11

Pro Val Glu Ile Leu Ser Phe Leu Tyr Leu Gly Ser Ala Tyr His Ala
1               5                   10                  15

Ser Arg Lys Asp Met Leu Asp Ala Leu Gly Ile Thr Ala Leu Ile Asn
                20                  25                  30

Val Ser Ala Asn Cys Pro Asn His Phe Glu Gly His Tyr Gln Tyr Lys
            35                  40                  45

Ser Ile Pro Val Glu Asp Asn His Lys Ala Asp Ile Ser Ser Trp Phe
    50                  55                  60

Asn Glu Ala Ile Asp Phe Ile Asp Ser Ile Lys Asp Ala Gly Gly Arg
65                  70                  75                  80

Val Phe Val His Cys Gln Ala Gly Ile Ser Arg Ser Ala Thr Ile Cys
                85                  90                  95

Leu Ala Tyr Leu Met Arg Thr Asn Arg Val Lys Leu Asp Glu Ala Phe
                100                 105                 110
```

```
Glu Phe Val Lys Gln Arg Arg Ser Ile Ile Ser Pro Asn Phe Ser Phe
            115                 120                 125

Met Gly Gln Leu Leu Gln Phe Glu Ser Gln Val
            130                 135

<210> SEQ ID NO 12
<211> LENGTH: 140
<212> TYPE: PRT
<213> ORGANISM: Artificial
<220> FEATURE:
<223> OTHER INFORMATION: Description of Artificial Sequence: MH3/6

<400> SEQUENCE: 12

Leu Thr Arg Ile Leu Pro His Leu Tyr Leu Gly Ser Gln Lys Asp Val
1               5                   10                  15

Leu Asn Lys Asp Leu Met Thr Gln Asn Gly Ile Ser Tyr Val Leu Asn
            20                  25                  30

Ala Ser Asn Ser Cys Pro Lys Pro Asp Phe Ile Cys Glu Ser Arg Phe
            35                  40                  45

Met Arg Ile Pro Ile Asn Asp Asn Tyr Cys Glu Lys Leu Leu Pro Trp
        50                  55                  60

Leu Asp Lys Ser Ile Glu Phe Ile Asp Lys Ala Lys Leu Ser Ser Cys
65                  70                  75                  80

Gln Val Ile Val His Cys Leu Ala Gly Ile Ser Arg Ser Ala Thr Ile
                85                  90                  95

Ala Ile Ala Tyr Ile Met Lys Thr Met Gly Met Ser Ser Asp Asp Ala
                100                 105                 110

Tyr Arg Phe Val Lys Asp Arg Arg Pro Ser Ile Ser Pro Asn Phe Asn
            115                 120                 125

Phe Leu Gly Gln Leu Leu Glu Tyr Glu Arg Ser Leu
            130                 135                 140

<210> SEQ ID NO 13
<211> LENGTH: 139
<212> TYPE: PRT
<213> ORGANISM: Artificial
<220> FEATURE:
<223> OTHER INFORMATION: Description of Artificial Sequence: mPAC-1

<400> SEQUENCE: 13

Pro Val Glu Ile Leu Pro Tyr Leu Tyr Leu Gly Ser Cys Asn His Ser
1               5                   10                  15

Ser Asp Leu Gln Gly Leu Gln Ala Cys Gly Ile Thr Ala Val Leu Asn
            20                  25                  30

Val Ser Ala Ser Cys Pro Asn His Phe Glu Gly Leu Phe His Tyr Lys
            35                  40                  45

Ser Ile Pro Val Glu Asp Asn Gln Met Val Glu Ile Ser Ala Trp Phe
        50                  55                  60

Gln Glu Ala Ile Ser Phe Ile Asp Ser Val Lys Asn Ser Gly Gly Arg
65                  70                  75                  80

Val Leu Val His Cys Gln Ala Gly Ile Ser Arg Ser Ala Thr Ile Cys
                85                  90                  95

Leu Ala Tyr Leu Ile Gln Ser His Arg Val Arg Leu Asp Glu Ala Phe
                100                 105                 110

Asp Phe Val Lys Gln Arg Arg Gly Val Ile Ser Pro Asn Phe Ser Phe
            115                 120                 125

Met Gly Gln Leu Leu Gln Leu Glu Thr Gln Val
            130                 135
```

<210> SEQ ID NO 14
<211> LENGTH: 139
<212> TYPE: PRT
<213> ORGANISM: Artificial
<220> FEATURE:
<223> OTHER INFORMATION: Description of Artificial Sequence: hVH3

<400> SEQUENCE: 14

```
Pro Val Glu Ile Leu Pro Phe Leu Tyr Leu Gly Ser Ala Tyr His Ala
1               5                   10                  15

Ser Lys Cys Glu Phe Leu Ala Asn Leu His Ile Thr Ala Leu Leu Asn
            20                  25                  30

Val Ser Arg Arg Thr Ser Glu Ala Cys Met Thr His Leu His Tyr Lys
        35                  40                  45

Trp Ile Pro Val Glu Asp Ser His Thr Ala Asp Ile Ser Ser His Phe
    50                  55                  60

Gln Glu Ala Ile Asp Phe Ile Asp Cys Val Arg Glu Lys Gly Gly Lys
65                  70                  75                  80

Val Leu Val His Cys Glu Ala Gly Ile Ser Arg Ser Pro Thr Ile Cys
                85                  90                  95

Met Ala Tyr Leu Met Lys Thr Lys Gln Phe Arg Leu Lys Glu Ala Phe
            100                 105                 110

Asp Tyr Ile Lys Gln Arg Arg Ser Met Val Ser Pro Asn Phe Gly Phe
        115                 120                 125

Met Gly Gln Leu Leu Gln Tyr Glu Ser Glu Ile
    130                 135
```

<210> SEQ ID NO 15
<211> LENGTH: 139
<212> TYPE: PRT
<213> ORGANISM: Artificial
<220> FEATURE:
<223> OTHER INFORMATION: Description of Artificial Sequence: hVHR

<400> SEQUENCE: 15

```
Val Gly Asn Ala Ser Val Ala Gln Asp Ile Pro Lys Leu Gln Lys Leu
1               5                   10                  15

Gly Ile Thr His Val Leu Asn Ala Ala Glu Gly Arg Ser Phe Met His
            20                  25                  30

Val Asn Thr Asn Ala Asn Phe Tyr Lys Asp Ser Gly Ile Thr Tyr Leu
        35                  40                  45

Gly Ile Lys Ala Asn Asp Thr Gln Glu Phe Asn Leu Ser Ala Tyr Phe
    50                  55                  60

Glu Arg Ala Ala Asp Phe Ile Asp Gln Ala Leu Ala Gln Lys Asn Gly
65                  70                  75                  80

Arg Val Leu Val His Cys Arg Glu Gly Tyr Ser Arg Ser Pro Thr Leu
                85                  90                  95

Val Ile Ala Tyr Leu Met Met Arg Gln Lys Met Asp Val Lys Ser Ala
            100                 105                 110

Leu Ser Ile Val Arg Gln Asn Arg Glu Ile Gly Pro Asn Asp Gly Phe
        115                 120                 125

Leu Ala Gln Leu Cys Gln Leu Asn Asp Arg Leu
    130                 135
```

<210> SEQ ID NO 16
<211> LENGTH: 12
<212> TYPE: PRT

<213> ORGANISM: Artificial
<220> FEATURE:
<223> OTHER INFORMATION: Description of Artificial Sequence: consensus
      sequence

<400> SEQUENCE: 16

Ile Leu Pro Phe Leu Tyr Leu Gly Ser Ala Lys Asp
1               5                   10

<210> SEQ ID NO 17
<211> LENGTH: 5
<212> TYPE: PRT
<213> ORGANISM: Artificial
<220> FEATURE:
<223> OTHER INFORMATION: Description of Artificial Sequence: consensus
      sequence

<400> SEQUENCE: 17

Ile Leu Asn Val Thr
1               5

<210> SEQ ID NO 18
<211> LENGTH: 4
<212> TYPE: PRT
<213> ORGANISM: Artificial
<220> FEATURE:
<223> OTHER INFORMATION: Description of Artificial Sequence: consensus
      sequence

<400> SEQUENCE: 18

Phe Lys Tyr Lys
1

<210> SEQ ID NO 19
<211> LENGTH: 7
<212> TYPE: PRT
<213> ORGANISM: Artificial
<220> FEATURE:
<223> OTHER INFORMATION: Description of Artificial Sequence: consensus
      sequence

<400> SEQUENCE: 19

Asp Ala Tyr Asp Phe Val Lys
1               5

<210> SEQ ID NO 20
<211> LENGTH: 4
<212> TYPE: PRT
<213> ORGANISM: Artificial
<220> FEATURE:
<223> OTHER INFORMATION: Description of Artificial Sequence: consensus
      sequence

<400> SEQUENCE: 20

Gln Leu Leu Ile
1

<210> SEQ ID NO 21
<211> LENGTH: 32
<212> TYPE: DNA
<213> ORGANISM: Artificial
<220> FEATURE:
<223> OTHER INFORMATION: Description of Artificial Sequence:
      oligonucleotide 1065-30

<400> SEQUENCE: 21 ccttttgag caagttcagc ctggttaagt cc                              32

<210> SEQ ID NO 22
<211> LENGTH: 34
<212> TYPE: DNA
<213> ORGANISM: Artificial
<220> FEATURE:
<223> OTHER INFORMATION: Description of Artificial Sequence:
      oligonucleotide 1386-58

<400> SEQUENCE: 22
ggaggcctct ctctgtgtgt gtggagccct cagg                                 34

<210> SEQ ID NO 23
<211> LENGTH: 31
<212> TYPE: DNA
<213> ORGANISM: Artificial
<220> FEATURE:
<223> OTHER INFORMATION: Description of Artificial Sequence:
      oligonucleotide 1386-59

<400> SEQUENCE: 23
ggcagcacca gcctgaactt tgcaatattt c                                    31

<210> SEQ ID NO 24
<211> LENGTH: 19
<212> TYPE: DNA
<213> ORGANISM: Artificial
<220> FEATURE:
<223> OTHER INFORMATION: Description of Artificial Sequence:
      oligonucleotide 1470-25

<400> SEQUENCE: 24
cagcagcgga ttcaccatc                                                  19

<210> SEQ ID NO 25
<211> LENGTH: 19
<212> TYPE: DNA
<213> ORGANISM: Artificial
<220> FEATURE:
<223> OTHER INFORMATION: Description of Artificial Sequence:
      oligonucleotide 1470-26

<400> SEQUENCE: 25
gcgatcacca gtgtcacgc                                                  19

<210> SEQ ID NO 26
<211> LENGTH: 14
<212> TYPE: PRT
<213> ORGANISM: Homo sapiens

<400> SEQUENCE: 26

Cys Gly Asn Phe Lys Asp Ala Arg Asp Ala Glu Gln Leu Ser
1               5                   10

<210> SEQ ID NO 27
<211> LENGTH: 18
<212> TYPE: PRT
<213> ORGANISM: Artificial
<220> FEATURE:
<223> OTHER INFORMATION: Description of Artificial Sequence: peptide for
      preparation of polyclonal antibodie

<400> SEQUENCE: 27

Cys Lys Asn Gly Val Ile Arg Gly Gln Pro Ser Pro Leu Ala Gln Val
1               5                   10                  15

Gln Gln

PHOSPHATASES WHICH ACTIVATE MAP KINASE PATHWAYS

This application is a divisional of U.S. application Ser. No. 09/665,819, filed Sep. 20, 2000 (now U.S. Pat. No. 6,900,043), which claims the benefit of priority from U.S. Provisional application No. 60/155,068, filed Sep. 21, 1999.

FIELD OF THE INVENTION

The present invention relates to novel JNK activating phosphatase polypeptides and nucleic acid molecules encoding the same. The invention also relates to vectors, host cells, antibodies and methods for producing JNK activating phosphatase polypeptides. Also provided for are methods for the diagnosis and treatment of diseases associated with JNK activating phosphatase polypeptides.

BACKGROUND OF THE INVENTION

Technical advances in the identification, cloning, expression, and manipulation of nucleic acid molecules have greatly accelerated the discovery of novel therapeutics based upon deciphering the human genome. Rapid nucleic acid sequencing techniques can now generate sequence information at unprecedented rates and, coupled with computational analyses, allow the assembly of overlapping sequences into entire genomes and the identification of polypeptide-encoding regions. Comparison of a predicted amino acid sequence against a database compilation of known amino acid sequences can allow one to determine the extent of homology to previously identified sequences and/or structural landmarks. Cloning and expression of a polypeptide-encoding region of a nucleic acid molecule provides a polypeptide product for structural and functional analysis. Manipulation of nucleic acid molecule and encoded polypeptides to give variants and derivatives thereof may confer advantageous properties on a product for use as a therapeutic.

In spite of the significant technical advances in genome research over the past decade, the potential for development of novel therapeutics based on the human genome is still largely unrealized. Genes encoding potentially beneficial protein therapeutics, or those encoding polypeptides that may act as "targets" for therapeutic molecules have still not been identified. In addition, structural and functional analyses of polypeptide products from many human genes have not been undertaken.

Accordingly, it is an object of the invention to identify novel polypeptides and nucleic acid molecules encoding the same which have diagnostic or therapeutic benefit.

SUMMARY OF THE INVENTION

The present invention relates to novel JNK activating phosphatase nucleic acid molecules and encoded polypeptides.

The invention provides for an isolated nucleic acid molecule comprising a nucleotide sequence selected from the group consisting of:

(a) the nucleotide sequence as set forth in SEQ ID NOS: 1 or 3;

(b) a nucleotide sequence encoding the polypeptide as set forth in SEQ ID NOS: 2 or 4;

(c) a nucleotide sequence corresponding to nucleotide position number 181 to 795 in SEQ ID NO:1 or nucleotide position number 15 to 629 in SEQ ID NO:3;

(d) a nucleotide sequence encoding a polypeptide that is at least about 80, 85, 90, 95, 96, 97, 98, or 99 percent identical to the nucleotide sequence of (c);

(e) an allelic variant or splice variant of any of (a), (b, (c) or (d);

(f) a nucleotide sequence of (b), (c), (d) or (e) encoding a polypeptide fragment of at least about 25, 50, 75, 100, or greater than 100 amino acid residues wherein the polypeptide fragment has an activity of regulating JNK activation or modulating JINX-mediated signal transduction;

(g) a nucleotide sequence of (a), (b), (c) or (d) comprising a fragment of at least about 10, 15, 20, 25, 50, 75, 100, or greater than 100 nucleotides;

(h) a nucleotide sequence encoding a polypeptide that has a substitution and/or deletion of 1 to 100 amino acid residues as set forth in any of SEQ ID NOS: 2 or 4 wherein the polypeptide has an activity of regulating JNK activation or modulating JNK-mediated signal transduction; or serves as an antigen for generating antibodies; and (i) a nucleotide sequence which hybridizes under stringent conditions to any of (a)–(h);

(j) a nucleotide sequence complementary to any of (a)–(h).

The invention also provides for an isolated polypeptide comprising the amino acid sequence selected from the group consisting of:

(a) the amino acid sequence as set forth in SEQ ID NOS: 2 or 4;

(b) a fragment of the amino acid sequence set forth in SEQ ID NOS: 2 OR 4 comprising at least about 25, 50, 75, 100, or greater than 100 amino acid residues wherein the fragment has an activity of regulating JNK activation or modulating JNK-mediated signal transduction; or serves as an antigen for generating antibodies;

(c) an ortholog of SEQ ID NOS: 2 or 4; and (d) an allelic variant or splice variant of (a) or (c).

The invention also provides for an expression vector comprising the nucleic acid molecules as set forth above, host cells comprising the expression vectors of the invention, and a method of production of an JNK activating phosphatase polypeptide comprising culturing the host cells and optionally isolating the polypeptide so produced.

A transgenic non-human animal comprising a nucleic acid molecule encoding an JNK activating phosphatase polypeptide is also encompassed by the invention. The JNK activating phosphatase nucleic acid molecules are introduced into the animal in a manner that allows expression and increased levels of an INK activating phosphatase polypeptide, which may include increased circulating levels. Alternatively, the JNK activating phosphatase nucleic acid molecules are introduced into the animal in a manner that prevents expression of endogenous JNK activating phosphatase (i.e., generates a transgenic animal possessing an JNK activating phosphatase gene knockout). The transgenic non-human animal is preferably a mammal, and more preferably a rodent, such as a rat or a mouse.

Also provided are derivatives of the JNK activating phosphatase polypeptides of the invention, fusion polypeptides comprising the JNK activating phosphatase polypeptides of the invention, and antibodies specifically binding the JNK activating phosphatase polypeptides of the invention.

Compositions comprising the nucleotides or polypeptides of the invention and a carrier, adjuvant, solubilizer, stabilizer or anti-oxidant, or other pharmaceutically acceptable agent are also encompassed by the invention. The compositions may include pharmaceutical compositions comprising therapeutically effective amounts of the nucleotides or polypeptides of the invention, and methods of using the polypeptides and nucleic acid molecules.

Surprisingly, JNK activating phosphatase polypeptide was differentially expressed in hematopoietic cells, thereby distinguishing it from other dual-activity phosphatases. Therefore, the present polypeptide, and its useful nucleic acid intermediates, may have utility in differentiating hematopoietic cells from background.

The JNK activating phosphatase polypeptides and nucleic acid molecules of the invention may be used to screen for therapeutic agents to treat, prevent and/or detect conditions relating to JNK-mediated disorders. The invention provides for treating, preventing or ameliorating a JNK-mediated disorder comprising administering to an animal an INK activating phosphatase polypeptide. The invention also provides for a method of diagnosing a JNK-mediated disorder or a susceptibility to a JNK-mediated disorder in an animal which includes both determining the presence or amount of expression of an JNK activating phosphatase polypeptide and diagnosing a JNK-mediated disorder or a susceptibility to a JNK-mediated disorder based on the presence or amount of expression of an JNK activating phosphatase polypeptide. The animal is preferably a mammal, and more preferably a human. The present invention also relates to methods for manufacture of a medicament for the treatment of JNK-mediated disorders.

In mammalian cells, a specific protein kinase pathway is activated in response to stress due to, for instance, inflammatory cytokines, chemotherapeutic drugs and UV or ionizing radiation. The term "JNK-mediated disorder" is used to describe a pathological condition resulting, at least in part, from excessive activation of a c-Jun amino-terminal kinase (JNK) signal transduction pathway in response to such a stress. JNK-mediated disorders may include, for example, ischemic heart disease, cardiac hypertrophy, burns due to heat or radiation (UV, X-ray, gamma, beta, etc.), kidney failure, liver damage due to oxidative stress or alcohol, respiratory distress syndrome, septic shock, rheumatoid arthritis, autoimmune disorders, and other types of inflammatory diseases. JNK-mediated disorders further include proliferative disorders. Examples of stress-related JNK-mediated proliferative disorders might include psoriasis and malignancies of various tissues of the body, such as malignancies of the skin, bone marrow, lung, liver, breast, gastrointestinal system, and genito-urinary tract The present invention provides a polypeptide (a phosphatase) involved in the JNK signal transduction pathway. The polypeptide modulates the response of a c-Jun amino-terminal kinase to cytokines or other stimuli, thereby regulating JNK activation and modulating JNK-mediated signal transduction. The modulation of JNK activity includes inhibitory or stimulatory effects. In some cases, augmentation of JNK activity is desirable, e.g., induction of apoptosis.

A therapeutic agent that inhibits JNK activity will interfere with the JNK-mediated signal transduction pathway. For example, a therapeutic agent may alter the protein kinase activity of JNK, decrease the level of JNK transcription or translation (e.g., an antisense polynucleotide able to bind JNK mRNA), or alter JNK phosphorylation, thus disrupting the JNK-mediated signal transduction pathway. Further examples of such agents include antibodies that bind specifically to JNK-activating polypeptides, and fragments of JNK-activating polypeptides that competitively inhibit JNK activity.

A therapeutic agent that promotes or enhances JNK activity supplements a JNK-mediated signal transduction pathway. For example, a promoting agent can be administered in instances where the JNK-mediated disorder is caused by under-expression of the JNK-activating polypeptide. In addition, portions of DNA encoding a JNK-activating polypeptide can be introduced into cells that under-express a JNK-activating polypeptide.

The polypeptides of the present invention may be used to screen therapeutic agents for treating a disease involving cytokine production in an animal. The agent may regulate cellular response to proinflammatory cytokines produced as a result of exposure to certain stressors. Such diseases include medical disorders and diseases in which the pathogenesis of the disease and/or the physiological effects of the disease might be ameliorated by regulation of response to proinflammatory cytokines. Such diseases include, but are not limited to, allergic diseases, anaphylaxis, inflammation, mast cell disorders, sepsis and cancer.

The polypeptides and polynucleotides of the invention are useful for identifying agents which modulate the JNK signal transduction pathways. Agents that inhibit a JNK signal transduction pathway can be used in the treatment of JNK-mediated disorders, as described above. Agents that stimulate a JNK signal transduction pathway can be used in a number of ways, including inducing programmed cell death (apoptosis) in tissues. For example, the elimination of UV damaged cells can be used to prevent cancer.

The present invention further provides the means for both acute and prophylactic treatment of stress-related and inflammatory disorders. For example, it is envisioned that ischemic heart disease may be treated during episodes of ischemia and oxidative stress following reperfusion. In addition, a patient at risk for ischemia may be treated prior to ischemic episodes. In another example, a therapeutic agent which inhibits JNK activity may be administered to control inflammatory responses by inhibiting the response to inflammatory cytokines, including TNF and IL-1. Stress-related proliferative disorders can also be treated by administering a therapeutic agent that inhibits JNK activity. Such therapeutic agents can be used alone or in combination with other therapeutic agents, for example, with chemotherapeutic agents in the treatment of malignancies.

Agents used to modulate JNK activity, include polynucleotides, polypeptides, and other molecules such as antisense oligonucleotides and ribozymes. Thus, the present invention provides means for treating a JNK-mediated disorders by administering to a subject in need thereof an effective dose of a therapeutic agent that modulates (inhibits or enhances, as required) the activity of JNK As used herein, the term "therapeutic agent" means any compound or molecule that achieves the desired effect on a JNK-mediated disorder when administered to a subject in need thereof Therapeutic uses of such agents include but are not limited to the following: acute pancreatitis; ALS; Alzheimer's disease; cachexia/anorexia; asthma; atherosclerosis; chronic fatigue syndrome, fever, diabetes (e.g., insulin diabetes); glomerulonephritis; graft versus host rejection; hemohorragic shock; hyperalgesia, inflammatory bowel disease; inflammatory conditions of a joint, including osteoarthritis, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, especially in sepsis); osteoporosis; Parkinson's disease; pain; pre-term labor, psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

JNK- or JNK-like activity also appears to be involved in cardiac hypertrophy. See for example, Silberbach et al., J. Biol. Chem., 274 (35):24858–24864 (1999); Yano et al., Circ. Res., 83 (7): 752–760 (1998); Adams et al., Circ. Res., 83 (2):167–178 (1998); Memoto et al., Mol. Cell. Biol., 18 (6): 3518–3526 (1998); Wang et al., J. Biol. Chem., 273 (10): 5423–5426 (1998); and Ramirez et al., J. Biol. Chem., 272 (22):14057–14061 (1997). An inhibitor of JNK activity may ameliorate such an event.

The present invention provides a means to produce agents useful in the prophylaxis and treatment of tumor necrosis factor α (TNF-α) mediated and interleukin-1 (IL- 1) mediated diseases as well as other maladies, such as diseases involving inflammation, pain and diabetes, through the inhibition or reduction of JNK activity. JNK appears to be activated by TNF-α and IL-1 and appears to be involved in their signaling pathway. Inhibition or reduction of JNK activity could mitigate the effects of TNF-α, IL-1β, IL-6 and/or IL-8, in particular elevated levels of TNF-α and IL-1. Thus, the inhibition or reduction of JKAP activity would inhibit or reduce JNK activity and thereby mitigate the effects of this signaling pathway.

IL-1 and TNF-α are pro-inflammatory cytokines secreted by a variety of cells, including monocytes and macrophages, in response to many inflammatory stimuli (e.g., lipopolysaccharide-LPS) or external cellular stress (e.g., osmotic shock and peroxide). Elevated levels of TNF-α and/or IL-1 over basal levels have been implicated in mediating or exacerbating a number of disease states including rheumatoid arthritis; Pagets disease; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CNM), influenza, adenovirus, the herpes viruses (including HSV-1, HSV-2), and herpes zoster are also exacerbated by TNF-α.

Also, TNF-α has been reported to play a role in head trauma, stroke, and ischemia (Shohami et al., J. Cereb. Blood Flow Metab. 14, 615 (1994); Feurstein et al., Neurosci. Lett. 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, Stroke 25, 1481 (1994)). TNF-α haas also been implicated to play a role in type II diabetes (Endocrinol. 130, 43–52, 1994; and Endocrinol. 136, 1474–1481, 1995). TNF-α also appears to play a role in promoting certain viral life cycles and disease states associated with them (Clouse et al., J. Immunol. 142, 431(1989); Lahdevirta et al., Am. J. Med. 85, 289 (1988)).

TNF-α is upstream in the cytokine cascade of inflammation. As a result, elevated levels of TNF-α may lead to elevated levels of other inflammatory and proinflammatory cytokines, such as IL-1, IL-6, and IL-8. Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1. IL-1 also appears to play a role in promoting certain viral life cycles (Folks et al., J. Immunol. 136, 40 (1986)). Beutler et al. (J. Immunol. 135, 3969 (1985)) discussed the role of IL-1 in cachexia. Baracos et al. (New Eng. J. Med. 308, 553 (1983)) discussed the role of IL-1 in muscle degeneration. TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis, both IL-1 and TNF-α induce synoviocytes and chondrocytes to produce collage ase and neutral proteases, which leads to tissue destruction within the arthritic joints. In rheumatoid arthritis models in animals, multiple intra-articular injections of TNF-α or IL-1 have led to an acute and destructive form of arthritis (Brahn et al., Lymphokine Cytokine Res. 11, 253 (1992); and Cooper, Clin. Exp. Inmunol. 898, 244 (1992); Chandrasekhar et al., Clinical Immunol Immunopathol. 55, 382 (1990)). In studies using cultured rheumatoid synovial cells, IL-1 is a more potent inducer of stromelysin than is TNF-α (Firestein, Am. J. Pathol 140, 1309 (1992)). At sites of local injection, neutrophil, lymphocyte, and monocyte emigration has been observed, which is attributed to the induction of chemokines (e.g., IL-8), and the up-regulation of adhesion molecules (Dinarello, Eur. Cytokine Netw. 5, 517–531 (1994)).

The invention also provides for a method of identifying a test molecule which binds to an JNK activating phosphatase polypeptide wherein the method comprises contacting an JNK activating phosphatase polypeptide with a test molecule and determining the extent of binding of the test molecule to the polypeptide. The method further comprises determining whether such test molecules are agonists or antagonists of an JNK activating phosphatase polypeptide.

The invention also provides for a method of testing the impact of molecules on the expression of JNK activating phosphatase polypeptide or on the activity of JNK activating phosphatase polypeptide.

A method of regulating expression and modulating (i.e., increasing or decreasing) levels of an JNK activating phosphatase polypeptide are also encompassed by the invention. One method comprises administering to an animal a nucleic acid molecule encoding an JNK activating phosphatase polypeptide. In another method, a nucleic acid molecule comprising elements that regulate expression of an JNK activating phosphatase polypeptide may be administered. Examples of these methods include gene therapy and antisense therapy.

DESCRIPTION OF THE FIGURES

The foregoing and other aspects and advantages of the invention will be apparent on consideration of the following detailed description and the accompanying drawings, wherein:

FIG. 1 illustrates the nucleotide sequence of the human JNK activating phosphatase gene (SEQ ID NO: 1) and the deduced amino acid sequence of human JNK activating phosphatase protein (SEQ ID NO: 2).

FIG. 2 illustrates the nucleotide sequence of the mouse JNK activating phosphatase gene (SEQ ID NO: 3) and the deduced amino acid sequence of mouse JNK activating phosphatase protein (SEQ ID NO: 4).

FIG. 4 illustrates the In situ expression analysis of JKAP. (A and B) Lin⁻ Sca-1⁺ cells (A) and Lin⁻ Sca-1⁻ cells (B) obtained from adult mouse bone marrow by FACS were hybridized with a JKAP cDNA fragment (C through E) E10.5 mouse embryos were hybridized with a JKAP antisense riboprobe, 20× (C) and a JKAP sense riboprobe, 20× (D). The caudal region is shown at 50× (E). (F) 10 µm transverse sections were taken through the caudal region of the embryo in (C), 200× (JWB).

FIG. 6 illustrates the generation of JKAP⁻/⁻ ES cells. (A) The JKAP genomic locus, targeting vector, and mutated locus are schematically represented. Restriction enzyme sites (B. BamHI; X, XbaI; S, SalI) and the probe used to detect targeting events are indicated. (B) Genomic DNA was isolated from JKAP⁺/⁺ and JKAP⁻/⁻, and JKAP⁻/⁻ ES cells, which were derived through selection of JKAP⁺/⁻ ES cell lines in 2 mg/nL G418. The DNA was digested with BamHI, transferred for Southern analysis, and hybridized with a probe flanking the 5' insertion site of the targeting vector. Molecular weights in kilobase pairs are indicated on the left (C) Total RNA from JKAP⁺/⁺, JKAP⁺/⁻, and JKAP⁻/⁻ ES cells was isolated and hybridized with a JKAP cDNA probe. RNA integrity and quantity was evaluated by methylene blue staining after Norther transfer. Molecular weight in kilobase pairs is indicated on the left.

DETAILED DESCRIPTION OF THE INVENTION

Figure 3B:
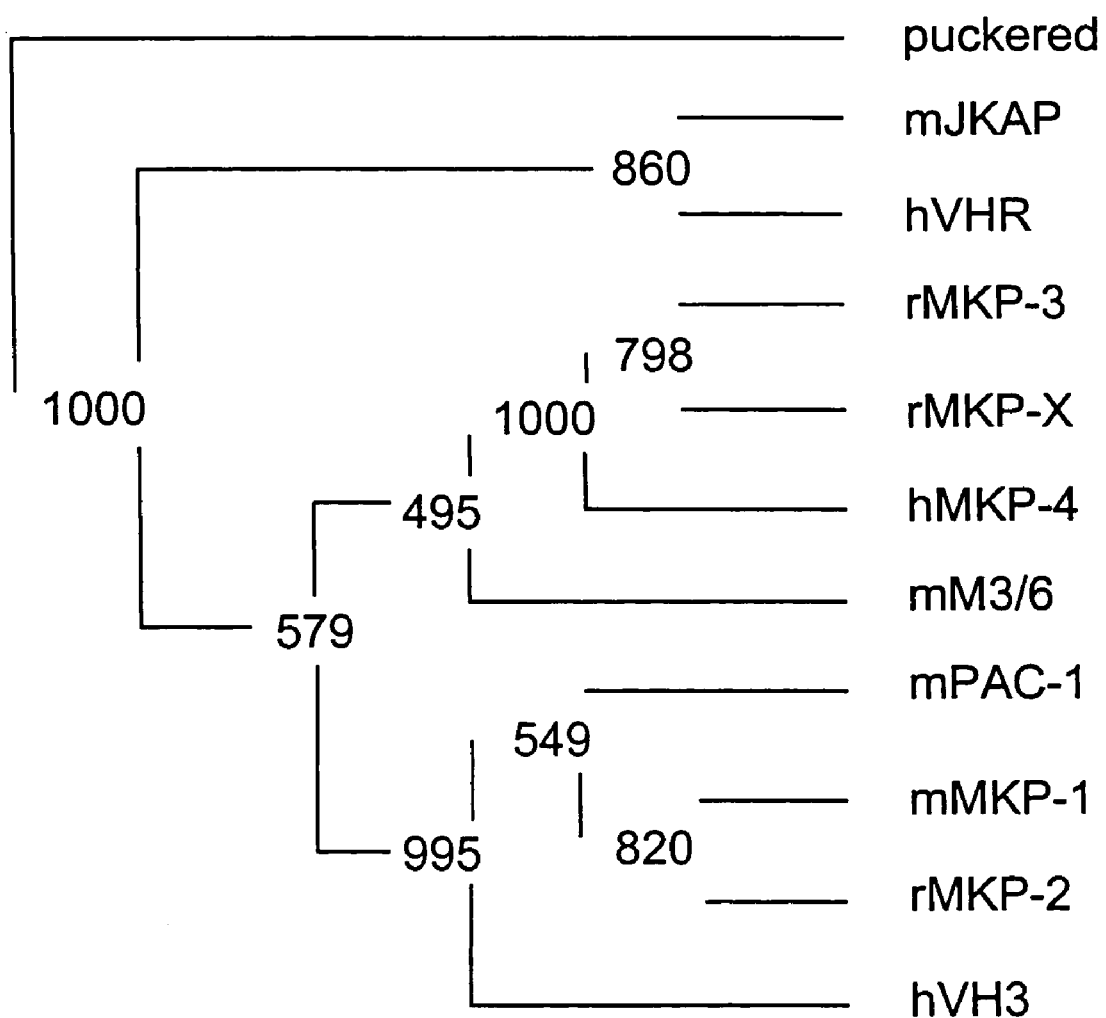
FIG. 3 illustrates the JKAP amino acid sequence analysis and expression pattern. (A) Amino acids sequences corresponding to the catalytic domains of selected MAPK phosphatases were aligned in PIMA 1.4 using sequential branching clustering. The resulting alignment was processed in BOXSHADE. Sequence identities are highlighted in black; similarities are highlighted in gray. Gaps are indicated by dots. The aligned sequences include mJKAP (SEQ ID NO: 5); puckered (SEQ ID NO: 6); rMKP-3 (SEQ ID NO: 7); rMKP-X (SEQ ID NO: 8); hMKP-4 (SEQ ID NO: 9); rMKP-2 (SEQ ID NO: 10); mMKP-1 (SEQ ID NO: 11); mH3/6 (SEQ ID NO: 12); mPAC-1 (SEQ ID NO: 13); hVH3 (SEQ ID NO: 14); and hVHR (SEQ ID NO: 15) and the resulting consensus sequence (SEQ ID NO: 16 to 20). (B) Phylogenetic analysis was carried out on aligned sequences by parsimony in PHYLIP using PROTPARS with bootstrapping of 1000 replicates. The numbers correspond to the occurrences of the branch in the consensus tree. (C) Polyadenylated mRNA from adult mouse tissues was hybridized with a JKAP cDNA probe. mRNA integrity and quantity was confirmed by hybridization with β-actin. Molecular weights in kilobase pairs are indicated on the left.

The section headings herein are for organizational purposes only and are not to be construed as limiting the subject matter described therein. All references cited in this application are expressly incorporated by reference herein.

A novel dual-specificity phosphatase, a JNK activating phosphatase (JKAP) that selectively upregulates the JNK pathway was cloned and characterized. This protein appears to be required for maximal JNK activation. Overexpression of JNK activating phosphatase specifically activated the JNK cascade. Targeted gene disruption in cultured embryonic stem cells demonstrated that JNK activating phosphatase was necessary for induction of JNK activity by proinflammatory cytokines and osmotic stress, but not ultraviolet (UV) irradiation. These data suggest a new role for phosphatases in the regulation of signaling by MAP kinases.

Much interest in phosphatases has stemmed from the concept that phosphatases serve to "turn off" what kinases "turn on". Certainly, previously identified dual-specificity phosphatases have primarily inactivated MAPK's, through dephosphorylation of the threonine and tyrosine residues in the TXY motif of the catalytic domain of the kinase (M. H. Cobb and E. J. Goldsmith, *J. Biol. Chem.* 270, 14843 (1995)). JNK activating phosphatase uniquely activates the JNK pathway, but through a mechanism which remains to be resolved. Direct dephosphorylation of inhibitory residues on JNK is one possibility, as is inactivation of an inhibitory protein. JNK activating phosphatase may activate a kinase component upstream of JNK, rather than JNK directly.

The mechanism through which JNK activating phosphatase exhibits pathway specificity for JNK over ERK and p38 also remains unclear. Other MAP kinase phosphatases are predicted to determine pathway specificity through a non-catalytic N-terminal domain, which is responsible for substrate binding (M. Camps et al., *Science* 280, 1262 (1998); M. Muda et al., *J. Biol. Chem.* 273, 9323 (1998)). JNK activating phosphatase retains high specificity for JNK despite the lack of an N-terminal domain. The specificity of JNK activating phosphatase could be inherent in the catalytic pocket, or perhaps an interacting protein provides substrate selectivity.

The requirement for JNK activating phosphatase in stimulus-induced JNK activation is a novel observation among MAP kinase phosphatases. This, along with the other unusual characteristics of JNK activating phosphatase, supports a more complex role of phosphatases in MAP kinase signaling than as a simple "off switch".

Definitions

The term "JNK activating phosphatase nucleic acid molecule" refers to a nucleic acid molecule comprising or consisting essentially of a nucleotide sequence as set forth in SEQ ID NOS: 1 or 3, comprising or consisting essentially of a nucleotide sequence encoding the polypeptide as set forth in SEQ ID NOS: 1 or 3.

Related nucleic acid molecules comprise or consist essentially of a nucleotide sequence that is about 70 percent identical to the nucleotide sequence as shown in SEQ ID NOS: 1 or 3, or comprise or consist essentially of a nucleotide sequence encoding a polypeptide that is about 70 percent identical to the polypeptide as set forth in SEQ ID NOS: 2 or 4. In preferred embodiments, the nucleotide sequences are about 75 percent, or about 80 percent, or about 85 percent, or about 90 percent, or about 95, 96, 97, 98, or 99 percent identical to the nucleotide sequence corresponding to SEQ ID NOS: 1 or 3, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NOS: 2 or 4. Related nucleic acid molecules also include fragments of the above JNK activating phosphatase nucleic acid molecules which are at least about 10 contiguous nucleotides, or about 15, or about 20, or about 25, or about 50, or about 75, or about 100, or greater than about 100 contiguous nucleotides. Related nucleic acid molecules also include fragments of the above JNK activating phosphatase nucleic acid molecules which encode a polypeptide of at least about 25 amino acid residues, or about 50, or about 75, or about 100, or greater than about 100 amino acid residues. Related nucleic acid molecules also include a nucleotide sequence encoding a polypeptide comprising or consisting essentially of a substitution, modifications and/or a deletion of one to 50 amino acid residues compared to the polypeptide in SEQ ID NOS: 2 or 4. Related JNK activating phosphatase nucleic acid molecules include those molecules that comprise nucleotide sequences which hybridize under moderately or highly stringent conditions as defined herein with any of the above nucleic acid molecules or their complements. In preferred embodiments, the related nucleic acid molecules comprise sequences which hybridize under moderately or highly stringent conditions with the sequence as shown in SEQ ID NOS: 1 or 3, or with a molecule encoding a polypeptide, which polypeptide comprises the sequence as shown in SEQ ID NOS: 2 or 4, or with a nucleic acid fragment as defined above, or with a nucleic acid fragment encoding a polypeptide as defined above. It is also understood that related nucleic acid molecules include allelic or splice variants of any of the above nucleic acids, and include sequences which are complementary to any of the above nucleotide sequences.

The term "isolated nucleic acid molecule" refers to a nucleic acid molecule of the invention that is free from at least one contaminating nucleic acid molecule with which it is naturally associated, and preferably substantially free from any other contaminating mammalian nucleic acid molecules which would interfere with its use in protein production or its therapeutic or diagnostic use.

The term "allelic variant" refers to one of several possible naturally occurring alternate forms of a gene occupying a given locus on a chromosome of an organism or a population of organisms.

The term "splice variant" refers to a nucleic acid molecule, usually RNA, which is generated by alternative processing of intron sequences in an RNA transcript.

The term "expression vector" refers to a vector that is suitable for propagation in a host cell and contains nucleic acid sequences that direct and/or control the expression of inserted heterologous nucleic acid sequences. Expression includes, but is not limited to, processes such as transcription, translation, and RNA splicing, if introns are present.

The term "highly stringent conditions" refers to those conditions that (1) employ low ionic strength reagents and high temperature for washing, for example, 0.015 M NaCl/ 0.0015 M sodium citrate/0.1% NaDodSO$_4$ (SDS) at 50° C., or (2) employ during hybridization a denaturing agent such as formamide, for example, 50% (vol/vol) formamide with 0.1% bovine serum albumin. See Y. T. Ip and R. J. Davis, Curr. Opin. Cell Biol. 10, 205 (1998); D. C. I. Goberdhan and C. Wilson, Bioassays 20, 1009 (1998). Alternatively, an example includes use of Ficoll, 0.1% polyvinylpyrrolidone, 50 mM sodium phosphate buffer (pH 6.5), 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2×SSC and 0.1% SDS.

The term "moderately stringent conditions" refers to conditions which generally include the use of a washing solution and hybridization conditions (e.g., temperature, ionic strength, and percentage of SDS) less stringent than described above. An example of moderately stringent conditions are conditions such as overnight incubation at 37° C. in a solution comprising 20% formamide, 5×SSC (150 mM NaCl, 15 mM trisodium citrate), 50 mM sodium phosphate (pH 7.6), 5× Denhardt's solution, 10% dextran sulfate, and 20 μl/ml denatured sheared salmon sperm DNA, followed by washing in 1×SSC at about 37–50° C. The skilled artisan will recognize how to adjust the temperature, ionic strengt, etc. as necessary to accommodate factors such as probe length and the like.

In certain preferred embodiments, where oligonucleotide probes are used to screen cDNA or genomic libraries, high stringency conditions are used which depend upon the melting temperature ($T_m$) of oligonucleotide probes to target sequences. The $T_m$ may be estimated using the following formula (Bolton et al., Proc. Natl. Acad. Sci. U.S.A. 48:1390 (1962)):

$$T_m = 81.5 - 16.6(\log[Na+]) + 0.41(\% \ G+C) - (600/N)$$

wherein [Na+] is the sodium ion concentration in the hybridization (or washing) solution;

% G+C is guanine and cytosine content in the oligonucleotide probe; and

N is the probe length in nucleotides.

An example of a high stringency solution is 6×SSC and 0.05% sodium pyrophosphate at a temperature of 35–63° C., depending on the length of the oligonucleotide probe. For example, according to certain embodiments, 14 base pair probes are washed at 35–40° C., 17 base pair probes are washed at 45–50° C., 20 base pair probes are washed at 52–57° C., and 23 base pair probes are washed at 57–63° C. The temperature can be increased 2–3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2% SDS. The washing temperature using this solution is a function of the length of the probe. For example, 14 base pair probes are washed at 35–40° C., 17 base pair probes are washed at about 45–50° C., 20 base pair probes are washed at 52–57° C., and 23 base pair probes are washed at 57–63° C.

The term "JNK activating phosphatase polypeptides" refers to a polypeptide comprising the amino acid sequence of SEQ ID NOS: 1 OR 2, and related polypeptides described herein. Related polypeptides include: allelic variants; splice variants; fragments; derivatives; substitution, deletion, and insertion variants; fusion polypeptides; and orthologs. JNK activating phosphatase polypeptides may be mature polypeptides, as defined herein, and may or may not have an amino terminal methionine residue, depending on the method by which they are prepared.

The term "JNK activating phosphatase polypeptide fragment" refers to a peptide or polypeptide that comprises less than the full length amino acid sequence of an JNK activating phosphatase polypeptide as set forth in SEQ ID NOS: 2 OR 4. Such a fragment may arise, for example, from a truncation at the amino terminus, a truncation at the carboxyl terminus, and/or an internal deletion of a residue(s) from the amino acid sequence. JNK activating phosphatase fragments may result from alternative RNA splicing or from in vivo protease activity.

The term "JNK activating phosphatase polypeptide variants" refers to JNK activating phosphatase polypeptides comprising amino acid sequences which contain one or more amino acid sequence substitutions, deletions, and/or additions as compared to the JNK activating phosphatase polypeptide amino acid sequence set forth in SEQ ID NOS: 2 or 4. Variants may be naturally occurring or artificially constructed. Such JNK activating phosphatase polypeptide variants may be prepared from the corresponding nucleic acid molecules encoding said variants, which have a DNA sequence that varies accordingly from the DNA sequences for wild type JNK activating phosphatase polypeptides as set forth in SEQ ID NOS: 2 or 4.

The term "JNK activating phosphatase fusion polypeptide" refers to a fusion of an JNK activating phosphatase polypeptide, fragment, variant, or derivative thereof, with a heterologous peptide or polypeptide.

The term "JNK activating phosphatase polypeptide derivatives" refers to JNK activating phosphatase polypeptides, variants, or fragments thereof, that have been chemically modified, as for example, by covalent attachment of one or more polymers, including, but limited to, water soluble polymers, N-linked or O-linked carbohydrates, sugars, phosphates, and/or other such molecules. The derivatives are modified in a manner that is different from naturally occurring JNK activating phosphatase polypeptide, either in the type or location of the molecules attached to the polypeptide. Derivatives further include the deletion of one or more chemical groups naturally attached to the JNK activating phosphatase polypeptide.

The terms "biologically active JNK activating phosphatase polypeptides," "biologically active JNK activating phosphatase polypeptide fragments," "biologically active JNK activating phosphatase polypeptide variants," and "biologically active JNK activating phosphatase polypeptide derivatives" refer to JNK activating phosphatase polypeptides having at least one activity characteristic of an JNK activating phosphatase polypeptide, such as regulating JNK activation or mediating JNK-mediated signal transduction. In general, JNK activating phosphatase polypeptides, and variants, fragments and derivatives thereof, will have at least one activity characteristic of an JNK activating phosphatase polypeptide such as regulating JNK activation or mediating JNK-mediated signal transduction. In addition, a JNK activating phosphatase polypeptide may be active as an immunogen (i.e., the polypeptide contains at least one epitope to which antibodies may be raised).

"Naturally occurring" when used in connection with biological materials such as nucleic acid molecules, polypeptides, host cells, and the like, refers to that which are found in nature and not manipulated by a human being.

The term "isolated polypeptide" refers to a polypeptide of the invention that is free from at least one contaminating polypeptide that is found in its natural environment, and preferably substantially free from any other contaminating mammalian polypeptides which would interfere with its therapeutic or diagnostic use.

The term "ortholog" refers to a polypeptide that corresponds to a polypeptide identified from a different species. For example, mouse and human JNK activating phosphatase polypeptides are considered orthologs.

The term "mature JNK activating phosphatase polypeptide" refers to a polypeptide lacking a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and the like.

The terms "effective amount" and "therapeutically effective amount" refer to the amount of a JNK activating phosphatase polypeptide that is useful or necessary to support an observable level of one or more biological activities of the JNK activating phosphatase polypeptides as set forth above.

Relatedness of Nucleic Acid Molecules and/or Polypeptides

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i.e., "algorithms").

The term "similarity" is a related concept, but in contrast to "identity," refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10/20 identical amino acids, and the remainder are all non-conservative is substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptide sequences will be higher than the percent identity between those two sequences.

The term "conservative amino acid substitution" refers to a substitution of a native amino acid residue with a nonnative residue such that there is little or no effect on the polarity or charge of the amino acid residue at that position. For example, a conservative substitution results from the replacement of a non-polar residue in a polypeptide with any other non-polar residue. Furthermore, any native residue in the polypeptide may also be substituted with alanine, as has been previously described for "alanine scanning mutagenesis." General rules for conservative amino acid substitutions are set forth in Table I.

TABLE I

Conservative Amino Acid Substitutions

| Original Residues | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala, Tyr | Leu |
| Pro | Ala | Ala |
| Ser | Thr | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Conservative modifications to the amino acid sequence (and the corresponding modifications to the encoding nucleotides) are expected to produce JNK activating phosphatase polypeptide having functional and chemical characteristics similar to those of naturally occurring JNK activating phosphatase polypeptide. In contrast, substantial modifications in the functional and/or chemical characteristics of JNK activating phosphatase polypeptide may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human JNK activating phosphatase molecule that are homologous with non-human JNK activating phosphatase polypeptide, or into the non-homologous regions of the molecule.

Identity and similarity of related nucleic acid molecules and polypeptides can be readily calculated by known methods, including but not limited to those described in *Computational Molecular Biology* (A. M. Lesk, ed., Oxford University Press 1988); *Biocomputing: Informatics and*

*Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., *SIAM J. Applied Math.*, 48: 1073 (1988).

Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux et al., *Nuc. Acids Res.* 12:387 (1984); Genetics Computer Group, University of Wisconsin, Madison, Wis.), BLASTP, BLASTN, and FASTA (Atschul et al., *J. Mol. Biol.* 215: 403–10 (1990)). The BLAST X program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

By way of example, using the computer algorithm GAP (Genetics Computer Group), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. A standard comparison matrix (see Dayhoffet al., 5 *Atlas of Protein Sequence and Structure* (Supp. 3 1978) for the PAM250 comparison matrix; see Henikoff et al., *Proc. Natl. Acad. Sci USA* 89:10915–19 (1992) for the BLOSUM 62 comparison matrix) is also used by the algorithm.

Preferred parameters for polypeptide sequence comparison include the following:
Algorithm: Needleman and Wunsch, *J. Mol. Biol.* 48:443–53 (1970)
Comparison matrix: BLOSUM 62 from Henikoffet al., *Proc. Natl. Acad. Sci. U.S.A.* 89:10915–19 (1992)
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman et al., *J. Mol Biol.* 48:443–53 (1970)
Comparison matrix: matches=+10, mismatch=0
Gap Penalty: 50
Gap Length Penalty: 3

The GAP program is also useful with the above parameters. The aforementioned parameters are the default paraneters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Sequence analysis of an isolated mouse cDNA (mouse JNK activating phosphatase-like protein; SEQ ID NO: 2) indicated that it encoded a novel member of the FGF family of proteins. The mouse JNK activating phosphatase-like gene comprises a 615 bp open reading frame (SEQ ID NO: 3) encoding a protein of 205 amino acids (SEQ ID NO: 4) (FIG. 2). The mouse sequence was used to identify the human JNK activating phosphatase-like ortholog. Sequence analysis of a human JNK activating phosphatase-like polypeptide cDNA clone indicated that the human JNK activating phosphatase-like gene comprises a 615 bp open reading frame (SEQ ID NO: 1) encoding a protein of 205 amino acids (FIG. 1) (SEQ ID NO: 2).

Figure 3A:
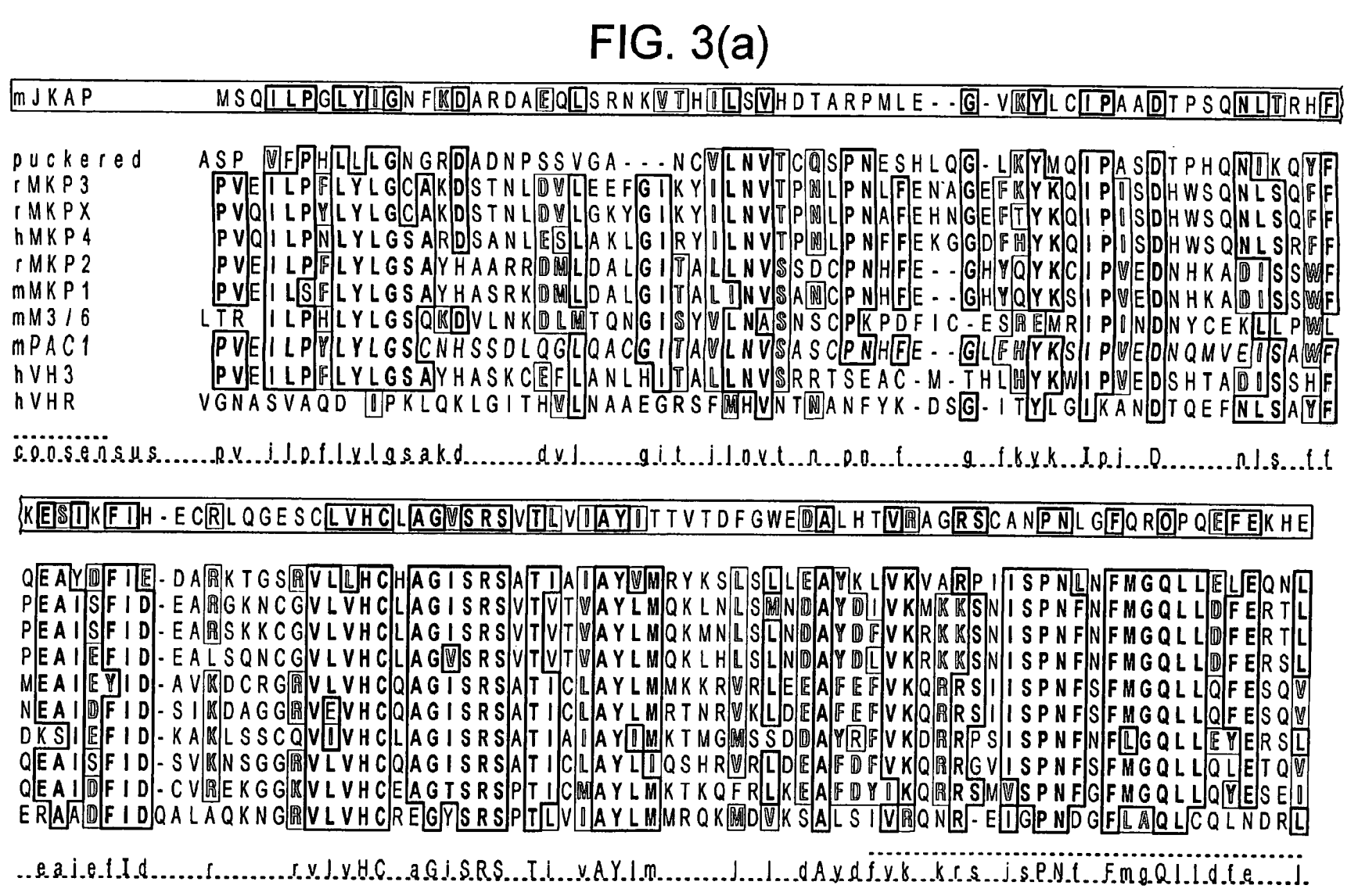

FIG. 3(A) illustrates the amino acid sequence alignment of human JNK activating phosphatase, mouse JNK activating phosphatase, and select MAPK phosphatases. Computer analysis of the predicted mouse JNK activating phosphatase-like polypeptide, using the PIMA 1.4 program of the Institute of Medical Genetics (URL Dot.imgen.bcm.ttmc.edu: 9331/multi-align/multi-align.html Baylor College of Medicine Search Launcher) database, indicated that the protein was most closely related to HVHR. Using the GAP program, mouse JNK activating phosphatase-like polypeptide was found to be 32% identical to HVHR The mouse JNK activating phosphatase-like polypeptide is 89% identical to the human JNK activating phosphatase-like protein.

Nucleic Acid Molecules

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994).

The invention provides for nucleic acid molecules as described herein and methods for obtaining the molecules. A gene or cDNA encoding an JNK activating phosphatase polypeptide or fragment thereof may be obtained by hybridization screening of a genomic or cDNA library, or by PCR amplification. Probes or primers useful for screening a library by hybridization can be generated based on sequence information for other known genes or gene fragments from the same or a related family of genes, such as, for example, conserved motifs. In addition, where a gene encoding JNK activating phosphatase polypeptide has been identified from one species, all or a portion of that gene may be used as a probe to identify corresponding genes from other species (orthologs) or related genes from the same species (homologs). The probes or primers may be used to screen cDNA libraries from various tissue sources believed to express the JNK activating phosphatase gene. In addition, part or all of a nucleic acid molecule having the sequence as set forth in SEQ ID NOS: 1 or 2 may be used to screen a genomic library to identify and isolate a gene encoding JNK activating phosphatase polypeptide. Typically, conditions of moderate or high stringency will be employed for screening to minimize the number of false positives obtained from the screen.

Nucleic acid molecules encoding JNK activating phosphatase polypeptides may also be identified by expression cloning which employs detection of positive clones based upon a property of the expressed protein. Typically, nucleic acid libraries are screened by binding an antibody or other binding partner (e.g., receptor or ligand) to cloned proteins which are expressed and displayed on the host cell surface. The antibody or binding partner is modified with a detectable label to identify those cells expressing the desired clone.

Another means of preparing a nucleic acid molecule encoding an JNK activating phosphatase polypeptide or fragment thereof is chemical synthesis using methods well known to the skilled artisan such as those described by Engels et al., *Angew. Chem. Intl. Ed.* 28:716–34 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the JNK activating phosphatase polypeptide will be several hundred nucleotides in length. Nucleic acids larger than about 100 nucleotides can be synthesized as several fragments using these methods. The fragments can then be ligated together to form the full-length JNK activating phosphatase polypeptide. Usually, the DNA fragment encoding the amino terminus of the polypeptide will have an ATG, which encodes a methionine residue. This methionine may or may not be present on the mature form of the JNK activating phosphatase polypeptide, depending on whether the polypeptide produced in the host cell is designed to be secreted from that cell.

In some cases, it may be desirable to prepare nucleic acid molecules encoding JNK activating phosphatase polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

In certain embodiments, nucleic acid variants contain codons which have been altered for optimal expression of an JNK activating phosphatase polypeptide in a given host cell. Particular codon alterations will depend upon the JNK activating phosphatase polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Ecohigh._Cod" for codon preference of highly expressed bacterial genes may be used and are provided by the University of Wisconsin Package Version 9.0, Genetics Computer Group, Madison, Wis. Other useful codon frequency tables include "Celegans_high.cod," "Celegans_low.cod," "*Drosophila*_high.cod," "Human_high.cod," "Maize_high.cod," and "Yeast_high.cod."

In other embodiments, nucleic acid molecules encode JNK activating phosphatase variants with conservative amino acid substitutions as defined above, JNK activating phosphatase variants comprising an addition and/or a deletion of one or more N-linked or O-linked glycosylation sites, JNK activating phosphatase variants having deletions and/or substitutions of one or more cysteine residues, or JNK activating phosphatase polypeptide fragments as described above. In addition, nucleic acid molecules may encode any combination of JNK activating phosphatase variants, fragments, and fusion polypeptides described herein.

Vectors and Host Cells

A nucleic acid molecule encoding an JNK activating phosphatase polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding an JNK activating phosphatase polypeptide may be amplified/expressed in prokaryotic, yeast, insect (baculovirus systems) and/or eukaryotic host cells. Selection of the host cell will depend in part on whether an JNK activating phosphatase polypeptide is to be post-translationally modified (e.g., glycosylated and/or phosphorylated). If so, yeast, insect, or mammalian host cells are preferable. For a review of expression vectors, see 185 *Meth. Enz.* (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotides: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag" sequence, i.e., an oligonucleotide molecule located at the 5' or 3' end of the JNK activating phosphatase polypeptide coding sequence; the oligonucleotide molecule encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as a means for affinity purification of the JNK activating phosphatase polypeptide from the host cell. Affinity purification can be accomplished, for example, by column chromatography using antibodies against the tag as an affinity matrix. Optionally, the tag can subsequently be removed from the purified JNK activating phosphatase polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or native sequences which normally function to regulate JNK activating phosphatase expression. As such, the source of flanking sequences may be any prokaryotic or eukaryotic organism, any vertebrate or invertebrate organism, or any plant, provided that the flanking sequences is functional in, and can be activated by, the host cell machinery.

The flanking sequences useful in the vectors of this invention may be obtained by any of several methods well known in the art Typically, flanking sequences useful herein other than the JNK activating phosphatase gene flanking sequences will have been previously identified by mapping and/or by restriction endonuclease digestion and can thus be isolated from the proper tissue source using the appropriate restriction endonucleases. In some cases, the full nucleotide sequence of one or more flanking sequence may be known. Here, the flanking sequence may be synthesized using the methods described above for nucleic acid synthesis or cloning.

Where all or only a portion of the flanking sequence is known, it may be obtained using PCR and/or by screening a genomic library with suitable oligonucleotide and/or flanking sequence fragments from the same or another species.

Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography, or other methods known to the skilled artisan. Selection of suitable enzymes to accomplish this purpose will be readily apparent to one of ordinary skill in the art.

An origin of replication is typically a part of prokaryotic expression vectors purchased commercially, and aids in the amplification of the vector in a host cell. Amplification of the vector to a certain copy number can, in some cases, be important for optimal expression of the JNK activating phosphatase polypeptide. If the vector of choice does not contain an origin of replication site, one may be chemically synthesized based on a known sequence, and ligated into the vector.

The origin of replication from the plasmid pBR322 (Product No. 303-3s, New England Biolabs, Beverly, Mass.) is suitable for most Gram-negative bacteria and various origins (e.g., SV40, polyoma, adenovirus, vesicular stomatitis virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding regions and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, for example, ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure that only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes JNK activating phosphatase polypeptide. As a result, increased quantities of JNK activating phosphatase polypeptide are synthesized from the amplified DNA.

A ribosome binding site is usually necessary for translation initiation of mma and is characterized by a Shine-Dalgarno sequence (prokaryotes) or a Kozak sequence (eukaryotes). the element is typically located 3' to the promoter and 5' to the coding sequence of the JNK activating phosphatase polypeptide to be expressed. the Shine-Dalgarno sequence is varied but is typically a polypurine (i.e., having a high a-g content). many Shine-Dalgarno sequences have been identified, each of which can be readily synthesized using methods set forth above and used in a prokaryotic vector.

In many cases, transcription of a nucleic acid molecule is increased by the presence of one or more introns in the vector, this is particularly true where a polypeptide is produced in eukaryotic host cells, especially mammalian host cells. The introns used may be naturally occurring within the JNK activating phosphatase gene especially where the gene used is a full-length genomic sequence or a fragment thereof. Where the intron is not naturally occurring within the gene (as for most cDNAs), the intron may be obtained from another source. The position of the intron with respect to flanking sequences and the JNK activating phosphatase gene is generally important, as the intron must be transcribed to be effective. Thus, when an JNK activating phosphatase cDNA molecule is being expressed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the JNK activating phosphatase protein. Promoters are untranslated sequences located upstream (i.e., 5') to the start codon of a structural gene (generally within about 100 to 1000 bp) that control the transcription and translation of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding JNK activating phosphatase polypeptide by removing the promoter from the source DNA by restriction enzyme digestion and inserting the desired promoter sequence into the vector. The native JNK activating phosphatase promoter sequence may be used to direct amplification and/or expression of JNK activating phosphatase DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any required restriction sites.

Suitable promoters for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling JNK activating phosphatase gene expression include, but are not limited to: the SV40 early promoter region (Bernoist and Chambon, *Nature* 290:304–10 (1981)); the CMV promoter, the promoter contained in the 3' long terminal repeat of Rous sarcoma virus (Yamamoto, et al., *Cell* 22:787–97 (1980)); the herpes thymidine kinase promoter (Wagner et al., *Proc. Natl. Acad. Sci. U.S.A.* 78:1444–45 (1981)); the regulatory sequences of the metallothionine gene (Brinster et al., *Nature* 296:39–42 (1982)); prokaryotic expression vectors such as the beta-lactamase promoter (Villa-Kamaroffet al., *Proc. Natl. Acad. Sci. U.S.A.*, 75:3727–31 (1978)); or the tac promoter (DeBoer et al., *Proc. Natl. Acad. Sci. U.S.A.*, 80:21–25 (1983)). Also of interest are the following animal transcriptional control regions, which exhibit tissue specificity and have been utilized in transgenic animals: the elastase I gene control region which is active in pancreatic acinar cells (Swift et al., *Cell* 38:639–46 (1984); Ornitz et al., *Cold Spring Harbor Symp. Quant. Biol.* 50:399–409 (1986); MacDonald, *Hepatology* 7:425–515 (1987)); the insulin gene control region which is active in pancreatic beta cells (Hanahan, *Nature* 315:115–22 (1985)); the immunoglobulin gene control region which is active in lymphoid cells (Grosschedl et al., *Cell* 38:647–58 (1984); Adames et al., *Nature* 318:533–38 (1985); Alexander et al., *Mol. Cell. Biol.*, 7:1436–44 (1987)); the mouse mammary tumor virus control region which is active in testicular, breast, lymphoid and mast cells (Leder et al., *Cell* 45:485–95 (1986)); the albumin gene control region which is active in liver (Pinkert et al., *Genes and Devel.* 1:268–76 (1987)); the alpha-feto-protein gene control region which is active in liver (Krumlaufet al., *Mol. Cell. Biol.*, 5:1639–48 (1985); Hammer etal., *Science* 235: 53–58 (1987)); the alpha 1-antitrypsin gene control region which is active in the liver (Kelsey et al., *Genes and Devel.* 1: 161–71, 1987)); the beta-globin gene control region which is active in myeloid cells (Mogram et al., *Nature* 315:338–40 (1985); Kollias et al., *Cell* 46:89–94 (1986)); the myelin basic protein gene control region which is active in oligodendrocyte cells in the brain (Readhead et al., *Cell* 48:703–12 (1987)); the myosin light chain-2 gene control region which is active in skeletal muscle (Sani, *Nature* 314:283–86 (1985)); and the gonadotropic releasing hormone gene control region which is active in the hypothalamus (Mason et al., *Science* 234:1372–78 (1986)).

An enhancer sequence may be inserted into the vector to increase the transcription of a DNA encoding an JNK activating phosphatase protein of the present invention by higher eukaryotes. Enhancers are cis-acting elements of DNA, usually about 10–300 bp in length, that act on the promoter to increase its transcription. Enhancers are relatively orientation and position independent They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to JNK activating phosphatase DNA, it is typically located at a site 5' from the promoter.

Expression vectors of the invention may be constructed from starting vectors such as a commercially available vector. Such vectors may or may not contain all of the desired flanking sequences. Where one or more of the flanking sequences set forth above are not already present in the vector to be used, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Publication No. WO90/14363) and pFastBacDual (Gibco-BRL, Grand Island, N.Y.).

Additional possible vectors include, but are not limited to, cosmids, plasmids, or modified viruses, but the vector system must be compatible with the selected host cell. Such vectors include, but are not limited to plasmids such as BLUESCRIPT® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

After the vector has been constructed and a nucleic acid molecule encoding an JNK activating phosphatase polypeptide has been inserted into the proper site of the vector, the completed vector may be inserted into a suitable host cell for amplification and/or polypeptide expression.

Host cells may be prokaryotic host cells (such as *E. coli*) or eukaryotic host cells (such as a yeast cell, an insect cell, or a vertebrate cell). The host cell, when cultured under appropriate conditions, synthesizes an JNK activating phosphatase polypeptide which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), Manassas, Va. Examples include mammalian cells, such as Chinese hamster ovary cells (CHO) (ATCC No. CCL61) CHO DHFR-cells (Urlaub et al., *Proc. Natl. Acad. Sci. U.S.A.* 97:4216–20 (1980)), human embryonic kidney.(HEK) 293 or 293T cells (ATCC No. CRL1573), or 3T3 cells (ATCC No. CCL92). The selection of suitable mammalian host cells and methods for transformation, culture, amplification, screening, product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines (ATCC). Each of these cell lines is known by and available to those skilled in the art of protein expression.

Similarly useful as host cells suitable for the present invention are bacterial cells. For example, the various strains of *E. coli* (e.g., HB101, ATCC No. 33694; DH5; DH10; and MC1061, ATCC No. 53338) are well known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast cells include, for example, *Saccharomyces cerivisae.*

Additionally, where desired, insect cell systems may be utilized in the methods of the present invention. Such systems are described, for example, in Kitts et al., *Biotechniques*, 14:8 10–17 (1993); Lucklow, *Curr. Opin. Biotechnol.* 4:564–72 (1993); and Lucklow et al., *J. Virol.*, 67:4566–79 (1993). Preferred insect cells are Sf-9 and Hi5 (Invitrogen).

Transformation or transfection of an expression vector for an JNK activating phosphatase polypeptide into a selected host cell may be accomplished by well known methods including methods such as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

Polypeptide Production

Host cells comprising an JNK activating phosphatase polypeptide expression vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanauycin. Other compounds for selective growth include ampicillin, tetracycline, and neomycin.

The amount of an JNK activating phosphatase polypeptide produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If an JNK activating phosphatase polypeptide has been designed to be secreted from the host cells, the majority of polypeptide may be found in the cell culture medium. If however, the JNK activating phosphatase polypeptide is not secreted from the host cells, it will be present in the cytoplasm and/or the nucleus (for eukaryotic host cells) or in the cytosol (for gram-negative bacteria host cells).

For an JNK activating phosphatase polypeptide situated in the host cell cytoplasm and/or nucleus, the host cells are typically first disrupted mechanically or with detergent to release the intra-cellular contents into a buffered solution. JNK activating phosphatase polypeptide can then be isolated from this solution.

Purification of an JNK activating phosphatase polypeptide from solution can be accomplished using a variety of techniques. If the polypeptide has been synthesized such that it contains a tag such as Hexahistidine (JNK activating phosphatase polypeptide/hexaHis) or other small peptide such as FLAG (Eastman Kodak Co., New Haven, Conn.) or myc (Invitrogen) at either its carboxyl or amino terminus, it may essentially be purified in a one-step process by passing the solution through an affinity column where the column matrix has a high affinity for the tag or for the polypeptide directly (i.e., a monoclonal antibody specifically recognizing JNK activating phosphatase polypeptide). For example, polyhistidine binds with great affinity and specificity to nickel and thus an affinity column of nickel (such as the Qiagen® nickel columns) can be used for purification of JNK activating phosphatase polypeptide/polyHis. See, e.g., *Current Protocols in Molecular Biology* § 10.11.8 (Ausubel et al., eds., John Wiley & Sons 1993).

Where an JNK activating phosphatase polypeptide is prepared without a tag attached, and no antibodies are available, other well-known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If an JNK activating phosphatase polypeptide is produced intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If an JNK activating phosphatase polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The JNK activating phosphatase polypeptide in its now soluble form can then be analyzed using gel electrophoresis, immunoprecipitation, or the like. If it is desired to isolate the JNK activating phosphatase polypeptide, isolation may be accomplished using standard methods such as those set forth below and in Marston et al., *Meth. Enz.*, 182:264–75 (1990).

In some cases, an JNK activating phosphatase polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the so lubilization. In most cases the refoldingtoxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothbeitol(DTT)/dithiane DOT, and 2-mercaptoethanol(bME)/dithio-b(ME). In many instances, a cosolvent may be used or may be needed to increase the efficiency of the refolding and the more common reagents used for this purpose include glycerol, polyethylene glycol of various molecular weights, arginine and the like.

If inclusion bodies are not formed to a significant degree upon expression of an JNK activating phosphatase polypeptide, the polypeptide will be found primarily in the supernatant after centrifugation of the cell homogenate and may be further isolated from the supernatant using methods such as those set forth below.

In situations where it is preferable to partially or completely purify an JNK activating phosphatase polypeptide such that it is partially or substantially free of contaminants, standard methods known to the one skilled in the art may be used. Such methods include, without limitation, separation by electrophoresis followed by electroelution, various types of chromatography (affinity, immunoaffinity, molecular sieve, and/or ion exchange), and/or high pressure liquid chromatography. In some cases, it may be preferable to use more than one of these methods for complete purification.

JNK activating phosphatase polypeptides, fragments, and/or derivatives thereof may also be prepared by chemical synthesis methods (such as solid phase peptide synthesis) using techniques known in the art such as those set forth by Merrifield et al., *J. Am. Chem. Soc.* 85:2149 (1963); Houghten et al., *Proc Natl Acad. Sci. USA* 82:5132 (1985); and Stewart and Young, *Solid Phase Peptide Synthesis* (Pierce Chemical Co. 1984). Such polypeptides may be synthesized with or without a methionine on the amino terminus. Chemically synthesized JNK activating phosphatase polypeptides or fragments may be oxidized using methods set forth in these references to form disulfide bridges. JNK activating phosphatase polypeptides, fragments or derivatives are expected to have comparable biological activity to the corresponding JNK activating phosphatase polypeptides, fragments or derivatives produced recombinantly or purified from natural sources, and thus may be used interchangeably with recombinant or natural JNK activating phosphatase polypeptide.

Another means of obtaining JNK activating phosphatase polypeptide is via purification from biological samples such as source tissues and/or fluids in which the JNK activating phosphatase polypeptide is naturally found. Such purification can be conducted using methods for protein purification as described above. The presence of the JNK activating phosphatase polypeptide during purification may be monitored using, for example, an antibody prepared against recombinantly produced JNK activating phosphatase polypeptide or peptide fragments thereof.

Polypeptides

Polypeptides of the invention include isolated JNK activating phosphatase polypeptides and polypeptides related thereto including fragments, variants, fusion polypeptides, and derivatives as defined hereinabove.

JNK activating phosphatase polypeptide fragments of the invention may result from truncations at the amino terminus (with or without a leader sequence), truncations at the carboxyl terminus, and/or deletions internal to the polypeptide. In preferred embodiments, truncations and/or deletions comprise about 10 amino acids, or about 20 amino acid, or about 50 amino acids, or about 75 amino acids, or about 100 amino acids, or more than about 100 amino acids. The polypeptide fragments so produced will comprise about 25 contiguous amino acids, or about 50 amino acids, or about 75 aminio acids, or about 100 amino acids, or about 150 amino acids, or about 200 amino acids. Such JNK activating phosphatase polypeptide fragments may optionally comprise an amino terminal methionine residue.

JNK activating phosphatase polypeptide variants of the invention include one or more amino acid substitutions, additions and/or deletions as compared to SEQ ID NOS: 2 or 4. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, as defined above, or non-conservative or any combination thereof. The variants may have additions of amino acid residues either at the carboxyl terminus or at the amino terminus (with or without a leader sequence).

Preferred JNK activating phosphatase variants include cysteine variants, wherein one or more cysteine residues are deleted or substituted with another amino acid (e.g., serine). Cysteine variants are useful when JNK activating phosphatase polypeptide must be refolded into a biologically active conformation such as after isolation of insoluble inclusive bodies. Cysteine variants generally have fewer cysteine residues than the native protein, and typically have an even number to minimize interactions resulting from unpaired cysteines.

One skilled in the art will be able to determine suitable variants of the native JNK activating phosphatase polypeptide using well-known techniques. For example, one may be able to predict suitable areas of the molecule that may be changed without destroying biological activity. Also, one skilled in the art will realize that even areas that may be important for biological activity or for structure may be subject to conservative amino acid substitutions without destroying the biological activity or without adversely affecting the polypeptide structure.

For predicting suitable areas of the molecule that may be changed without destroying activity, one skilled in the art may target areas not believed to be important for activity. For example, when similar polypeptides with similar activities from the same species or from other species are known, one skilled in the art may compare the amino acid sequence of JNK activating phosphatase polypeptide to such similar polypeptides. After making such a comparison, one skilled in the art would be able to determine residues and portions of the molecules that are conserved among similar polypeptides. One skilled in the art would know that changes in areas of the JNK activating phosphatase molecule that are not conserved would be less likely to adversely affect biological activity and/or structure. One skilled in the art would also know that, even in relatively conserved regions, one could have likely substituted chemically similar amino acids for the naturally occurring residues while retaining activity (conservative amino acid residue substitutions).

Also, one skilled in the art may review structure-function studies identifying residues in similar polypeptides that are important for activity or structure. In view of such a comparison, one skilled in the art can predict the importance of amino acid residues in JNK activating phosphatase polypeptide that correspond to amino acid residues that are important for activity or structure in similar polypeptides. One skilled in the art may opt for chemically similar amino acid substitutions for such predicted important amino acid residues of JNK activating phosphatase polypeptide.

If available, one skilled in the art can also analyze the three-dimensional structure and amino acid sequence in relation to that structure in similar polypeptides. In view of that information, one skilled in the art may be able to predict the alignment of amino acid residues of JNK activating phosphatase polypeptide with respect to its three dimensional structure. One skilled in the art may choose not to make radical changes to amino acid residues predicted to be on the surface of the protein, since such residues may be involved in important interactions with other molecules.

Moreover, one skilled in the art could generate test variants containing a single amino acid substitution at each amino acid residue. The variants could be screened using activity assays disclosed in this application. Such variants could be used to gather information about suitable variants. For example, if one discovered that a change to a particular amino acid residue resulted in destroyed activity, variants with such a change would be avoided. In other words, based on information gathered from such experiments, when attempting to find additional acceptable variants, one skilled in the art would have known the amino acids where further substitutions should be avoided either alone or in combination with other mutations.

JNK activating phosphatase fusion polypeptides of the invention comprise JNK activating phosphatase polypeptides, fragments, variants, or derivatives fused to a heterologous peptide or protein. Heterologous peptides and proteins include, but are not limited to: an epitope to allow for detection and/or isolation of an JNK activating phosphatase fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a protein or peptide which promotes oligomerization, such as leucine zipper domain; and a protein or peptide which increases stability, such as an immunoglobulin constant region. An JNK activating phosphatase polypeptide may be fused to itself or to a fragment, variant, or derivative thereof. Fusions may be made either at the amino terminus or at the carboxyl terminus of an JNK activating phosphatase polypeptide, and may be direct with no linker or adapter molecule or may be through a linker or adapter molecule, such as one or more amino acid residues up to about 20 amino acids residues, or up to about 50 amino acid residues. A linker or adapter molecule may also be designed with a cleavage site for a DNA restriction endonuclease or for a protease to allow for separation of the fused moieties.

In a further embodiment of the invention, an JNK activating phosphatase polypeptide, fragment, variant and/or derivative is fused to an Fc region of human IgG. In one example, a human IgG hinge, CH2 and CH3 region may be fused at either the N-terminus or C-terminus of the JNK activating phosphatase polypeptides using methods known to the skilled artisan. In another example, a portion of a hinge regions and CH2 and CH3 regions may be fused. The JNK activating phosphatase Fc-fusion polypeptide so produced may be purified by use of a Protein A affinity column. In addition, peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduced aggregation, etc.

JNK activating phosphatase polypeptide derivatives are included in the scope of the present invention. Such derivatives are chemically modified JNK activating phosphatase polypeptide compositions in which JNK activating phosphatase polypeptide is linked to a polymer. The polymer selected is typically water-soluble so that the protein to which it is attached does not precipitate in an aqueous environment, such as a physiological environment. The polymer may be of any molecular weight, and may be branched or unbranched. Included within the scope of JNK activating phosphatase polypeptide polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran (such as low molecular weight dextran, of, for example about 6 kD), cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the invention are bifunctional PEG cross-linking molecules that may be used to prepare covalently attached JNK activating phosphatase polypeptide multimers For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono C1–C10 alkoxy or aryloxy derivatives thereof (see U.S. Pat. No. 5,252,714).

Pegylation of JNK activating phosphatase polypeptides may be carried out by any of the pegylation reactions known in the art, as described for example in the following references: Francis et al., Focus on Growth Factors 3, 4–10 (1992); EP 0154 316; EP 0 401 384 and U.S. Pat. No. 4,179,337. Pegylation may be carried out via an acylation reaction or an alkylation reaction with a reactive polyethylene glycol molecule (or an analogous reactive water-soluble polymer) as described below.

One water-soluble polymer for use herein is polyethylene glycol, abbreviated PEG. As used herein, polyethylene glycol is meant to encompass any of the forms of PEG that have been used to derivatize other proteins, such as mono-(C1–$C_{10}$) alkoxy- or aryloxy-polyethylene glycol.

In general, chemical derivatization may be performed under any suitable conditions used to react a biologically active substance with an activated polymer molecule. Methods for preparing pegylated JNK activating phosphatase polypeptides will generally comprise the steps of (a) reacting the polypeptide with polyethylene glycol (such as a reactive ester or aldehyde derivative of PEG) under conditions whereby JNK activating phosphatase polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

In a preferred embodiment, the JNK activating phosphatase polypeptide derivative will have a single PEG moiety at the amino terminus. See U.S. Pat. No. 5,234,784, herein incorporated by reference.

Generally, conditions that may be alleviated or modulated by administration of the present JNK activating phosphatase polypeptide derivative include those described herein for JNK activating phosphatase polypeptides. However, the JNK activating phosphatase polypeptide derivative disclosed herein may have additional activities, enhanced or reduced biological activity, or other characteristics, such as increased or decreased half-life, as compared to the non-derivatized molecules.

Antibodies

JNK activating phosphatase polypeptides, fragments, variants, and derivatives may be used to prepare antibodies using methods known in the art. Thus, antibodies and antibody fragments that bind JNK activating phosphatase polypeptides are within the scope of the present invention. Antibodies may be polyclonal, monospecific polyclonal, monoclonal, recombinant, chimeric, humanized, fully human, single chain and/or bispecific.

Polyclonal antibodies directed toward an JNK activating phosphatase polypeptide generally are raised in animals (e.g., rabbits or mice) by multiple subcutaneous or intraperitoneal injections of JNK activating phosphatase polypeptide and an adjuvant It may be useful to conjugate an JNK activating phosphatase polypeptide, or a variant, fragment or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-JNK activating phosphatase antibody titer.

Monoclonal antibodies directed toward JNK activating phosphatase polypeptide are produced using any method that provides for the production of antibody molecules by continuous cell lines in culture. Examples of suitable methods for preparing monoclonal antibodies include hybridoma methods of Kohler, et al., Nature 256:495–97 (1975), and the human B-cell hybridoma method, Kozbor, J. Immunol. 133:3001 (1984); Brodeur et al., Monoclonal Antibody Production Techniques and Applications 51–63 (Marcel Dekker 1987).

Also provided by the invention are hybridoma cell lines that produce monoclonal antibodies reactive with JNK activating phosphatase polypeptides. Monoclonal antibodies of the invention may be modified for use as therapeutics. One embodiment is a "chimeric" antibody in which a portion of the heavy and/or light chain is identical with or homologous to corresponding sequence in antibodies derived from a particular species or belonging to a particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity (see U.S. Pat. No. 4,8 16,567; Morrison, et al., Proc. Natl. Acad. Sci. U.S.A. 81: 6851–55 (1985).

In another embodiment, a monoclonal antibody of the invention is a "humanized" antibody. Methods for humanizing non-human antibodies are well known in the art. Generally, a humanized antibody has one or more amino acid residues introduced into it from a source that is non-human. Humanization can be performed following methods known in the art (Jones, et al., Nature 321: 522–25 (1986); Riechmann, et al., Nature 332:323–27 (1988); Verhoeyen et al., Science 239:1534–36 (1988)), by substituting rodent complementarily-determining regions (CDRs) for the-corresponding regions of a human antibody.

Also encompassed by the invention are fully human antibodies that bind JNK activating phosphatase polypeptides, fragments, variants, and/or derivatives. Such antibodies are produced by immunization with an JNK activating phosphatase antigen (optionally conjugated to a carrier) of transgenic animals (e.g., mice) that are capable of producing a repertoire of human antibodies in the absence of endogenous immunoglobulin production. See, e.g., Jakobovits, et al., Proc. Natl. Acad. Sci. U.S.A 90: 2551–55 (1993); Jakobovits, et al., Nature 362:255–58 (1993); Bruggermann et al., Year in Immuno. 7:33 (1993). Human antibodies can also be produced in phagedisplay libraries (Hoogenboom et al., J. Mol. Biol. 227:381 (1991); Marks, et al., J. Mol. Biol. 222:581 (1991)).

The anti-JNK activating phosphatase antibodies of the invention may be employed in any known assay method, such as competitive binding assays, direct and indirect sandwich assays, and immunoprecipitation assays (Sola, Monoclonal Antibodies: A Manual of Techniques 147–58 (CRC Press 1987)) for detection and quantitation of JNK activating phosphatase polypeptides. The antibodies will bind JNK activating phosphatase polypeptides with an affinity that is appropriate for the assay method being employed.

Competitive binding assays rely on the ability of a labeled standard (e.g., an JNK activating phosphatase polypeptide, or an immunologically reactive portion thereof) to compete with the test sample analyte (an JNK activating phosphatase polypeptide) for binding with a limited amount of anti JNK activating phosphatase antibody. The amount of an JNK activating phosphatase polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an ELISA assay, in which case the detectable moiety is an enzyme.

The invention also relates to a kit comprising anti-JNK activating phosphatase antibodies and other reagents useful for detecting JNK activating phosphatase polypeptide levels in biological samples. Such reagents may include a secondary activity, a detectable label, blocking serum, positive and negative control samples and detection reagents.

Genetically Engineered Non-Human Animals

Additionally included within the scope of the present invention are non-human animals such as mice, rats, or other rodents, rabbits, goats, sheep, or other farm animals, in which the gene encoding native JNK activating phosphatase polypeptide has been disrupted (i.e., "knocked out") such that the level of expression of JNK activating phosphatase polypeptide is significantly decreased or completely abolished. Such animals may be prepared using techniques and methods such as those described in U.S. Pat. No. 5,557,032.

The present invention further includes non-human animals such as mice, rats, or other rodents, rabbits, goats, sheep, or other farm animals, in which a gene encoding a native form of JNK activating phosphatase polypeptide for that animal or a heterologous JNK activating phosphatase polypeptide gene is overexpressed by the animal, thereby creating a "transgenic" animal. Such transgenic animals may be prepared using well known methods such as those described in U.S. Pat. No 5,489,743 and PCT Publication No. WO94/28122.

The present invention further includes non-human animals in which the promoter for one or more of the JNK activating phosphatase polypeptides of the present invention is either activated or inactivated (e.g., by using homologous recombination methods as described below) to alter the level of expression of one or more of the native JNK activating phosphatase polypeptides.

Such non-human animals may be used for drug candidate screening. The impact of a drug candidate on the animal may be measured. For example, drug candidates may decrease or increase expression of the JNK activating phosphatase polypeptide gene. In certain embodiments, the amount of JNK activating phosphatase polypeptide or an JNK activating phosphatase polypeptide fragment that is produced may be measured after exposure of the animal to the drug candidate. In certain embodiments, one may detect the actual impact of the drug candidate on the animal. For example, overexpression of a particular gene may result in, or be associated with, a disease or pathological condition. In such cases, one may test a drug candidate's ability to decrease expression of the gene or its ability to prevent or inhibit a pathological condition. In other examples, production of a particular metabolic product such as a fragment of a polypeptide, may result in, or be associated with, a disease or pathological condition. In such cases, one may test a drug candidate's ability to decrease production of such a metabolic product or its ability to prevent or inhibit a pathological condition.

Modulators of JNK Activating Phosphatase Polypeptide Activity

In some situations, it may be desirable to identify molecules that are modulators, i.e., agonists or antagonists, of the activity of JNK activating phosphatase polypeptide.

Natural or synthetic molecules that modulate JNK activating phosphatase polypeptide can be identified using one or more screening assays, such as those described below. Such molecules may be administered either in an ex vivo manner or in an in vivo manner by local or intravenous injection or by oral delivery, implantation device, or the like.

The following definition is used herein for describing the assays:

"Test molecule(s)" refers to the molecule(s) that is/are under evaluation for the ability to modulate (i.e., increase or decrease) the activity of an JNK activating phosphatase polypeptide. Most commonly, a test molecule will interact directly with an JNK activating phosphatase polypeptide. However, it is also contemplated that a test molecule may also modulate JNK activating phosphatase polypeptide activity indirectly, such as by affecting JNK activating phosphatase gene expression, or by binding to an JNK activating phosphatase binding partner (e.g., receptor or ligand). In one embodiment, test molecule will bind to an JNK activating phosphatase polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with JNK activating phosphatase polypeptides are encompassed by the invention. In certain embodiments, an JNK activating phosphatase polypeptide is incubated with a test molecule under conditions that permit interaction of the test molecule with an JNK activating phosphatase polypeptide, and the extent of the interaction can be measured. The test molecule may be screened in a substantially purified form or in a crude mixture. Test molecules may be nucleic acid molecules, proteins, peptides, carbohydrates, lipids, or small molecular weight organic or inorganic compounds. Once a set of test molecules has been identified as interacting with an JNK activating phosphatase polypeptide, the molecules may be further evaluated for their ability to increase or decrease JNK activating phosphatase polypeptide activity.

Measurement of the interaction of test molecules with JNK activating phosphatase polypeptides may be carried out in several formats, including cell-based binding assays, membrane binding assays, solution-phase assays and immunoassays. In general, test molecules are incubated with an JNK activating phosphatase polypeptide for a specified period of time and JNK activating phosphatase polypeptide activity is determined by one or more assays described herein for measuring biological activity.

Interaction of test molecules with JNK activating phosphatase polypeptides may also be assayed directly using polyclonal or monoclonal antibodies in an immunoassay Alternatively, modified forms of JNK activating phosphatase polypeptides containing epitope tags as described above may be used in solution and immunoassays.

In certain embodiments, an JNK activating phosphatase polypeptide agonist or antagonist may be a protein, peptide, carbohydrate, lipid, or small molecular weight molecule that interacts with JNK activating phosphatase polypeptide to regulate its activity. Potential protein antagonists of JNK activating phosphatase polypeptide include antibodies that interest with active regions of the polypeptide and inhibit or eliminate at least one activity of JNK activating phosphatase polypeptide. Molecules which regulate JNK activating phosphatase polypeptide expression may include nucleic acids which are complementary to nucleic acids encoding an JNK activating phosphatase polypeptide, or are complementary to nucleic acids sequences which direct or control expression of JNK activating phosphatase polypeptide, and which act as anti-sense regulators of expression.

In the event that JNK activating phosphatase polypeptides display biological activity through interaction with a binding partner (e.g., a receptor or a ligand), a variety of in vitro assays may be used to measure binding of an JNK activating phosphatase polypeptide to a corresponding binding partner. These assays may be used to screen test molecules for their ability to increase or decrease the rate and/or the extent of binding of an JNK activating phosphatase polypeptide to its binding partner. In one assay, an JNK activating phosphatase polypeptide is immobilized by attachment to the bottom of the wells of a microtiter plate. Radiolabeled JNK activating phosphatase binding partner (for example, iodinated JNK activating phosphatase binding partner) and the test molecules can then be added either one at a time (in either order) or simultaneously to the wells. After incubation, the wells can be washed and counted using a scintillation counter for radioactivity to determine the extent of binding to JNK activating phosphatase protein by its binding partner. Typically, the molecules will be tested over a range of concentrations and a series of control wells lacking one or more elements of the test assays can be used for accuracy in evaluation of the results. An alternative to this method involves reversing the "positions" of the proteins, i.e., immobilizing JNK activating phosphatase binding partner to the microtiter plate wells, incubating with the test molecule and radiolabeled JNK activating phosphatase polypeptide, and determining the extent of JNK activating phosphatase binding (see, e.g., *Current Protocols in Molecular Biology*, chap. 18 (Ausubel et al., eds., John Wiley & Sons 1995)).

As an alternative to radiolabelling, an JNK activating phosphatase polypeptide or its binding partner may be conjugated to biotin and the presence of biotinylated protein can then be detected using streptavidin linked to an enzyme, such as horse radish peroxidase (HRP) or alkaline phosphatase (AP), that can be detected colorometrically, or by fluorescent tagging of streptavidin. An antibody directed to an JNK activating phosphatase polypeptide or to an JNK activating phosphatase binding partner and that is conjugated to biotin may also be used and can be detected after incubation with enzyme-linked streptavidin linked to AP or HRP An JNK activating phosphatase polypeptide and an JNK activating phosphatase binding partner may also be immobilized by attachment to agarose beads, acrylic beads, or other types of such inert substrates. The substrate-protein complex can be placed in a solution containing the complementary protein and the test compound; after incubation, the beads can be precipitated by centrifugation, and the amount of binding between an JNK activating phosphatase polypeptide and its binding partner can be assessed using the methods described above. Alternatively, the substrate-protein complex can be immobilized in a column and the test molecule and complementary protein passed over the column. Formation of a complex between an JNK activating phosphatase polypeptide and its binding partner can then be assessed using any of the techniques set forth above, i.e., radiolabeling, antibody binding, or the like.

Another in vitro assay that is useful for identifying a test molecule which increases or decreases formation of a complex between an JNK activating phosphatase binding protein and an JNK activating phosphatase binding partner is a surface plasmon resonance detector system such as the Biacore assay system (Pharmacia, Piscataway, N.J.). The Biacore system may be carried out using the manufacturer's protocol. This assay essentially involves covalent binding of either JNK activating phosphatase polypeptide or an JNK activating phosphatase binding partner to a dextran-coated sensor chip that is located in a detector. The test compound and the other complementary protein can then be injected into the chamber containing the sensor chip either simultaneously or sequentially and the amount of complementary protein that binds can be assessed based on the change in molecular mass which is physically associated with the dextranuoated side of the sensor chip; the change in molecular mass can be measured by the detector system.

In some cases, it may be desirable to evaluate two or more test compounds together for their ability to increase or decrease formation of a complex between an JNK activating phosphatase polypeptide and an JNK activating phosphatase binding partner complex. In these cases, the assays set forth above can be readily modified by adding such additional test compounds either simultaneous with, or subsequent to, the first test compound. The remaining steps in the assay are as set forth above.

In vitro assays such as those described above may be used advantageously to screen rapidly large numbers of compounds for effects on complex formation by JNK activating phosphatase polypeptide and JNK activating phosphatase binding partner. The assays may be automated to screen compounds generated in phage display, synthetic peptide, and chemical synthesis libraries.

Compounds which increase or decrease formation of a complex between an JNK activating phosphatase polypeptide and an JNK activating phosphatase binding partner may also be screened in cell culture using cells and cell lines expressing either JNK activating phosphatase polypeptide or JNK activating phosphatase binding partner. Cells and cell lines may be obtained from any mammal, but preferably will be from human or other primate, canine, or rodent sources.

Cell cultures can also be used to screen the impact of a drug candidate. For example, drug candidates may decrease or increase expression of the JNK activating phosphatase polypeptide gene. In certain embodiments, the amount of JNK activating phosphatase polypeptide or an JNK activating phosphatase polypeptide fragment that is produced may be measured after exposure of the cell culture to the drug candidate. In certain embodiments, one may detect the actual impact of the drug candidate on the cell culture. For example, overexpression of a particular gene may have a particular impact on the cell culture. In such cases, one may test a drug candidate's ability to increase or decrease expression of the gene or its ability to prevent or inhibit a particular impact on the cell culture. In other examples, production of a particular metabolic product such as a fragment of a polypeptide, may result in, or be associated with, a disease or pathological condition. In such cases, one may test a drug candidate's ability to decrease production of such a metabolic product in a cell culture.

A yeast two hybrid system (Chien et al., *Proc. Natl. Acad. Sci. U.S.A.* 88:9578–83 (1991)) can be used to identify novel polypeptides that bind to, or interact with, JNK activating phosphatase polypeptides. As an example, hybrid constructs comprising DNA encoding a cytoplasmic domain of an JNK activating phosphatase polypeptide fused to a yeast GAL4-DNA binding domain may be used as a two-hybrid bait plasmid. Positive clones emerging from the screening may be characterized further to identify interacting proteins.

Additional objects of the present invention relate to methods for both the in vitro production of therapeutic proteins by means of homologous recombination and for the production and delivery of therapeutic proteins by gene therapy.

It is further envisioned that JNK activating phosphatase protein may be produced by homologous recombination, or with recombinant production methods utilizing control elements introduced into cells already containing DNA encoding JNK activating phosphatase polypeptide. For example, homologous recombination methods may be used to modify a cell that contains a normally transcriptionally silent JNK activating phosphatase gene, or under expressed gene, and thereby produce a cell that expresses therapeutically efficacious amounts of JNK activating phosphatase polypeptide. Homologous recombination is a technique originally developed for targeting genes to induce or correct mutations in transcriptionally active genes (Kucherlapati, *Prog. in Nucl. Acid Res. and Mol. Biol.* 36:301 (1989)). The basic technique was developed as a method for introducing specific mutations into specific regions of the mammalian genome (Thomas et al., *Cell* 44:419–28 (1986); Thomas and Capecchi, *Cell* 51:503–12, (1987); Doetschman et al., *Proc. Natl. Acad. Sci. U.S.A.* 85:8583–87 (1988)) or to correct specific mutations within defective genes (Doetschman et al., *Nature* 330:576–78 (1987)). Exemplary homologous recombination techniques are described in U.S. Pat. No. 5,272,071 (EP Patent No. 91 90 3051, EP Publication No. 505 500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with the expression of a JNK activating phosphatase protein. For example, a promoter/enhancer element, a suppresser, or an exogenous transcription modulatory element is inserted in the genome of the intended host cell in proximity and orientation sufficient to influence the transcription of DNA encoding the desired JNK activating phosphatase protein. The control element controls a portion of the DNA present in the host cell genome. Thus, the expression of JNK activating phosphatase protein may be achieved not by transfection of DNA that encodes the JNK activating phosphatase gene itself, but rather by the use of targeting DNA (containing regions of homology with the endogenous gene of interest) coupled with DNA regulatory segments that provide the endogenous gene sequence with recognizable signals for transcription of a JNK activating phosphatase protein.

In an exemplary method, expression of a desired targeted gene in a cell (i.e., a desired endogenous cellular gene) is altered by the introduction, by homologous recombination into the cellular genome at a preselected site, of DNA which includes at least a regulatory sequence, an exon and a splice donor site. These components are introduced into the chromosomal (genomic) DNA in such a manner that this, in effect, results in production of a new transcription unit (in which the regulatory sequence, the exon, and the splice donor site present in the DNA construct are operatively linked to the endogenous gene). As a result of introduction of these components into the chromosomal DNA, the expression of the desired endogenous gene is altered.

Altered gene expression, as used herein, encompasses activating (or causing to be expressed) a gene which is normally silent (unexpressed) in the cell as obtained, increasing expression of a gene which may include expressing a gene that is not expressed at physiologically significant levels in the cell as obtained, changing the pattern of regulation or induction such that it is different than occurs in the cell as obtained, and reducing (including eliminating) expression of a gene which is expressed in the cell as obtained.

The present invention further relates to DNA constructs useful in the method of altering expression of a target gene. In certain embodiments, the exemplary DNA constructs comprise: (a) a targeting sequence, (b) a regulatory sequence, (c) an exon, and (d) an unpaired splice-donor site. The targeting sequence in the DNA construct directs the integration of elements (a)–(d) into a target gene in a cell such that the elements (b)–(d) are operatively linked to sequences of the endogenous target gene. In another embodiment, the DNA constructs comprise: (a) a targeting sequence, (b) a regulatory sequence, (c) an exon, (d) a splice-donor site, (e) an intron, and (f) a splice-acceptor site, wherein the targeting sequence directs the integration of elements (a)–(f) such that the elements of (b)–(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of JNK activating phosphatase polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA. The present invention, therefore, includes nucleotides encoding a JNK activating phosphatase molecule, which nucleotides may be used as targeting sequences.

In vivo and in vitro gene therapy delivery of JNK activating phosphatase polypeptide is also envisioned. In vivo gene therapy may be accomplished by introducing the gene encoding JNK activating phosphatase polypeptide into cells via local injection of a polynucleotide molecule or other appropriate delivery vectors (Hefti, *J. Neurobiology* 25:1418–35 (1994)). For example, a polynucleotide molecule encoding JNK activating phosphatase protein may be contained in an adeno-associated virus vector for delivery to the targeted cells (see, e.g., Johnson, PCT Publication No. WO 95/34670; PCT Application No. PCT/US95/07178). The recombinant adeno-associated virus (AAV) genome typically contains AAV inverted terminal repeats flanking a DNA sequence encoding JNK activating phosphatase polypeptide operably linked to functional promoter and polyadenylation sequences.

Alternative viral vectors include, but are not limited to, retrovirus, adenovirus, herpes simplex virus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors); U.S. Pat. No. 5,672,510 (involving retroviral vectors); and U.S. Pat. No. 5,635,399 (involving retroviral vectors expressing cytokines).

Nonviral delivery methods include liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, transcription factors to enhance expression by a vector as well as methods of vector manufacture. Such additional methods and materials for the practice of gene therapy techniques are described in U.S. Pat. No. 4,970,154 (electroporation techniques); PCT Application No. WO 96/40958 (nuclear ligands); U.S. Pat. No. 5,679,559 (concerning a lipoprotein-containing system for gene delivery); U.S. Pat. No. 5,676,954 (involving liposome carriers); U.S. Pat. No. 5,593,875 (concerning methods for calcium phosphate transfection); and U.S. Pat. No. 4,945,050 (wherein biologically active particles are propelled at cells at a speed whereby the particles penetrate the surface of the cells and become incorporated into the interior of the cells). Expression control techniques include chemical induced regulation (see, e.g., PCT Application Nos. WO 96/41865 and WO 97/31899), the use of a progesterone antagonist in a modified steroid hormone receptor system (see, e.g., U.S. Pat. No. 5,364,791), ecdysone control systems (see, e.g., PCT Application No. WO 96/37609), and positive tetracycline-controllable transactivators (see, e.g., U.S. Pat. No. 5,589,362; U.S. Pat. No. 5,650,298; and U.S. Pat. No. 5,654,168).

One manner in which gene therapy can be applied is to use the JNK activating phosphatase gene (either genomic DNA, cDNA, and/or synthetic DNA encoding a JNK activating phosphatase polypeptide, or a fragment, variant, or derivative thereof) which may be operably linked to a constitutive or inducible promoter to form a "gene therapy DNA construct." The promoter may be homologous or heterologous to the endogenous JNK activating phosphatase gene, provided that it is active in the cell or tissue type into which the construct will be inserted. Other components of the gene therapy DNA construct may optionally include: DNA molecules designed for site-specific integration (e.g., endogenous flanking sequences useful for homologous recombination), a tissue-specific promoter, enhancers, silencers, DNA molecules capable of providing a selective advantage over the parent cell, DNA molecules useful as labels to identify transformed cells, negative selection systems, cell specific binding agents (as, for example, for cell targeting), cell-specific internalization factors, and transcription factors to enhance expression by a vector as well as factors to enable vector manufacture.

This gene therapy DNA construct can then be introduced into the patient's cells (either ex vivo or in vivo). One means for introducing the gene therapy DNA construct is via viral vectors. Suitable viral vectors typically used in gene therapy for delivery of gene therapy DNA constructs include, without limitation, adenovirus, adeno-associated virus, herpes simplex virus, lentivirus, papilloma virus, and retrovirus vectors. Some of these vectors, such as retroviral vectors, will deliver the gene therapy DNA construct to the chromosomal DNA of the patient's cells, and the gene therapy DNA construct can integrate into the chromosomal DNA; other vectors will function as episomes and the gene therapy DNA construct will remain in the cytoplasm.

Another means to increase endogenous JNK activating phosphatase polypeptide expression in a cell via gene therapy is to insert one or more enhancer elements into the JNK activating phosphatase polypeptide promoter, where the enhancer elements can serve to increase transcriptional activity of the JNK activating phosphatase polypeptide gene. The enhancer elements used will be selected based on the tissue in which one desires to activate the gene-enhancer elements known to confer-promoter activation in that tissue will be selected. For example, if a gene encoding an JNK activating phosphatase polypeptide is to be "turned on" in T-cells, the lck promoter enhancer element may be used. Here, the functional portion of the transcriptional element to be added may be inserted into a fragment of DNA containing the JNK activating phosphatase polypeptide promoter (and optionally, inserted into a vector and/or 5' and/or 3' flanking sequences, etc.) using standard cloning techniques. This construct, known as a "homologous recombination construct," can then be introduced into the desired cells either ex vivo or in vivo.

Gene therapy can be used to decrease JNK activating phosphatase polypeptide expression by modifying the nucleotide sequence of the endogenous promoter. Such modification is typically accomplished via homologous recombination methods. For example, a DNA molecule containing all or a portion of the promoter of the JNK activating phosphatase gene selected for inactivation can be engineered to remove and/or replace pieces of the promoter that regulate transcription. Here, for example, the TATA box and/or the binding site of a transcriptional activator of the promoter may be deleted using standard molecular biology techniques; such deletion can inhibit promoter activity thereby repressing transcription of the corresponding JNK activating phosphatase gene. Deletion of the TATA box or transcription activator binding site in the promoter may be accomplished by generating a DNA construct comprising all or the relevant portion of the JNK activating phosphatase polypeptide promoter (from the same or a related species as the JNK activating phosphatase gene to be regulated) in which one or more of the TATA box and/or transcriptional activator binding site nucleotides are mutated via substitution, deletion and/or insertion of one or more nucleotides such that the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described above. Typically, integration of the construct into the genomic DNA of the cells will be via homologous recombination, where the 5' and 3' DNA sequences in the promoter construct can serve to help integrate the modified promoter region via hybridization to the endogenous chromosomal DNA.

Other gene therapy methods may also be employed where it is desirable to inhibit the activity of one or more JNK activating phosphatase polypeptides. For example, antisense DNA or RNA molecules, which have a sequence that is complementary to at least a portion of the selected JNK activating phosphatase polypeptide gene can be introduced into the cell. Typically, each such antisense molecule will be complementary to the start site (5' end) of each selected JNK activating phosphatase gene. When the antisense molecule then hybridizes to the corresponding JNK activating phosphatase mRNA, translation of this mRNA is prevented.

Alternatively, gene therapy may be employed to create a dominant-negative inhibitor of one or more JNK activating phosphatase polypeptides. In this situation, the DNA encoding a mutant full length or truncated polypeptide of each selected JNK activating phosphatase polypeptide can be prepared and introduced into the cells of a patient using either viral or non-viral methods as described above. Each such mutant is typically designed to compete with endogenous polypeptide in its biological role.

Uses of JNK Activating Phosphatase Nucleic Acids and Polypeptides

Nucleic acid molecules of the invention may be used to map the locations of the JNK activating phosphatase gene and related genes on chromosomes. Mapping may be done by techniques known in the art, such as PCR amplification and in situ hybridization.

The nucleic acid molecules are also used as anti-sense inhibitors of JNK activating phosphatase polypeptide expression. Such inhibition may be effected by nucleic acid molecules that are complementary to and hybridize to expression control sequences (triple helix formation) or to JNK activating phosphatase mRNA. Anti-sense probes may be designed by available techniques using the sequence of the JNK activating phosphatase genes disclosed herein. Anti-sense inhibitors provide information relating to the decrease or absence of an JNK activating phosphatase polypeptide in a cell or organism.

Hybridization probes may be prepared using an JNK activating phosphatase gene sequence as provided herein to screen cDNA, genomic or synthetic DNA libraries for related sequences. Regions of the DNA and/or amino acid sequence of JNK activating phosphatase polypeptide that exhibit significant identity to known sequences are readily determined using sequence alignment algorithms disclosed above and those regions may be used to design probes for screening.

The nucleic acid molecules of the invention may be used for gene therapy. Nucleic acid molecules that express JNK activating phosphatase polypeptide in vivo provide information relating to the effects of the polypeptide in cells or organisms.

JNK activating phosphatase nucleic acid molecules, fragments, variants, and/or derivatives that do not themselves encode biologically active polypeptides may be useful as hybridization probes in diagnostic assays to test, either qualitatively or quantitatively, for the presence of JNK activating phosphatase DNA or corresponding RNA in mammalian tissue or bodily fluid samples.

JNK activating phosphatase polypeptides, fragments, variants, and/or derivatives may be used to screen agents for preventing, treating or diagnosing JNK-mediated disorders.

JNK activating phosphatase polypeptides, fragments, variants, and/or derivatives, whether biologically active or not, are useful for preparing antibodies that bind to an JNK activating phosphatase polypeptide. The antibodies may be used for in vivo and in vitro diagnostic purposes, including, but not limited to, use in labeled form to detect the presence of JNK activating phosphatase polypeptide in a body fluid or cell sample. The antibodies may also be used to prevent or treat JNK-mediated disorders. The antibodies may bind to an JNK activating phosphatase polypeptide so as to diminish or block at least one activity characteristic of an JNK activating phosphatase polypeptide, or may bind to a polypeptide to increase an activity.

The following examples are intended for illustration purposes only, and should not be construed as limiting the scope of the invention in any way.

EXAMPLE 1

Cloning of Mouse JNK Activating Phosphatase Polypetptide Gene

Materials and methods for cDNA cloning and analysis are described in Sambrook et al. supra.

Original sequence tags identified as "LS20-1" and "LS20-2" came from a sequence survey of several hundred differential display PCR (DD-PCR) clones. The DD-PCR inserts were subcloned into the plasmid vector pGEM-T (Promega). The common insert in tag LS20-1 and LS20-2 exhibited no sequence homologies with other known genes, expressed sequence tags (ESTs), or sequence-tagged sites (STSs) in a contemporaneous search of GenBank. The insert in LS20-1 was in a sense orientation with respect to the T7 polymerase transcription initiation site in the pGEM vector. The insert in LS20-2 was in an antisense orientation with respect to this same promoter (orientation was deduced by labelling probes in both orientations and hybridizing to Northern blots). The clone LS20-2, when digested with the restriction endonuclease PstI yields a good template for the synthesis of a radio-labelled riboprobe using the T7 transcription initiation site. Such a riboprobe template was used for subsequent screening of lambda phage libraries for full length LS20 cDNA.

Northern analysis of LS 20 expression in the mouse demonstrated good levels of mRNA in the skeletal muscle, among other tissues. Skeletal muscle was chosen as the target source because we had several "good" mouse and human skeletal muscle cDNA libraries (Clontech and Stratagene) in hand.

A mouse skeletal muscle cDNA library (Clontech) was titered. One million placques were plated and lifted in duplicate onto nitrocellulose filters (Schleicher and Schuell, Keens, N.H.). Hybridization with the LS20 riboprobe was performed in Stark's buffer (50% formamide; 50 mM potassium phosphate, pH 6.5; 5×SSC; 1% SDS; 5× Denhardt's; 0.05% sodium sarcosyl; and 300 µg/mL salmon sperm DNA) at 42° C., overnight (ON). Filters were washed to a final stringency of 1×SSC, 0.1% SDS, 42° C., and exposed to X-ray film (X-OMAT AR, Eastman Kodak, Rochester, N.Y.) ON at −70° C. with intensifying screens. Films were developed and 13 plaque pools (from plates 2, 7, 8, 9, 10 (2ea.), 15, 16, 17, 18 (2ea.), 19, and 20) hybridizing on both pairs of duplicate lifts were identified and isolated.

To facilitate rapid isolation of novel sequence extending the known LS20 sequence, anchored PCR was used on these 13 primary plaque pools. Three synthetic oligonucleotides were prepared. The first oligonucleotide, 1065-30 (SEQ ID NO: 21), being identical in sequence to a 32 nucleotide region of the left lambda phage vector arm and flanking on one side the insert cloning site within the vector:

```
                                      (SEQ ID NO:21)
(5'-ccttttgagcaagttcagcctggttaagtcc-3').
```

The second oligonucleotide, 1386-58 (SEQ ID NO: 22), being identical in sequence to a 33 nucleotide string near the 5'-end of the LS20-2 insert:

```
                                      (SEQ ID NO:22)
(5'-ggaggcctctctctgtgtgtgtggagccctcagg-3');
```

The third oligonucleotide, 1386-59 (SEQ ID NO: 23), being complementary (anti-sense) to a 31 nucleotide strings near the 3'-end of the LS20-2 insert:

```
                                      (SEQ ID NO:23)
(5'-ggcagcaccagcctgaactttgcaaatttc-3').
```

The lambda phage-specific primer was combined with either of the two LS20-specific primers and the PCR was performed. Four of the original plaque pools allowed PCR amplification with one, but not the other, of the LS20-specific primers (pools 7, 17, 18, and 20). The PCR products thus amplified were gel purified and named #s 3, 18, 19, and 26, respectively (number designation corresponding to gel lane). Gel purified fragments were subcloned into the plasmid vector pCR2.1 (InVitrogen, Inc., San Diego, Calif.) and individual clones isolated (clones 3-2, 19-27, and 26-31).

Inserts from these three plasmid clones were sequenced on both strands and compared to the original LS20 sequence. The longest 5-extension of the original LS20 sequence was contained in the clone 26-31, but did not extend into LS20 coding region. A 1.1 Kbp probe template was prepared by digesting the clone 26-31 with the restriction enzyme NcoI. This probe template was used to synthesize random hexamer-primed probes for further screening of a Stratagene mouse skeletal muscle library.

A second mouse skeletal muscle library (Stratagene) was plated and lifted as before, and probed with a random hexamer-primed probe prepared from the 1.1 Kbp LS20 template described above. The filters were hybridized as for the first library, then washed to a final stringency of 2×SSC, 0.1% SDS, 42C, 5 m. Upon exposure of films, 20 primary positive pools were isolated (pools 2-1, 2-2, 2-3, 3-1, 6-1, 6-2, 6-3, 7-1, 12-1, 12-2, 12-3, 16-1, 16-2, 16-3, 16-4, 16-5, 16-6, 18-1, 18-2, 18-3). Anchored PCR was performed as described above, using the same primers. Primary plaque pools 2-3, 16-2, 16-4, and 18-4 all yielded PCR products with the LS20-specific primer 1386-58, but not 1386-59. All pools except 2-3 allowed amplification of multiple bands, therefore the single amplified band from pool 2-3 was gel purified, subcloned (pCR2.1), and sequenced. The sequence of subclone 2-3b (via PCR amplification of primary pool 2-3) was obtained by us and shown to contain an open reading frame encoding a putative protein with homology to a class of proteins known as dual-specificity phosphatases. Subsequent cloning of the human orthologue of this cDNA (described below) demonstrated that the mouse LS20 cDNA was full length and did encode the bona fide initiation methionine for the protein known here as JKAP or JNK activating phosphatase.

EXAMPLE 2

Cloning of Human JNK Activating Phosphatase Polypeptide Gene

A FASTA search of Genbank EST sequences with the novel mouse LS20 cDNA sequence revealed a high homology hit with a human EST designated clone 249002. The clone 249002 was purchased from an IMAGE consortium supplier (Genome Systems, St. Louis, Mo.) and sequenced in its entirety. The insert was short, 614 bp. The insert of clone 249002 was isolated by digestion with the restriction enzymes EcoRI and NotI, gel-purified and used as a template for the synthesis of random hexamer-primed probes used in subsequent screens of a human fetal liver cDNA library (Clontech). In addition, two new oligonucleotide primers were synthesized based on the human LS20 sequence. Sense (1470-25) (SEQ ID NO: 24) and anti-sense (1470-26) (SEQ ID NO: 25) primers were designed to allow amplification of a 143bp internal fragment of the human LS20 sequence or for use in an anchored PCR scheme similar to that used in the cloning of the mouse LS20 cDNA described above.

```
(5'-c agcagcgg attcaccatc-3')    (SEQ ID NO: 24)

(5'-gcgatcaccagtgtcacgc-3')      (SEQ ID NO: 25)
```

A human fetal liver cDNA library was plated and lifted in duplicate, as described above. A random hexamer-primed probe from the ca.600bp 249002 template was hybridized with these filters at 42C, O/N. The filters were washed to a final stringency of 0.2×SSC, 0.1% SDS, 42C and exposed to film. Eight primary positive pools were identified and isolated (pools 5-1, 5-2, 10-1, 16-1, 16-2, 16-3, 16-4, 16-5). Anchored PCR was performed on these pools, using the vector-specific primer 1065-30 and one of the two hLS20-specific primers 1470-25 or -26. A PCR product from one of these primary pools (16-1A) was gel purified, subcloned and sequenced.

A sequence from 16-1A-derived subclones was obtained. The sequence encoded a full length human LS20 cDNA, complete with upstream stop codon in-frame with the predicted initiation methionine, the full orf, and termination codon. DNA sequencing was performed on both strands of each template using the Taq Dye Terminator Cycle Sequencing kit (Applied Biosystems, Foster City, Calif.) and primers appropriate to the cloning vector on an automated DNA sequencer (Model 377, Applied Biosystems), as per the manufacturer's recommendations.

EXAMPLE 3

The JKAP Amino Acid Sequence Analysis and Expression Pattern

JKAP was initially identified in a screen designed to isolate transcripts differentially upregulated in adult mouse bone marrow hematopoietic cells, FACS-sorted Lin⁻ Sca-1⁺ subset of whole mouse bone marrow cells derived from C57816 strain mice. Differential-display PCR (DDPCR) (DDPCR was performed as described [R. Jurecic, T. Nguyen, J. W. Belmont, *Trends Genet.* 12, 502 (1996); R. Jurecic, R. G. Nachtman, S. M. Colicos, J. W. Belmont, *Anal. Biochem.* 259, 235 (1998)]) was employed to identify the JKAP transcript, among others, as being expressed preferentially in the stem-cell-enriched Lin⁻ Sca-1⁺ population of mouse bone marrow cells obtained by FACS, compared to the Lin⁻ Sca-1⁻ population which is deficient in stem-cell activity. JKAP mapped to mouse proximal Chromosome 13 by backcross panels (add marker order). The full-length JKAP cDNA consisted of 3012 bp (cDNA cloning—A full-length cDNA clone of JKAP was isolated from a skeletal muscle library, based on preliminary expression data), and contained a 700 bp open reading frame with high similarity to a subgroup of protein tyrosine phosphatases, the dual-specificity phosphatases, that have activity in the MAPK pathways (FIG. 3A). The predicted JKAP protein contains the catalytic C-terminal domain of dual-specificity phosphatases, but lacks an N-terminal non-catalytic domain, and is consequently ~100 aa shorter than most other MAPK phosphatases. All residues of the signature motif I/VH-CxxGxSRS of dual-specificity phosphatases (J. M. Denu, J. A. Stuckey, M. A. Saper, J. E. Dixon, *Cell* 87, 361 (1996); N. K. Tonks and B. G. Neel, ibid, p. 365) are conserved in the JKAP phosphatase. Maximum parsimony analysis restricted to the catalytic domain indicates that JKAP is not an orthologue of previously described MAPK phosphatases (FIG. 3B). By Northern blot analysis, JKAP is expressed in most adult mouse tissues examined (FIG. 3C). The detection of two transcripts, the predominant of which corresponds with the full-length JKAP cDNA, suggests tissue-specific splicing or processing. Either or both the 3.0 kb transcript and the 1.3 kb transcript were present in brain, testis, heart, liver, and kidney, and at lower levels in skeletal muscle.

EXAMPLE 4

In Situ Hybridization of Mouse Bone Marrow Cells

To further characterize the expression pattern of JKAP in mouse tissues, an in situ hybridization analysis was conducted. Hybridization of Lin Sca-1⁺ and Lin Sca-1⁻ cells from adult mouse bone marrow confirmed differential expression of JKAP (FIGS. 4, A and B), suggesting a role for JKAP unique to cells within this hematopoietic precursor population. Lin Sca-1⁺ and Lin Sca-1⁻ cells obtained through FACS from mouse bone marrow were resuspended and fixed in 4% paraformaldehyde in PBS, then deposited on RNase-free, TESPA (Sigma)-treated glass slides. In situ hybridization was conducted as described [U. Albrecht, G. Eichele, J. A. Helms, H. C. Lu, in *Molecular and Cellular Methods in Developmental Toxicology*, G. P. Daston, Ed. (CRC Press, Boca Raton, 1997), pp. 23–48], with modifications made for cells. 0.5–1 µg/mL digoxigenin-labelled JKAP riboprobe, corresponding to nucleotide positions 2251 to 2566 of the JKAP cDNA, was hybridized to the cells without coverslipping as described [W. Nürnberg, B. M. Czarnetzki, D. Schadendorf, *Biotechniques* 18, 406 (1995)].

Lin⁻ Sca-1⁺ and Lin⁻ Sca-1⁻ mouse cells obtained through flow cytometry were resuspended and fixed in 4% paraformaldehyde in PBS, then deposited on RNase-free, TESPA (Sigma)-treated glass slides. The cells were air-dried at room temperature for 20–30 min, rinsed in PBS for 5 min, acetylated in 0.1 M triethanolamine-HCl (Fisher) pH 8.0 with 0.72% acetic anhydride (Fisher) for 10 min, and rinsed in PBS for 5 min. The cells were then equilibrated in 0.9% NaCl for 5 min, carried through a dehydration series of 30%, 50%, 70%, 80%, 95%, and 100% EtOH, and finally air-dried for 20 min at room temperature. The cells were encircled using a hydrophobic pen (Electronic Microscopy Sciences) and incubated with 50 µL of prehybridization solution (50% formamide, 20 mM tris-HCl pH 8.0, 0.3 mM NaCl, 10% dextran sulfate, 1× Denhardt's, 0.5 mg/mL yeast tRNA, 10 mM DTM) at 50–55 C for 1 hr in a humid chamber. Digoxigenin-labelled riboprobe in 50 µL hybridization solution, heated at 95 C for 5 min, was added to a final concentration of 50–100 ng per 100 µL total hybridization volume, and incubated at 50–55 C for 14–18 hrs. Post-hybridization, the slides were washed with constant agitation in 2×SSC, 0.1% Tween-20 at 55–60° C. for 1 hr, 0.5×SSC, 0.1% Tween-20 at 37° C. for 30 min, and 0.5× SSC, 0.1% Tween-20 at room temperature for 30 min. For antibody detection of the DIG-labelled riboprobe, the cells were rinsed in PBS, incubated in blocking buffer (10% lamb serum in PBS 0.1% Tween-20) at 37° C. for 30 min, then incubated with sheep anti-DIG-AP-conjugated antibody (Boehringer Mannheim) diluted 1:500 in blocking buffer at 37° for 1 hr. Following antibody incubation, the slides were rinsed in PBS, 0.1% Tween-20, washed in PBS, 0.1% Tween-20 at room temperature for 10 min with constant agitation, then washed in detection buffer (100 mM tris-HCl pH 9.5, 100 mM NaCl, 50 mM MgCl₂) at room temperature for 10 min with constant agitation. For calorimetric detection of the antibody, the slides were incubated in substrate solution (450 µg/mL nitro blue tetrazolium chloride(NBT), 175 µ/mL 5-bromo-4-chloro-3-indolyl-phosphate, 4-toluidine salt (BCIP, 240 µg/mL levarnisole in detection buffer) at room temperature for 30–60 min in a dark, humid chamber. Finally, the reaction was terminated by rinsing the slides thoroughly in water, and coverslips were mounted using an aqueous mounting medium.

EXAMPLE 5

In Situ Hybridization of E10.5 Mouse Embryos

Whole-mount in situ hybridization of embryonic day (E) 10.5 mouse embryos detected highest levels of JKAP transcripts in the somites and branchial arches (FIGS. 4, C through E). Whole mount in situ hybridization to E10.5 mouse embryos was performed as described [D. G. Wilkinson, in *In situ Hybridization: A Practical Approach*, D. G. Wilkinson, Ed. (IRL Press, Oxford, 1992), pp. 75–83], with the exception that hybridization was carried out in stationary tubes, using 200 ng/mL of digoxigenin-labelled riboprobes corresponding to nucleotide positions 17 to 1522 of the JKAP cDNA. On day 1, embryos (fixed overnight in 4% paraformaldehyde in PBT (PBS+0.1% Tween-20) washed three times in PBT and stored in 100% methanol until the day of hybridization) were rehydrated through a 75%–50%–25%–0% methanol series, washed twice in PBT, and incubated for 15 minutes in a solution of 10 µg/ml proteinase K in PBT. The proteinase K reaction was stopped by washing in 2 mg/ml glycine in PBT, followed by refixation in 4% paraformaldehyde/0.2% glutaraldehyde in PBT. Embryos were washed three times in PBT, prehybridized for one hour at 65° C. in hybridization solution (5×SSC, 50% formamide, 1% SDS, and 100 µg/ml each of heparin and yeast tRNA), and hybridized overnight in fresh hybridization solution to which 100 ng/ml digoxygenin-labelled riboprobe had been added. On day two, the following washes were performed: (1) twice for 30 minutes in Wash Solution I (5×SSC, 50% formamide, 1% SDS) at 65° C.; (2) once for 10 minutes in 1:1 Wash Solution I:Wash Solution II (0.5M NaCl, 10 mM Tris-HCl pH 7.5, 0.1% Tween-20) at 65° C.; (3) three times for 5 minutes in Wash Solution II at room temperature; (4) once for 30 minutes in Wash Solution II+100 µg/ml RNase A at 37° C.; (5) once for 5 minutes in Wash Solution II; (6) twice for 30 minutes in Wash Solution III (2×SSC, 50% formamide, 0.1% Tween-20) at 65° C.; (6) three times for 5 minutes in TBST (140 mM NaCl, 2.7 mM KCl, 25 mM Tris-HCl pH 7.5, 0.1% Tween-20); (7) once for 90 minutes in TBST+10% normal lamb serum; (8) overnight in TBST+1:2000 dilution of sheep and digoxygenin Fab fragments in 4° C. (Fab fragments preabsorbed for 60 minutes to heat-inactivated E14.5 mouse embryo powder in TBST+1% normal lamb serum). On day three, the embryos were washed five times for 60 minutes in TBST at room temperature, followed by a sixth wash overnight at 4° C. On day four, the embryos were washed twice for 10 minutes in CT solution (100 mM Tris-HCl pH 9.5, 150 mM NaCl, 25 mM MgCl$_2$, 2 mM levamisole, 0.1% Tween-20), and then incubated in the dark at room temperature in CT solution+ 337.5 µg/ml nitroblue tetrazolium salt+175 µg/ml 5-bromo4chloro-3-indolyl-phosphate+10% polyvinyl alcohol (Barth and Ivarie, 1994). After approximately five to six hours of color development, embryos were washed three times in PBT, cleared in 50% glycerol in PBT, followed by storage at 4° C. in 50% glycerol in PBT. Embryos were embedded in paraffin and sectioned according to Albrecht et al. (199^). Sections were counterstained with nuclear fast red.

Color development was enhanced by the addition of polyvinyl alcohol as described [J. Barth and R. Ivarie, *Biotechniques* 17, 324 (1994)]. No expression was observed in the embryonic dorsal aorta, a region identified as a site of definitive hematopoieses in chick and human embryos at similar developmental stages (T. Jaffredo, R. Gautier, A. Eichmann, F. Dieterlen-Lievre, *Development* 125, 4575 (1998); M. Labastie, F. Cortes, P. Romeo, C. Dulac, B. Peault, *Blood* 92, 3624 (1998)); indicating that the earliest intraembryonic hematopoietic cells do not express JKAP (FIG. 4F).

EXAMPLE 6

Transfection of 293T Cells

Given the close sequence similarity of JKAP to MAPK phosphatases, the activity of JKAP phosphatase in MAPK cascades was examined. We assayed MAPK activity in 293T cells co-transfected with the JKAP phosphatase and either JNK1, ERK2, or p38 using an immunocomplex kinase assay. Endogenous JNK1 and over-expressed HA-JNK1 were immunoprecipitated by incubation with rabbit anti-JNK1 polyclonal antibody (Ab101) and mouse anti-HA monoclonal antibody (12CAS), respectively, plus protein A-agarose beads (Bio-Rad) in lysis buffer (20 mM HEPES, pH 7.4, 2 mM EGTA, 50 mM glycerophosphate, 1% Triton X-100, 10% glycerol, 1 mM dithiothreitol, 2 µg/mL aprotinin, 1 mM phenylmethylsulfonyl fluoride. 1 mM NaCl and 1 mM Na$_3$VO$_4$). The precipitates were washed twice with lysis buffer, twice with LiCl buffer (500 nM LiCl, 100 mM Tris-HCl, pH 7.6 and 0.1% Triton X-100), and twice with kinase buffer (500 mM LiCl, 100 mM Tris-HCl, pH 7.6, and 0.1% Triton X-100), and twice with kinase buffer (20 mM MOPS, pH 7.2, 2 mM EGTA, 10 mM MgCl$_2$, 1 mM dithiothreitol, 0.1% Triton X-100, and 1 mN Na$_3$VO$_4$). The pellets were then mixed with 1 µg of GST-clun (1-79), 15 µM ATP, and 10 µgCi of [y$^{-32}$P] ATP in 30 µL of kinase buffer. The kinase reaction was performed at 30 C for 30 min. and terminated with an equal volume of SDS sampling buffer. The reaction mixtures were analyzed by SDS-PAGE and autocadiography. Polyclonal Ab101 was derived from rabbits that were immunized with peptide

N'-CKNGVIRGQPSPLAQVQQ        (SEQ ID NO:27)

The carrier used was KLH. This antibody was prepared by standard methods using two injections and termination three weeks after burst injection. One suitable source for preparation of Ab101 (titer>1:10 K) is Genemed Synthesis, Inc See also Chen, Y.-R, Meyer, C. F., and Tan, T.-H., (1996). Persistent activation of c-Jun N-terminal kinase 1 (JNK1) in gamma radiation-induced apoptosis. J.Biol. Chem. 271: 631–634; Hu, M. C.-T., Qiu, W. R, Wang, X., Meyer, C. F, and Tan, T.-H., (1996). Human HPK1, a novel human hematopoietic projenitor kinase that activates the JNK/SAPK kinase cascade. Gene & Development 10:2251–2264.; Wang W., Zhou, G., Hu, M. C.-T., Yao, Z., and Tan, T.-H., (1999). Activation of Hematopoietic progenitor kinase 1 (HPK1)-dependent, stress-activated c-Jun N-terminal kinase (JNK) pathway by transforming growth factor beta (TGF-beta)-activated kinase (TAK1), a kinase mediator of TGF-beta signal transduction. J. Biol. Chem. 272:22771–22776; Ensenat, D., Yao Z., Wang X. S., Kori, R., Zhou, G., Lee, S. C, and Tan, T.-H., (1 999). A novel Src homology 3 domain-containing adaptor protein, HIP55, that interacts with hematopoietic progenitor kinase 1. J. Biol. Chem. 274:33945–33950; Zhou, G., Lee, S. C, Yao, Z., and Tan, T.-H., (1999). Hematopoietic progenitor kinase 1 is a component of transforming growth factor beta-induced c-Jun N-terminal kinase signaling. J. Biol. Chem. 274: 13133–13138.

Figures 5A, 5B:
FIG. 5 illustrates activation of JNK, but not p38 or ERK, by JKAP in transfected 293T cells. (A) 293T cells (1.5×10⁵ cells/35 mm well) were transfected with 0.1 µg of HA-JNK alone, HA-JNK plus 2 µg of either JKAP or JKAP-C88S. (B) 293T cells (1.5×10⁵ cells/35 mm well) were co-transfected with 2 µg of HA-p38 and various amounts of JKAP. As a control, co-transfection of HA-p38 and 2 µg of MKK6 was included. (C) 293T cells (1.5×10⁵ cells/35 mm well) were co-transfected with 2 µg of HA-ERK2 and various amounts of JKAP. As a control, co-transfection of HA-ERK 2 and 0.5 µg of PKC-ξ was included. Empty vectors were used to normalize the amount of transfected DNA. At 44 h post-transfection, cells were collected and cell lysates prepared. HA-JNK1, HA-p38, and HA-ERK2 were immunoprecipitated with an anti-HA antibody (12CA5), and immunocomplex kinase assays were performed using GST-cJun (1-79), GST-ATF2, and MBP as substrates, respectively. Equivalent levels of HA-JNK, HA-p38, and HA-ERK2 expression were verified by immunoblot analysis using anti-HA (12CA5). (D) Blocking of TNF-alpha induced JNK activity by mutant JKAP. 293T cells transfected with 0.1 ug of HA-JNK1 alone or HA-JNK1 plus 2 ug of JECAP88S were treated with TNF-alpha (10 ng/ml). After 30 minutes, cells were collected and cell lysates prepared. HA-JNK1 was immunoprecipitated with an anti-HA antibody (12CA5), and immunocomplex kinase assays were performed using GST-cJun (1-79) as a substrate. Equivalent levels of HA-JNK1 expression were verified by immunoblot (IB) analysis using anti-HA (12CA5).
Figure 7A:
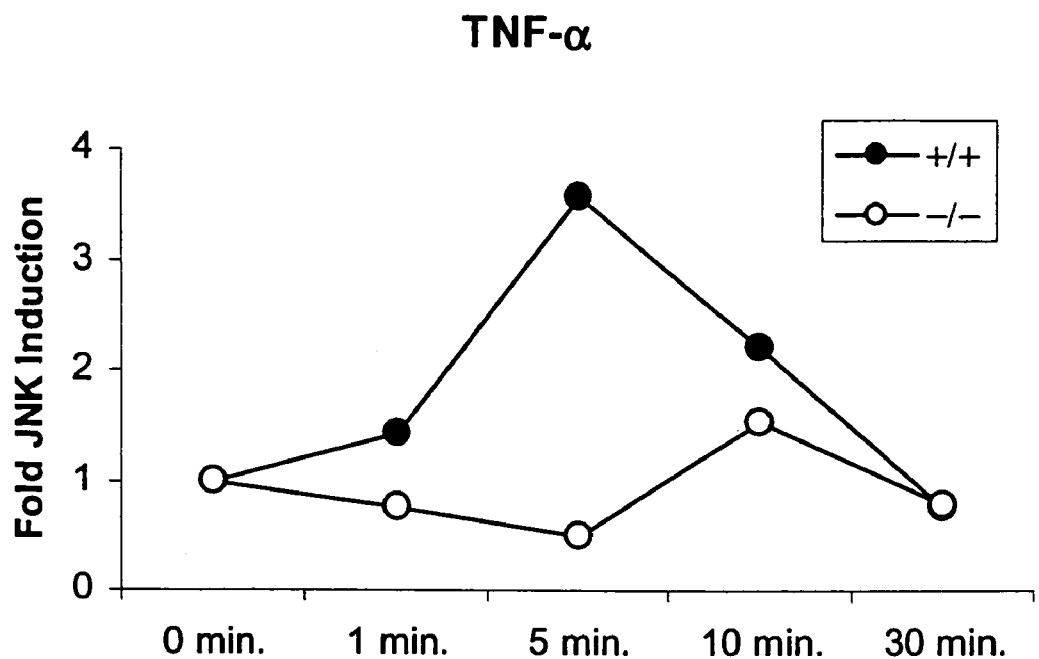
FIG. 7 illustrates the reduced response of JKAP⁻/⁻ ES cells to respond to (A) TNF-α, (B) TFG-β, (C) Il-1 and (D) sorbitol, but not (E) UV-C, for JNK activation. ~80% confluence of JKAP⁺/⁺ and JKAP⁻/⁻ ES cells were treated with TNF-α (10 ng/mL), TGF-β (10 ng/mL), and IL-1 (10 ng/mL) for 10 min and sorbitol (400 mM), and UV-C (300 J/m²) for 30 min at 37° C. Cells were then collected and cell lysates prepared. Endogenous JNK1 was immunoprecipitated with an anti-JNK1 Antibody (Ab101), and immunocomplex kinase assays were performed using GST-cJun (1-79) as a substrate. (F) The expression levels of JNK1 JKAP⁺/⁺, JKAP⁺/⁻, and JKAP⁻/⁻ ES cells were monitored by immunoblot analysis using anti-JNK1 antibody (Ab101). (G) Cultures of fibroblasts derived from JKAP +/+and JKAP -/- embryos were stimulated with 100 ng/ml 4alpha-phorbol 12-myristate 13-acetate (PMA). After various times cell lysates were prepared and immunoprecipitated with anti-ERK2. ERK2 kinase activity was measured by phosphorylation of MBP. MBP was separated on PAGE gel and the phosphorylated product measured by phsphorimager analysis. (H) Cultures of fibroblasts derived from JKAP +/+ and JKAP -/- embryos were stimulated with UV-C (100J/m2) and at various times thereafter, immunocomplex assays for p38 activity were performed. Endogenous p38 was immunoprecipitated and then its kinase activity was measured on either MBP or GST-ATF2 with similar results.
Figure 7B:
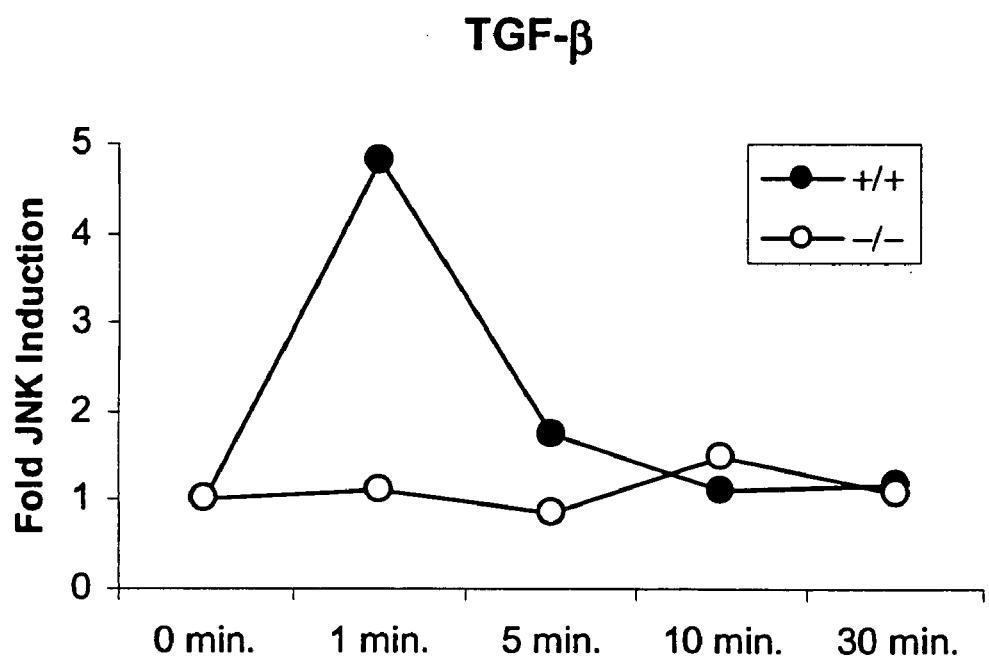
Figure 7C:
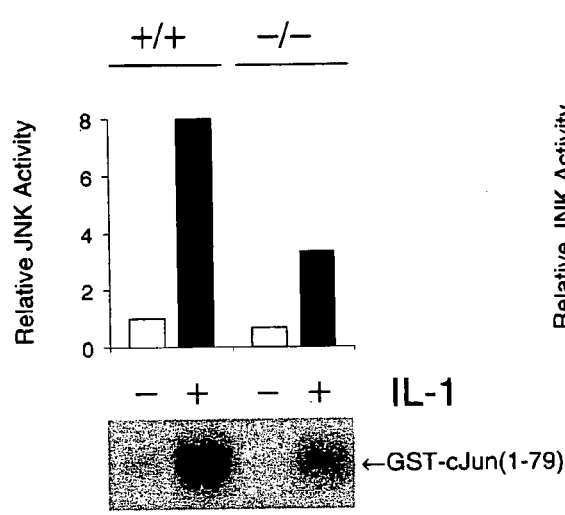
Figure 7D:
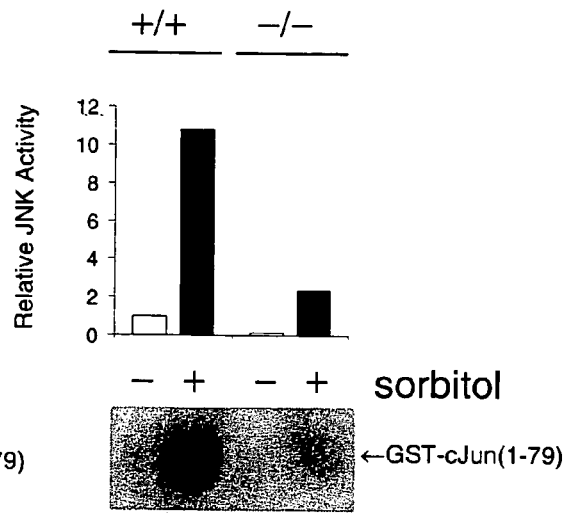
Figure 7E:
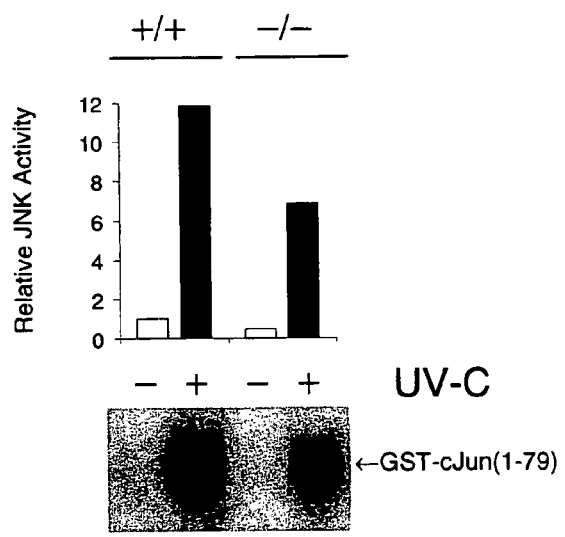
Figure 7F:
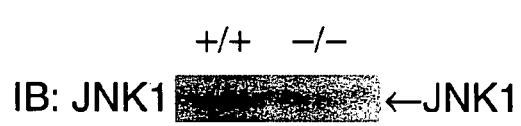
Figure 7G:
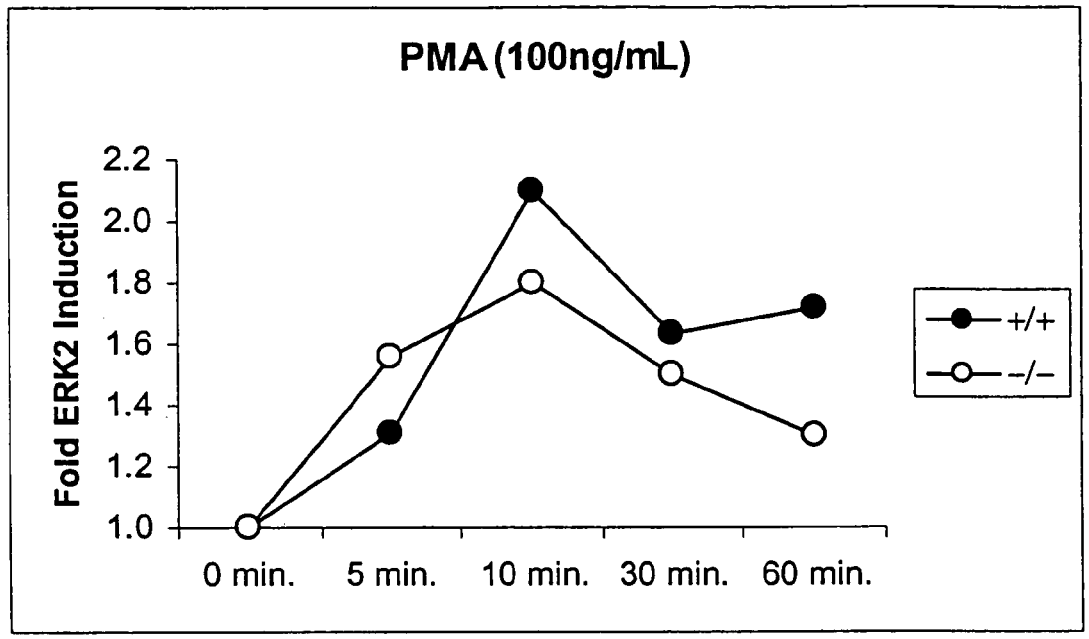
Figure 7H:
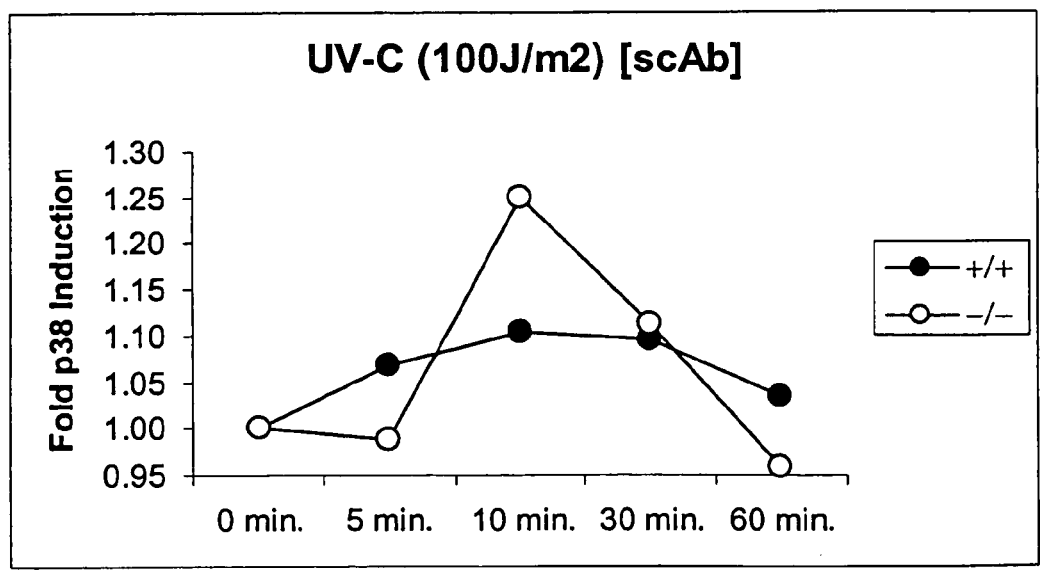

Unexpectedly, JKAP activated JNK1 but did not activate ERK2 or p38 (FIG. 5). Transient transfections were performed in 293T cells by using the calcium phosphate precipitation protocol provided by Specialty Media, Inc., Lavallette, N.J. Briefly, 293T cells were plated at a density of 1.5×10$^5$ cells/35 mm plate well and transfected with the indicated amounts of various DNA plasmids the next day. Empty vectors were used to normalize the amount of transfected DNA. The plasmid encoding β-galactosidase was cotransfected into the cells as an internal control to monitor the transfection efficiency.

Transfection with a mutant, inactive form of JKAP (JKAP-C88S) did not result in JNK activation, demonstrating that this response was dependent on intact. JKAP phosphatase activity. These. data suggest a specific role for JKAP in the JNK pathway. The mutant JKAP-C88S differs from wild-type JKAP in a single amino acid substitution of serine for cysteine at position 88. No other regions of the molecule are altered. The cysteine at position 88 is the central catalytically active reside in the nucleophilic attack of the phosphatase on the substrate. Thus, substitution of a serine at this position renders the JKAP molecule biochemically inactive.

TNF-alpha induced JNK activity was blocked by mutant JKAP. 293T cells transfected with 0.1 ug of HA-JNK1 alone or HA-JNK1 plus 2 ug of JKAP-C88S were treated with TNF-alpha (10 ng/ml). After 30 minutes, cells were collected and cell lysates prepared. HA-JNK1 was immunoprecipitated with an anti-HA antibody (12CA5), and immunocomplex kinase assays were performed using GST-cJun (1-79) as a substrate. Equivalent levels of HA-JNK1 expression were verified by immunoblot (IB) analysis using anti-HA (12CA5).

EXAMPLE 7

Effect of JKAP on Regulating JNK Activation

To determine whether JKAP is necessary for JNK activation, the response of cells deficient in the JKAP phosphatase to various stimuli was tested. Mouse embryonic stem (ES) cells heterozygous for the deletion of JKAP through homologous recombination were generated, and homozygous clones were derived by secondary selection (FIG. 6). JKAP$^{+/+}$ and JKAP$^{-/-}$ cells were exposed to one of several cytokines or environmental stresses (FIG. 7). JNK targeted ES cell clones were generated essentially as described [A. Bradley, pers. comm., and in *Teratocarinomas and Embryonic Stem Cells: A Practical Approach*, E. J. Robertson, Ed. (IRL Press. Oxford, 1987, pp. 113–152.] Briefly, a targeting vector was designed that deletes the two coding exons of JKAP which encode the catalytic domain of the phosphatase. The vector was constructed using DNA from a mouse 129/SV/EV total genomic DNA library. This vector was electroporated into an AB2.2 ES cell library from 129/SV/EV mice library. The AB2.2 ES cell lines were derived from Black Agouti 129 mice. This cell line is an XU cell line that when grown on SNL76/7 feeder cells are predominantly normal. SNL76/7, a clonal isolate of STO cells that have been transfected with a L1F expression cassette and RV4.0 (a neo expression cassette, have been selected for their ability to maintain ES cells in a "normal state". Resulting clones were screened by Southern blot analysis for evidence of homologous recombination. Two targeted clones were microinjected into E3.5 C57BL61 blastocysts, at approximately 20 ES cells per blastocyst ~80% confluent JKAP$^{-/-}$ and JKAP$^+$ ES cells in 60 mm dishes were treated with TNF-α (10 ng/mL), TGF-β (10 ng/mL), and IL-1 (10 ng/mL) for 10 min., and sorbitol (400 nM), and UV-C (300 J/m$^2$) for 30 min. Cells were then collected and cell lysates prepared. Endogenous JNK1 was immunoprecipitated with an anti-JNK1 (Ab101), and immunocomplex kinase assays were performed using GST-cJun (1-79) as a substrate. The expression levels of JNK1 in JKAP$^{-/-}$, JKAP$^+$ ES cells were monitored by immunoblot analysis using anti-JNK1 antibody (Ab101).Stimulation by the proinflammatory cytokines tumor necrosis factor (TNF)-α and transforming growth factor (TGF)-β which specifically engage the JNK pathway (A. J. Flint, T. Tiganis, D. Barford, N. K. Tonks, *Proc. Natl. Acad. Sci.* 94 1680 (1997); A. J. Garton, A. J. Flint, N. K. Tonks, *Mol. Cell Biol.* 16 6408 (1996)), resulted in greatly reduced JNK activation in JKAP$^{-/-}$ cells. Stimulation by interleukin (IL)-1 or hyperosmolar shock also reduced JNK activation, while stimulation by UV radiation resulted in only a mild reduction of JNK activation in JKAP$^{-/-}$ cells. These data demonstrate the requirement of JKAP for full induction of JNK activity under stimulus induction.

Cultures of fibroblasts derived from JKAP+/+ and JKAP-/- embryos were stimulated with 100 ng/ml 4-alpha-phorbol 12-myristate 13-acetate (PMA). After various times cell lysates were prepared and immunoprecipitated with anti-ERK2. ERK2 kinase activity was measured by phosphorylation of MBP. MBP was separated on PAGE gel and the phosphorylated product measured by phsphorimager analysis. See FIG. 7(g). Cultures of fibroblasts derived from JKAP+/+ and JKAP-/- embryos were stimulated with UV-C (100 J/m2) and at various times thereafter, immunocomplex assays for p38 activity were performed. Endogenous p38 was immunoprecipitated and then its kinase activity was measured on either MBP or GST-ATF2 with similar results. See FIG. 7(h). Compared to wild-type cells, JKAP-/- embryonic fibroblasts respond to PMA with activiation of the ERK2 pathway and respond to UV-C stimulation with activiation of the p38 stress response pathway. These results indicate that the main activity of JKAP in these cells is the JNK pathway. Pathway specificity may be an advantage for a compound that specifically enhance or interfere with JKAP activity and is not a prerequisite for JKAP utility.

EXAMPLE 8

Production of JNK Activating Phosphatase Polypeptide in Mammalian Cells

To express human JNK activating phosphatase in vitro, cDNA encoding human LS20 was subcloned into retroviral construct MSCV2.1 (Clontech). After verifying the sequence of LS20 insert, this expression vector was transfected into GP+E86 packaging cell line (Genetix Pharmaceuticals, Cambridge, Mass.) and supernatant containing recombinant virus was produced. This supernatant was then used to infect mouse NIH-3T3 cells (American Type Culture Collection) and infected clones were selected with G418 (Gibco BRL). Extracts from either control cells or cells infected with recombinant retrovirus containing LS20 cDNA were generated using lysis buffer (PBS+0.5% Nonidet P20 (Sigma, St. Louis, Mo.)). 30 μL of extracts were run on a 10% Tris-glycine gel (Novex, San Diego, Calif.). Proteins were then transferred to nitrocellulose paper (Schleicher and Schuell) and were blocked in TBS buffer (20 mM Tris, pH 7.5, 138 mM NaCl, 0.1% Tween 20 (Boehringer Mannheim)) with 5% dry milk. Anti-LS20 antiserum from animal #1436 was used in western blot analysis to detect LS20 at a ratio of 1:1000 in TBS buffer. Anti-rabbit Ig antibody #NA 934 (Amersham Pharmacia Biotech, Rahway, N.J.) conjugated with horse radish peroxidase was used for the secondary detection at a ratio of 1:2000. Detection of LS20 positive bands were performed with Enhanced Chemiluminacence (ECL) kit (Amersham, Piscataway, N.J.) using manufacturer's recommended protocol. Two bands, one 26 kiloDalton (kD) and the other 20 kD, were detected in the extract from cells infected with LS20 recombinant retrovirus but not in the control extract. The nature of the cause of double bands is not known.

EXAMPLE 9

Production of Anti-JNK Activating Phosphatase Polypeptide Antibodies

Antibodies to JNK activating phosphatase polypeptides may be obtained by immunization with purified protein or with JNK activating phosphatase peptides produced by biological or chemical synthesis. Procedures for generating antibodies can be those described in Leslie Hudson and Frank C. Bay, *Practical Immunology* (2$^{nd}$ Ed., Blackwell Scientific Publications 1980).

Animals (typically mice or rabbits) are injected with an JNK activating phosphatase antigen and those with sufficient serum titer levels as determined by enzyme-linked immunosorbent assays (EIA) are selected for hybridoma production. Spleens of immunized animals are collected and prepared as single cell suspensions from which splenocytes are recovered. The splenocytes are fused to mouse myeloma cells (such as Sp2/0-Ag14 cells), allowed to incubate in Dulbeccos' Modified Eagle' Medium (DMEM) with 200 U/ml penicillin, 200 ug/ml streptomycin sulfate, and 4 mM glutamine, then incubated in HAT selection medium (hypoxanthine, aminopterin, and thymidine). After selection, tissue culture supernatants are taken from each fusion well and tested for JNK activating phosphatase antibody production by EIA.

Alternative procedures for obtaining anti-JNK activating phosphatase antibodies may also be employed, such as immunization of transgenic mice harboring human Ig loci for production of fully human antibodies, and screening of synthetic antibody libraries, such as those generated by mutagenesis of an antibody variable domain.

In this experiment, a peptide containing sequence of 5' end of human JNK activating phosphatase (SEQ ID NO: 26) was generated and used for antibody induction. This peptide was coupled with carrier protein keyhole limpet hemacyanin and injected into rabbits at a boost schedule of once every two weeks. Titer of antibody against the peptide was determined using ELISA assays with plates immobilized with the peptide. One of the animals (#1436) was determined to have the highest titer against the peptide.

```
(H2N—CGNFKDARDAEQLS—COOH)    (SEQ ID NO: 26)
```

EXAMPLE 10

Interaction of JKAP with HPK-1

Figure 8A:
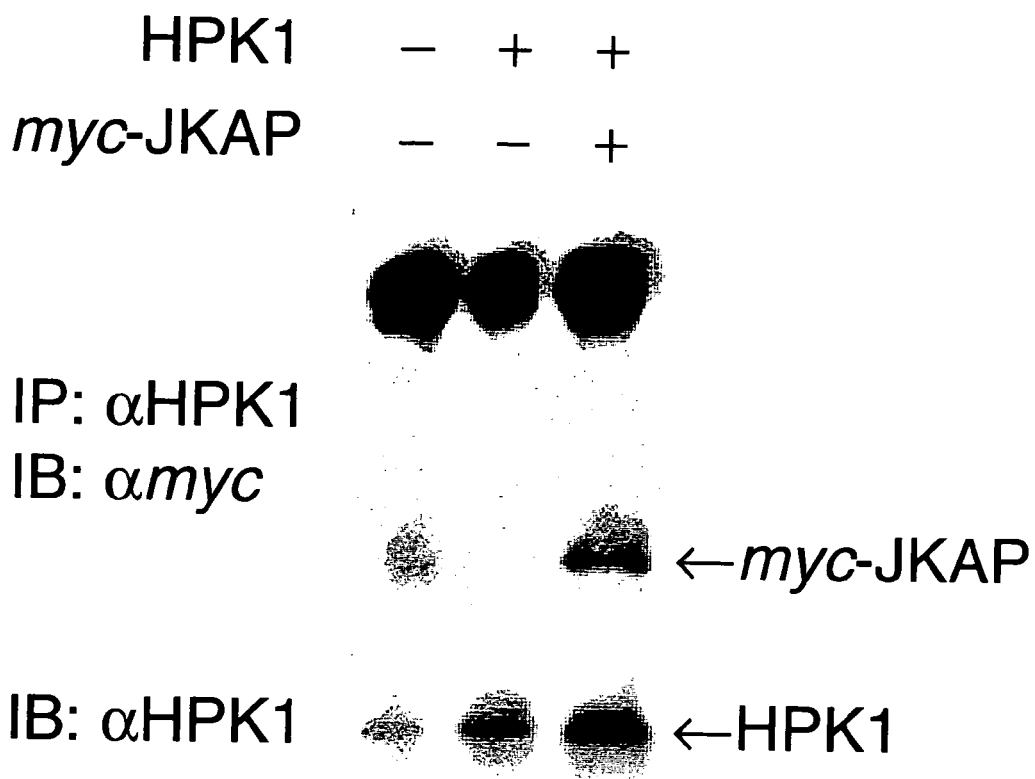
FIG. 8 illustates the co-expression of Myc-tagged JKAP with HPK-1 in 293T cells. (A) Lysates were prepared and HPK-1 was immunoprecipitated with an anti-HPK-1 antibody (484). Co-immunoprecipitated JKAP was detected with a commercially available anti-myc antibody. Equivalent levels of HPK-1 expression were confirmed by immunoblot analysis using a commercially available anti-HPK-1 antibody (484). (B) 293T cells were co-transfected with 0.1 ug of HA-JNK1 alone, HA-JNK1 plus 2 ug of either JKAP or HPK-1, or HA-JNK1 plus 2 ug each of both JKAP and HPK-1. See FIG. 8(b). Empty vectors were used to normalize the amount of transfected DNA. Cell lysates were prepared, and HA-JNK1 was immunoprecipitated with an anti-HA antibody (12CA5). Immunocomplex kinase assays were performed using GST-cJune (1-79) as a substrate (WESTERN). (C) 292T cells were transfected with 2 ug empty vector control, myc-JKAP, or myc-JKAP-C88S. Cell lysates were prepared and immunoprecipitated with a commercially available anti-myc antibody. The resulting precipitates were assayed for phosphatease activity by hydrolysis of p-ntitrophenyl phosphate (pNPP). The enzyme reaction was terminated after 30 minutes by addition of 3N NaOH and the product measured spectrophotometrically at 410 nm.
Figure 8B:
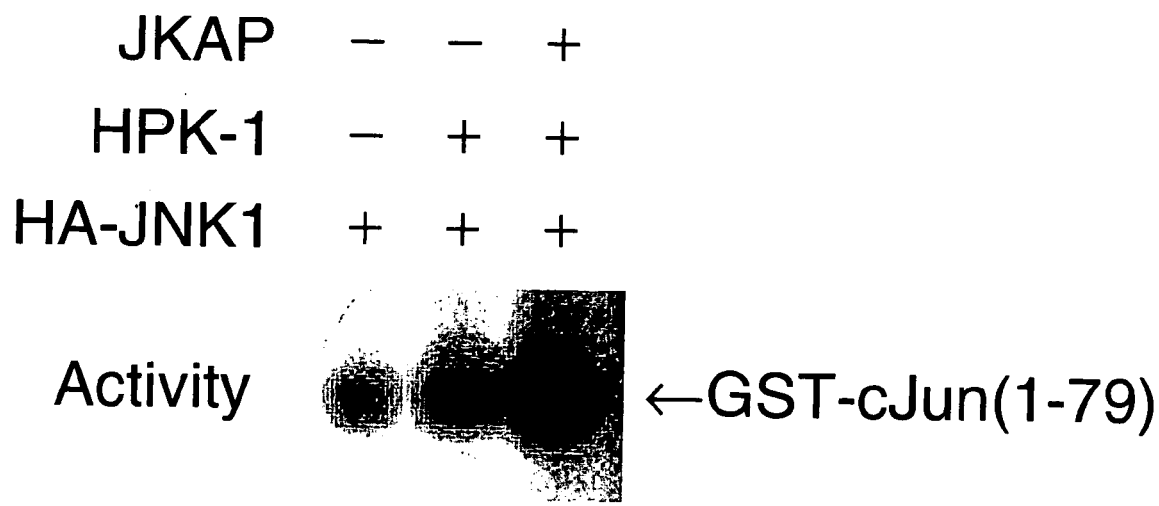
Figure 8C:
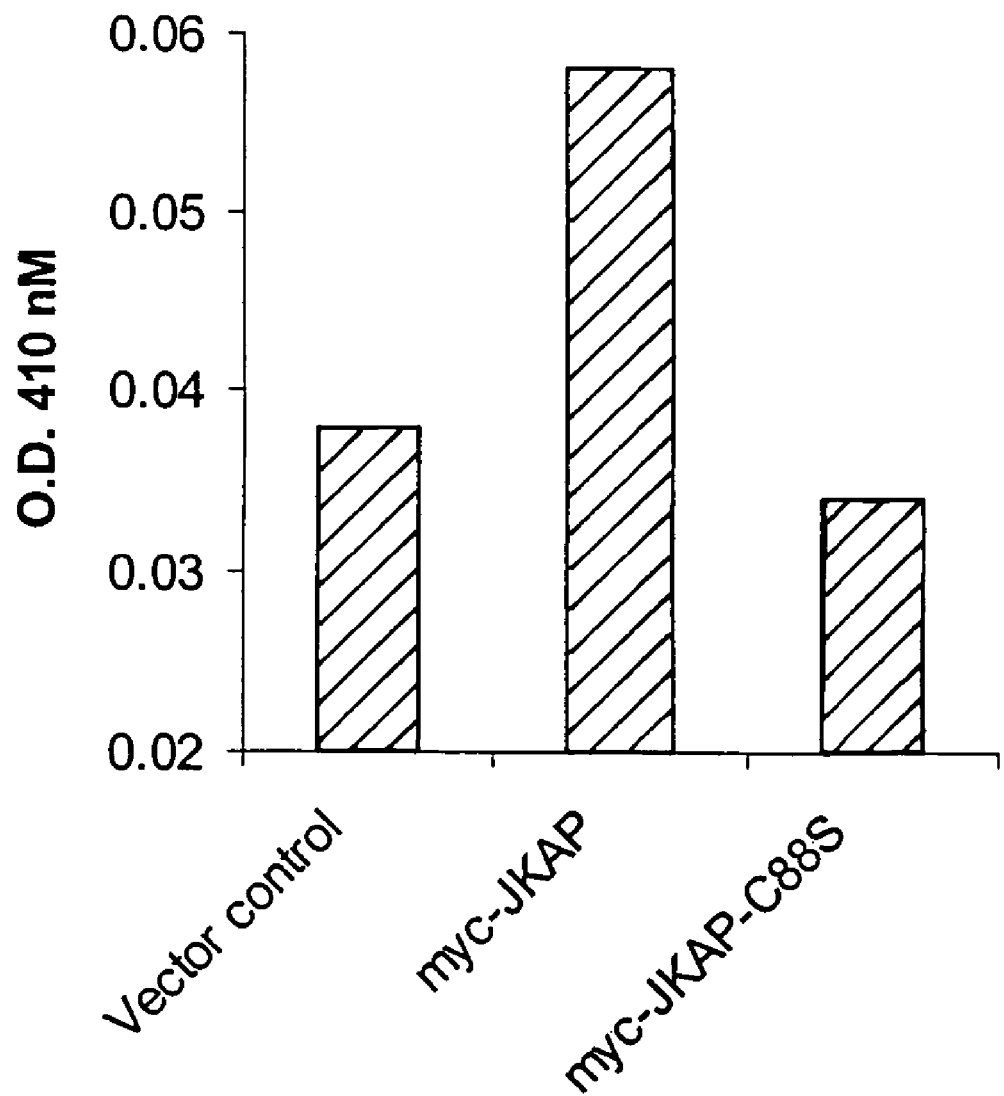

Myc-tagged JKAP was coexpressed with HPK-1 in 293T cells. See FIG. 8(a). Lysates were prepared and HPK-1 was immunoprecipitated with an commercially available anti-HPK-1 antibody (484). Co-immunoprecipitated JKAP was detected with a commercially available anti-myc antibody. Equivalent levels of HPK-1 expression were confirmed by immunoblot analysis using a commercially available anti-HPK-1 antibody (484). 293T cells were co-transfected with 0.1 ug of HA-JNK1 alone, HA-JNK1 plus 2 ug of either JKAP or HPK-1, or HA-JNK1 plus 2 ug each of both JKAP and HPK-1. See FIG. 8(b). Empty vectors were used to normalize the amount of transfected DNA. Cell lysates were prepared, and HA-JNK1 was immunoprecipitated with an anti-HA antibody (12CA5). Immunocomplex kinase assays were performed using GST-cJune (1-79) as a substrate (WESTERN). 292T cells were transfected with 2 ug empty vector control, myc-JKAP, or myc-JKAP-C88S. Cell lysates were prepared and immunoprecipitated with a commercially available anti-myc antibody. The resulting precipitates were assayed for phosphatase activity by hydrolysis of p-nitrophenyl phosphate (pNPP). The enzyme reaction was terminated after 30 minutes by addition of 3N NaOH and the product measured spectrophotometrically at 410 nm. See FIG. 8(c).

JKAP has been shown to have intrinsic phosphatase activity compared to relevant controls. The site-specific mutation of JKAP within an amino acid residue that is conserved in all known dual-specificity phophatases results in complete abrogation of the observed phosphatase activity. JKAP could be specifically found to interact with HPK-1 a serine-theonine kinase that acts upstream of JNK in the JNK pathway. In addition, JKAP specifically synergizes with HPK-1 in the activation of JNK. This result suggests that JKAP activates HPK-1. HPK-1 may be one of the natural substrates of JKAP although the precise residue that may be the target for dephosphorylation is not discovered by these experiments.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated polypeptide encoded by the nucleic acid molecule selected from the group consisting of:
   (a) the nucleotide sequence as set forth in SEQ ID NO: 1;
   (b) a nucleotide sequence encoding the polypeptide as set forth in SEQ ID NO: 2; and
   (c) a nucleotide sequence comprising nucleotide position number 181 to 795 in SEQ ID NO: 1.

2. A polypeptide produced by a process comprising steps of:
   expressing in a host cell an expression vector, wherein the expression vector comprises a nucleotide sequence selected from the group consisting of
      (a) the nucleotide sequence as get forth in SEQ ID NO: 1;
      (b) a nucleotide sequence encoding the polypeptide as set forth in SEQ ID NO: 2; and
      (c) a nucleotide sequence comprising nucleotide position number 181 to 795 in SEQ ID NO: 1; and
   isolating the polypeptide expressed from the expression vector in the host cell.

3. An isolated polypeptide comprising the amino acid sequence as set forth in SEQ ID NO: 2.

4. A fusion polypeptide comprising the polypeptide of claim 3 fused to a heterologous amino acid sequence.

5. The fusion polypeptide of claim 4 wherein the heterologous amino acid sequence is an IgG constant domain or fragment thereof.

* * * * *